United States Patent
Schmidt et al.

(10) Patent No.: US 11,141,412 B2
(45) Date of Patent: *Oct. 12, 2021

(54) ANALOGS OF PRIDOPIDINE, THEIR PREPARATION AND USE

(71) Applicant: PRILENIA NEUROTHERAPEUTICS LTD., Herzliya (IL)

(72) Inventors: Malle Schmidt, Tallinn (EE); Malle Pari, Tallinn (EE); Marit Laos, Tallinn (EE); Ants Maasalu, Tallinn (EE); Kalle Kaljuste, Tallinn (EE)

(73) Assignee: PRILENIA NEUROTHERAPEUTICS LTD., Herzliya (IL)

( * ) Notice: Subject to any disclaimer, the term of this patent is extended or adjusted under 35 U.S.C. 154(b) by 0 days.

This patent is subject to a terminal disclaimer.

(21) Appl. No.: 16/535,107

(22) Filed: Aug. 8, 2019

(65) Prior Publication Data

US 2020/0030308 A1     Jan. 30, 2020

Related U.S. Application Data

(60) Continuation of application No. 16/150,977, filed on Oct. 3, 2018, now Pat. No. 10,406,145, which is a
(Continued)

(51) Int. Cl.
*A61K 31/451* (2006.01)
*C07D 211/52* (2006.01)
(Continued)

(52) U.S. Cl.
CPC .......... *A61K 31/451* (2013.01); *C07D 211/24* (2013.01); *C07D 211/42* (2013.01);
(Continued)

(58) Field of Classification Search
None
See application file for complete search history.

(56) References Cited

U.S. PATENT DOCUMENTS

| 4,923,459 A | 5/1990 | Kyojiro et al. |
| 6,903,120 B2 | 6/2005 | Svan et al. |

(Continued)

FOREIGN PATENT DOCUMENTS

| WO | WO 2001/046144 A1 | 6/2001 |
| WO | WO 2001/046145 | 6/2001 |

(Continued)

OTHER PUBLICATIONS

BRIeFS, B. (Apr. 2010) "Trial watch: NeuroSearch's dopaminergic stabilizer improves movement disorders in Huntington's disease" Nature Reviews Drug Discovery 9, 260.
(Continued)

*Primary Examiner* — Heidi Reese
(74) *Attorney, Agent, or Firm* — Mark S. Cohen; Pearl Cohen Zedek Latzer Baratz LLP

(57) ABSTRACT

This invention provides an isolated compound having the structure:

(Continued)

or a salt thereof, processes for making the same and to compositions comprising pridopidine with these compounds.

26 Claims, 2 Drawing Sheets

Related U.S. Application Data division of application No. 14/754,339, filed on Jun. 29, 2015, now Pat. No. 10,130,621.

(60) Provisional application No. 62/076,436, filed on Nov. 6, 2014, provisional application No. 62/019,337, filed on Jun. 30, 2014.

(51) Int. Cl.
*C07D 211/24* (2006.01)
*C07D 211/42* (2006.01)
*G01N 30/88* (2006.01)

(52) U.S. Cl.
CPC .......... *C07D 211/52* (2013.01); *G01N 30/88* (2013.01); *G01N 2030/8872* (2013.01)

(56) References Cited

U.S. PATENT DOCUMENTS

| | | | |
|---|---|---|---|
| 7,417,043 B2 | 8/2008 | Svan et al. | |
| 7,579,474 B2 | 8/2009 | Sonesson et al. | |
| 7,923,459 B2 | 4/2011 | Gauthier et al. | |
| 9,006,445 B2 | 4/2015 | Sonesson et al. | |
| 9,012,476 B2 | 4/2015 | Zimmermann et al. | |
| 9,139,525 B2 * | 9/2015 | Wikstrom | A61P 25/22 |
| RE46,117 E | 8/2016 | Sonesson et al. | |
| 9,796,673 B2 | 10/2017 | Wu et al. | |
| 9,814,706 B2 | 11/2017 | Zimmerman et al. | |
| 10,047,049 B2 | 8/2018 | Barel et al. | |
| 10,322,119 B2 | 6/2019 | Bassan et al. | |
| 2007/0238878 A1 | 10/2007 | Desmond et al. | |
| 2007/0238879 A1 | 10/2007 | Gauthier et al. | |
| 2010/0076024 A1 | 3/2010 | Zimmermann et al. | |
| 2010/0105736 A1 | 4/2010 | Wikström | |
| 2010/0197712 A1 | 8/2010 | Carlsson et al. | |
| 2011/0206782 A1 | 8/2011 | Zhang et al. | |
| 2013/0150406 A1 | 6/2013 | Zimmermann et al. | |
| 2013/0197031 A1 | 8/2013 | Sonesson | |
| 2013/0267552 A1 | 10/2013 | Waters et al. | |
| 2014/0088140 A1 | 3/2014 | Hayden et al. | |
| 2014/0088145 A1 | 3/2014 | Hayden et al. | |
| 2015/0202302 A1 | 7/2015 | Licht et al. | |
| 2015/0209346 A1 | 7/2015 | Hayden et al. | |
| 2015/0216850 A1 | 8/2015 | Hayden et al. | |
| 2016/0095847 A1 | 4/2016 | Sonesson et al. | |
| 2016/0166559 A1 | 6/2016 | Sonesson et al. | |
| 2016/0243098 A1 | 8/2016 | Geva et al. | |
| 2017/0020854 A1 | 1/2017 | Licht et al. | |
| 2017/0022158 A1 | 1/2017 | Barel et al. | |
| 2017/0266170 A1 | 9/2017 | Waters et al. | |
| 2018/0235950 A1 | 8/2018 | Sonesson et al. | |
| 2019/0015401 A1 | 1/2019 | Sonesson | |
| 2019/0209542 A1 | 7/2019 | Licht et al. | |

FOREIGN PATENT DOCUMENTS

| | | |
|---|---|---|
| WO | WO 2005/121092 | 12/2005 |
| WO | WO 2006/040155 | 4/2006 |
| WO | WO 2008/127188 | 10/2008 |
| WO | WO 2012/002863 | 3/2012 |
| WO | WO 2013/034622 | 3/2013 |
| WO | WO 2013/086425 | 6/2013 |
| WO | WO 2013/152105 | 10/2013 |
| WO | WO 2014/205229 | 12/2014 |
| WO | WO 2015/112601 | 7/2015 |
| WO | WO 2016/003919 | 1/2016 |
| WO | WO 2016/138130 | 9/2016 |
| WO | WO 2016/138135 | 9/2016 |
| WO | WO 2017/015609 | 1/2017 |
| WO | WO 2017/015615 | 1/2017 |

OTHER PUBLICATIONS

Database PubChem [Online] U.S. National Library of medicine; Oct. 11, 2011, XP002775774, Database accession No. CID53379489.
De Yebenes, J. G., Landwehrmeyer, B., Squitieri, F., Reilmann, R., Rosser, A., Barker, R. A., . . . & Tedroff, J. (2011). Pridopidine for the treatment of motor function in patients with Huntington's disease (MermaIHD): a phase 3, randomised, double-blind, placebo-controlled trial. *The Lancet Neurology*, 10(12), 1049-1057.
Dyhring, T., Nielsen, E. Ø., Sonesson, C., Pettersson, F., Karlsson, J., Svensson, P., . . . & Waters, N. (2010). The dopaminergic stabilizers pridopidine (ACR16) and (-)-OSU6162 display dopamine D2 receptor antagonism and fast receptor dissociation properties. European journal of pharmacology, 628(1-3), 19-26.
European Search Report and Written Opinion, dated Dec. 8, 2017 in connection with EP Application No. 15814023.6.
Goodman, LaVonne, Huntington's Disease Drug Works, (Feb. 16, 2010)—ACR-16 (Huntexil). Trial Results: Good News from Europe.
Huntington Study Group HART Investigators. (2013). A randomized, double-blind, placebo-controlled trial of pridopidine in Huntington's disease. Movement Disorders, 28(10), 1407-1415.
International Search Report and Written Opinion of the International Searching Authority, dated Sep. 30, 2015 in connection with PCT International Application No. PCT/US2015/038349.
Johansson, B., Carlsson, A., Carlsson, M. L., Karlsson, M., Nilsson, M. K., Nordquist-Brandt, E., & Rönnbäck, L. (2012). Placebo-controlled cross-over study of the monoaminergic stabiliser (-)-OSU6162 in mental fatigue following stroke or traumatic brain injury. Acta Neuropsychiatrica, 24(5), 266-274.
Rung, J. P., Carlsson, A., Markinhuhta, K. R., & Carlsson, M.L. (2005). The dopaminergic stabilizers (-)-OSU6162 and ACR16 reverse (+)-MK-801-induced social withdrawal in rats. *Progress in Neuro-Psychopharmacology and Biological Psychiatry*, 29(5), 833-839.
Tedroff, J., Ekesbo, A., Sonesson, C., Waters, N., & Carlsson, A. (1999). Long-lasting improvement following (-)-OSU6162 in a patient with Huntington's disease. *Neurology*, 53(7), 1605-1605.

* cited by examiner

ANALOGS OF PRIDOPIDINE, THEIR PREPARATION AND USE

CROSS REFERENCE TO RELATED APPLICATIONS

This Application is a continuation of U.S. application Ser. No. 16/150,977 filed Oct. 3, 2018 (now U.S. Pat. No. 10,406,145), which is a divisional of U.S. application Ser. No. 14/754,339 filed Jun. 29, 2015 (now U.S. Pat. No. 10,130,621), which claims the benefit of U.S. Provisional Application No. 62/076,436, filed Nov. 6, 2014, and U.S. Provisional Application No. 62/019,337, filed Jun. 30, 2014, the entire contents of each of which are hereby incorporated by reference.

Disclosures of the publications cited in this application in their entireties are hereby incorporated by reference into this application in their entireties in order to more fully describe the state of the art as of the date of the invention described herein.

BACKGROUND OF THE INVENTION

Pridopidine (ACR16, TV-7820, Huntexil) is a unique compound developed for the treatment of patients with motor symptoms associated with Huntington's disease. Its chemical name is 4-(3-(Methylsulfonyl)phenyl)-1-propylpiperidine, and its Chemical Registry number is 882737-42-0 (U.S. Publication No. US-2013-0267552-A1). Processes of synthesis of pridopidine and a pharmaceutically acceptable salt thereof are disclosed in U.S. Pat. No. 7,923,459. U.S. Pat. No. 6,903,120 disclosed pridopidine for the treatment of Parkinson's disease, dyskinesias, dystonias, Tourette's disease, iatrogenic and non-iatrogenic psychoses and hallucinoses, mood and anxiety disorders, sleep disorder, autism spectrum disorder, ADHD, Huntington's disease, age-related cognitive impairment, and disorders related to alcohol abuse and narcotic substance abuse.

BRIEF SUMMARY OF THE INVENTION

This invention provides an isolated compound having the structure:

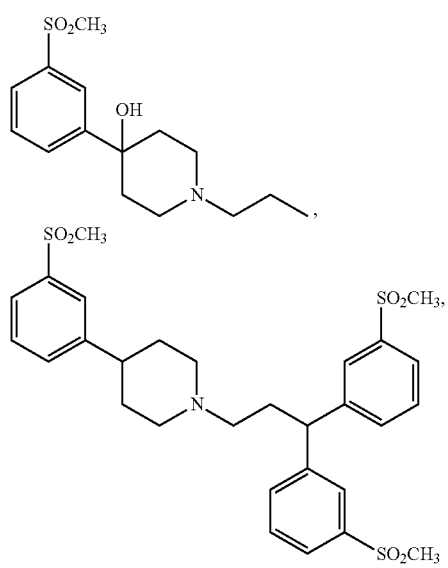

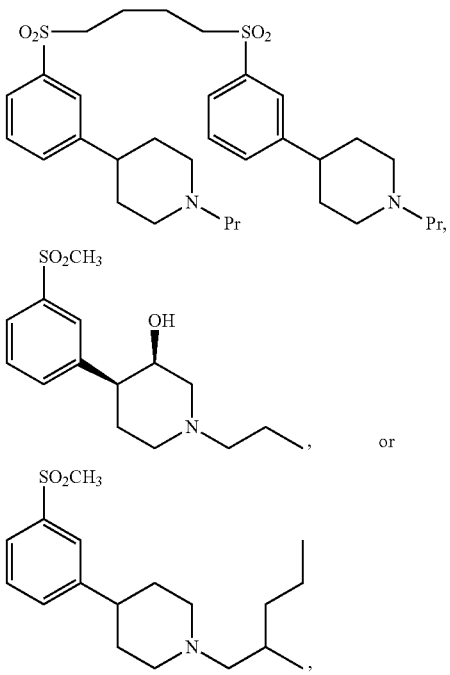

or, or a salt thereof.

This invention also provides a composition comprising pridopidine and a compound which has the structure:

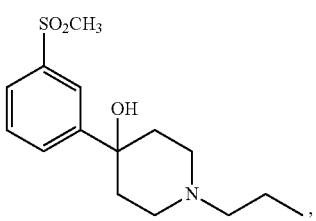

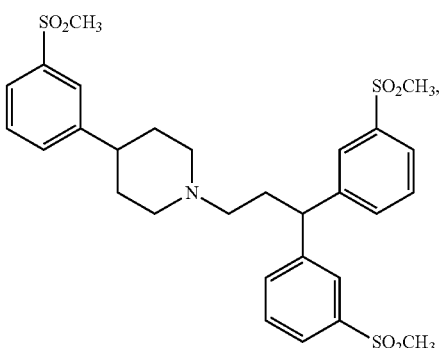

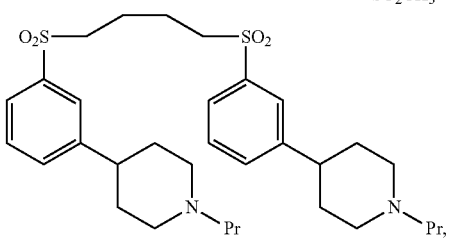

-continued

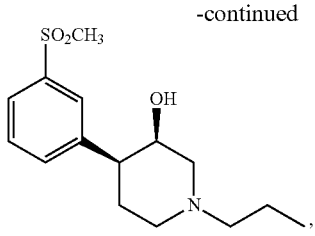

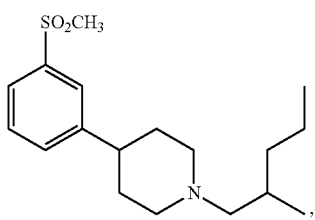

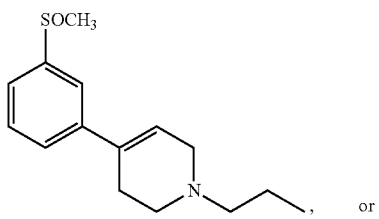, or

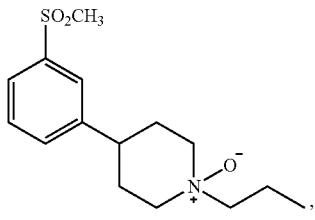

or a salt thereof, wherein the ration of the weight of the compound relative to the weight of the pridopidine in the composition is from 99:1 to 1:99.

This invention also provides a composition comprising a compound having the structure:

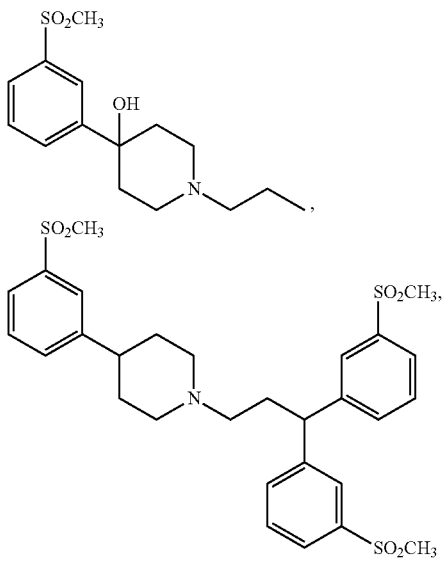

-continued

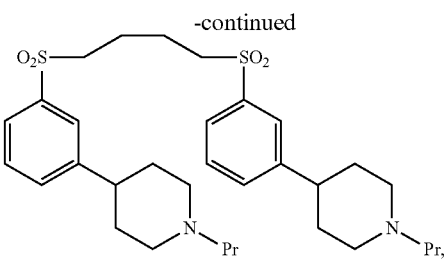

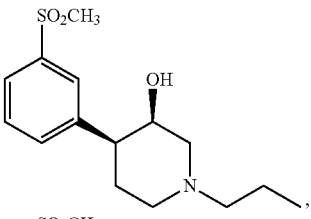

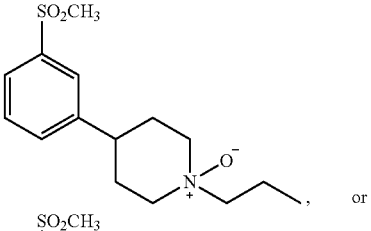, or

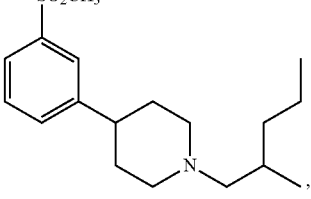

or a salt thereof, wherein the composition is free of pridopidine or a salt thereof.

The invention also provides a pharmaceutical composition comprising an amount of pridopidine and at least one of Compound 1, Compound 2, Compound 3, Compound 4, Compound 5, Compound 6, and Compound 7 wherein
  a) Compound 1 is present in the pharmaceutical composition in an amount not more than 10 area-% relative to the concentration of pridopidine, based on a determination by an HPLC method, or
  b) Compound 2 is present in the pharmaceutical composition in an amount not more than 10 area-% relative to the concentration of pridopidine, based on a determination by an HPLC method, or
  c) Compound 3 is present in the pharmaceutical composition in an amount not more than 10 area-% relative to the concentration of pridopidine, based on a determination by an HPLC method, or
  d) Compound 4 is present in the pharmaceutical composition in an amount not more than 10 area-% relative to the concentration of pridopidine, based on a determination by an HPLC method, or
  e) Compound 5 is present in the pharmaceutical composition in an amount not more than 10 area-% relative to the concentration of pridopidine, based on a determination by an HPLC method, or
  f) Compound 6 is present in the pharmaceutical composition in an amount not more than 10 area-% relative to the concentration of pridopidine, based on a determination by an HPLC method, or
  g) Compound 7 is present in the pharmaceutical composition in an amount not more than 10 area-% relative to the concentration of pridopidine, based on a determination by an HPLC method.

This invention also provides a process for preparing Compound 1 comprising the step of oxidizing 4-hydroxy-4-(3-(methylthio)phenyl)-1-propylpiperidin-1-ium chloride with an oxidizing agent to form Compound 1.

This invention also provides a process for preparing Compound 2 comprising the steps of:
a) reacting 3-bromothioanisole with ethyl 3-(4-oxopiperidin-1-yl)propanoate to form 1-(3-hydroxy-3,3-bis(3-(methylthio)phenyl)propyl)-4-(3-(methylthio)phenyl)piperidin-4-ol,
b) dehydrating the 1-(3-hydroxy-3,3-bis(3-(methylthio)phenyl)propyl)-4-(3-(methylthio)phenyl)piperidin-4-ol formed in step a) with a dehydrating agent to obtain 1-(3,3-bis(3-(methylthio)phenyl)allyl)-4-(3-(methylthio)phenyl)-1,2,3,6-tetrahydropyridine,
c) oxidizing the 1-(3,3-bis(3-(methylsulfonyl)phenyl)allyl)-4-(3-(methylsulfonyl) phenyl)-1,2,3,6-tetrahydropyridine formed in step b) with an oxidizing agent to form 1-(3,3-bis(3-(methylsulfonyl)phenyl)allyl)-4-(3-(methylsulfonyl)phenyl)-1,2,3,6-tetrahydropyridine, and
d) hydrogenating the 1-(3,3-bis(3-(methylsulfonyl)phenyl)allyl)-4-(3-(methylsulfonyl) phenyl)-1,2,3,6-tetrahydropyridine formed in step c) with a hydrogenating agent to form Compound 2.

This invention also provides a process for preparing Compound 3 comprising the steps of:
a) reacting 3-bromo thiophenol and 1,4-dibromobutane to form 1,4-bis((3-bromophenyl)thio)butane,
b) oxidizing the 1,4-bis((3-bromophenyl)thio)butane formed in step a) with an oxidizing agent to form 1,4-bis((3-bromophenyl)sulfonyl)butane,
c) reacting 4-pyridinylboronic acid with the 1,4-bis((3-bromophenyl)sulfonyl)butane formed in step b) to obtain 1,4-bis((3-(pyridin-4-yl)phenyl)sulfonyl)butane,
d) reacting 1-iodopropane with 1,4-bis((3-(pyridin-4-yl)phenyl)sulfonyl)butane formed in step c) to form 4,4'-((butane-1,4-diyldisulfonyl)bis(3,1-phenylene))bis(1-propylpyridin-1-ium)iodide,
e) adding a reducing agent to 4,4'-((butane-1,4-diyldisulfonyl)bis(3,1-phenylene))bis(1-propylpyridin-1-ium) iodide formed in step d) to form 1,4-bis((3-(1-propyl-1,2,3,6-tetrahydropyridin-4-yl)phenyl)sulfonyl) butane, and
f) hydrogenating the 1,4-bis((3-(1-propyl-1,2,3,6-tetrahydropyridin-4-yl)phenyl)sulfonyl) butane formed in step e) with a hydrogenating agent to obtain Compound 3.

This invention also provides a process for preparing Compound 4 comprising the steps of:
a) epoxidizing 4-(3-(methylsulfonyl)phenyl)-1-propyl-1,2,3,6-tetrahydropyridine with an epoxidizing agent to form (1S,6S)-6-(3-(methylsulfonyl)phenyl)-3-propyl-7-oxa-3-azabicyclo [4.1.0]heptane, and
b) nucleophilically opening the epoxide of the (1S,6S)-6-(3-(methylsulfonyl)phenyl)-3-propyl-7-oxa-3-azabicyclo [4.1.0]heptane of step a) with a nucleophile to obtain Compound 4.

This invention also provides a process for preparing Compound 5 comprising the step of reacting pridopidine with a peroxide to obtain Compound 5.

This invention also provides a process for preparing Compound 6 comprising the step of reacting 4-(3-(methylsulfonyl)phenyl)piperidine with 1-chloro-2-methylpentane to obtain Compound 6.

This invention also provides a process for preparing Compound 7 comprising the steps of:
a) dehydrating 4-hydroxy-4-(3-(methylsulfonyl)phenyl)-1-propylpiperidin-1-ium chloride with a dehydrating agent to form 4-(3-(methylthio)phenyl)-1-propyl-1,2,3,6-tetrahydropyridin-1-ium hydrogen sulfate,
b) oxidizing 4-(3-(methylthio)phenyl)-1-propyl-1,2,3,6-tetrahydropyridin-1-ium hydrogen sulfate of step b) with an oxidizing agent to form Compound 7. In one embodiment, the dehydrating agent is a strong acid, preferably sulphuric acid. In another embodiment, the dehydrating agent is a strong acid. In another embodiment, the dehydrating agent is sulphuric acid. In another embodiment, the oxidizing agent is a peroxide, preferably hydrogen peroxide. In another embodiment, the oxidizing agent is a peroxide. In another embodiment, the oxidizing agent is hydrogen peroxide.

This invention also provides a process for testing whether a sample of a composition comprising pridopidine contains an undesirable impurity which comprises the step of determining whether the sample contains a compound having the structure:

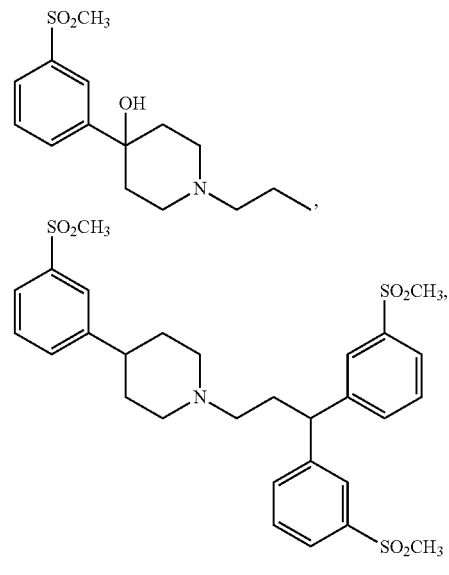

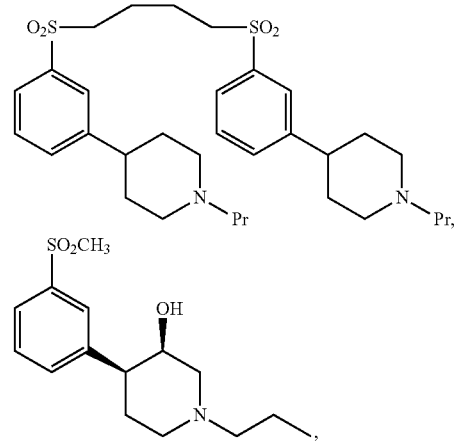

-continued

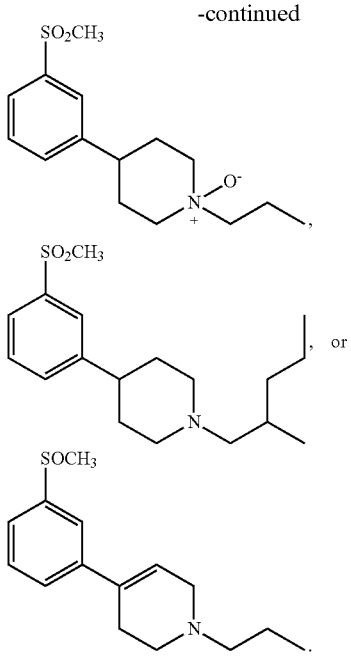

This invention also provides a process for producing a pridopidine drug product comprising obtaining a pridopidine drug substance and mixing the pridopidine drug substance with suitable excipients so as to produce the pridopidine drug product, wherein the pridopidine drug substance comprises:
  i) an amount of Compound 1 in the pridopidine drug substance that is not more than 0.15 area-% Compound 1, relative to the concentration of pridopidine, or
  ii) an amount of Compound 2 in the pridopidine drug substance that is not more than 0.15 area-% Compound 2, relative to the concentration of pridopidine, or
  iii) an amount of Compound 3 in the pridopidine drug substance that is not more than 0.15 area-% Compound 3, relative to the concentration of pridopidine, or
  iv) an amount of Compound 4 in the pridopidine drug substance that is not more than 0.15 area-% Compound 4, relative to the concentration of pridopidine, or
  v) an amount of Compound 5 in the pridopidine drug substance that is not more than 0.15 area-% Compound 5, relative to the concentration of pridopidine, or
  vi) an amount of Compound 6 in the pridopidine drug substance that is not more than 0.15 area-% Compound 6, relative to the concentration of pridopidine.

This invention also provides a process for producing a pridopidine drug product for commercial sale comprising obtaining a batch of pridopidine drug product that comprises:
  i) an amount of Compound 1 in the batch of pridopidine drug product that is not more than 0.15 area-% Compound 1, relative to the concentration of pridopidine, or
  ii) an amount of Compound 2 in the batch of pridopidine drug product that is not more than 0.15 area-% Compound 2, relative to the concentration of pridopidine, or
  iii) an amount of Compound 3 in the batch of pridopidine drug product that is not more than 0.15 area-% Compound 3, relative to the concentration of pridopidine, or
  iv) an amount of Compound 4 in the batch of pridopidine drug product that is not more than 0.15 area-% Compound 4, relative to the concentration of pridopidine, or
  v) an amount of Compound 5 in the batch of pridopidine drug product that is not more than 0.15 area-% Compound 5, relative to the concentration of pridopidine, or
  vi) an amount of Compound 6 in the batch of pridopidine drug product that is not more than 0.15 area-% Compound 6, relative to the concentration of pridopidine, and
preparing the batch of pridopidine drug product for commercial sale.

This invention also provides a process of distributing a pridopidine drug product comprising a pridopidine drug substance comprising,
  a) obtaining the pridopidine drug product wherein the pridopidine drug substance comprises:
    i) an amount of Compound 1 in the pridopidine drug substance that is not more than 0.15 area-% Compound 1, relative to the concentration of pridopidine, or
    ii) an amount of Compound 2 in the pridopidine drug substance that is not more than 0.15 area-% Compound 2, relative to the concentration of pridopidine, or
    iii) an amount of Compound 3 in the pridopidine drug substance that is not more than 0.15 area-% Compound 3, relative to the concentration of pridopidine, or
    iv) an amount of Compound 4 in the pridopidine drug substance that is not more than 0.15 area-% Compound 4, relative to the concentration of pridopidine, or
    v) an amount of Compound 5 in the pridopidine drug substance that is not more than 0.15 area-% Compound 5, relative to the concentration of pridopidine, or
    vi) an amount of Compound 6 in the pridopidine drug substance that is not more than 0.15 area-% Compound 6, relative to the concentration of pridopidine; and
  b) distributing the pridopidine drug product comprising the pridopidine drug substance.

This invention also provides a process of distributing a pridopidine drug product comprising,
  a) obtaining the pridopidine drug product that comprises:
    i) an amount of Compound 1 in the pridopidine drug product that is not more than 0.15 area-% Compound 1, relative to the concentration of pridopidine, or
    ii) an amount of Compound 2 in the pridopidine drug product that is not more than 0.15 area-% Compound 2, relative to the concentration of pridopidine, or
    iii) an amount of Compound 3 in the pridopidine drug product that is not more than 0.15 area-% Compound 3, relative to the concentration of pridopidine, or
    iv) an amount of Compound 4 in the pridopidine drug product that is not more than 0.15 area-% Compound 4, relative to the concentration of pridopidine, or
    v) an amount of Compound 5 in the pridopidine drug product that is not more than 0.15 area-% Compound 5, relative to the concentration of pridopidine, or
    vi) an amount of Compound 6 in the pridopidine drug product that is not more than 0.15 area-% Compound 6, relative to the concentration of pridopidine; and
  b) distributing the pridopidine drug product.

This invention also provides an impurity or a salt thereof for use, as a reference standard to detect trace amounts of the impurity in a pharmaceutical composition comprising pridopidine or a pharmaceutically acceptable salt thereof, wherein the impurity is selected from the group consisting of Compound 1, Compound 2, Compound 3, Compound 4, Compound 5 and Compound 6.

This invention also provides a method of determining the concentration of an impurity in a pharmaceutical composition comprising pridopidine, the method comprising,
   a) preparing a sample solution from the pharmaceutical composition,
   b) preparing a diluent solution comprising methanol and water,
   c) preparing a standard solution comprising pridopidine and the diluent solution,
   d) preparing a resolution solution comprising pridopidine and the impurity,
   e) preparing a buffer solution by dissolving ammonium formate in water and adjusting to pH of 9.0±0.10 with aqueous ammonia hydroxide or formic acid,
   f) injecting into the HPLC the diluent solution, the resolution solution, the standard solution, and the sample solution,
   g) running the HPLC using ultraviolet absorption at 190-400 nm or 268 nm and a mixture of the buffer solution, methanol and water as the mobile phase,
   h) determining the retention time (RT) and the areas of the peaks of the impurity in the chromatograms of the sample solution, and
   i) performing quantitation of the impurity with respect to the corresponding peaks in the chromatograms of the sample solution,
   wherein the impurity is Compound 1, Compound 2, Compound 3, Compound 4, Compound 5 or Compound 6.

This invention also provides a method of determining the concentration of an impurity in a pharmaceutical composition comprising pridopidine, the method comprising
   a) preparing a sample solution from the pharmaceutical composition,
   b) preparing a diluent solution comprising methanol and water,
   c) preparing a standard solution comprising the impurity,
   d) preparing a resolution solution comprising pridopidine and the impurity,
   e) preparing a buffer solution by dissolving ammonium formate in water and adjusting to pH of 9.0±0.10 with aqueous ammonia hydroxide or formic acid,
   f) injecting into the HPLC the diluent solution, the resolution solution, the standard solution, and the sample solution,
   g) running the HPLC using ultraviolet absorption at 190-400 nm or 268 nm and a mixture of the buffer solution, methanol and water as the mobile phase,
   h) determining the retention time (RT) and the areas of the peaks of the impurity in the chromatograms of the sample solution, and
   i) performing quantitation of the impurity with respect to the corresponding peaks in the chromatograms of the standard solutions,
   wherein the impurity is Compound 1, Compound 2, Compound 3, Compound 4, Compound 5 or Compound 6.

This invention also provides a method of determining the concentration of an impurity in a pharmaceutical composition comprising pridopidine and a pharmaceutically acceptable carrier, the method comprising,
   a) preparing a sample solution from the pharmaceutical composition,
   b) preparing a diluent solution comprising methanol and water,
   c) preparing a standard solution comprising pridopidine and the diluent solution,
   d) preparing a resolution solution comprising pridopidine and the impurity,
   e) preparing a buffer solution by dissolving ammonium formate in water and adjusting to pH of 9.0±0.10 with aqueous ammonia hydroxide or formic acid,
   f) injecting into the HPLC the diluent solution, the resolution solution, the standard solution, and the sample solution,
   g) running the HPLC using ultraviolet absorption at 190-400 nm or 268 nm and a mixture of the buffer solution, methanol and water as the mobile phase,
   h) determining the retention time (RT) and the areas of the peaks of the impurity in the chromatograms of the sample solution, and
   i) performing quantitation of the impurity with respect to the corresponding peaks in the chromatograms of the sample solution,
   wherein the impurity is Compound 1, Compound 2, Compound 3, Compound 4, Compound 5 or Compound 6.

This invention also provides a method of determining the concentration of an impurity in a pharmaceutical composition comprising pridopidine and a pharmaceutically acceptable carrier, the method comprising,
   a) preparing a sample solution from the pharmaceutical composition,
   b) preparing a diluent solution comprising methanol and water,
   c) preparing a standard solution comprising the impurity,
   d) preparing a resolution solution comprising pridopidine and the impurity,
   e) preparing a buffer solution by dissolving ammonium formate in water and adjusting to pH of 9.0±0.10 with aqueous ammonia hydroxide or formic acid,
   f) injecting into the HPLC the diluent solution, the resolution solution, the standard solution, and the sample solution,
   g) running the HPLC using ultraviolet absorption at 190-400 nm or 268 nm and a mixture of the buffer solution, methanol and water as the mobile phase,
   h) determining the retention time (RT) and the areas of the peaks of the impurity in the chromatograms of the sample solution, and
   i) performing quantitation of the impurity with respect to the corresponding peaks in the chromatograms of the standard solutions,
   wherein the impurity is Compound 1, Compound 2, Compound 3, Compound 4, Compound 5 or Compound 6.

This invention also provides a method of treating a subject afflicted with a neurodegenerative disease or a neurodegenerative disorder comprising administering to the subject the pharmaceutical composition.

This invention also provides a method of treating a subject afflicted with Huntington's disease comprising administering to the subject the pharmaceutical composition.

This invention also provides a process for validating a batch of a pharmaceutical product containing pridopidine or a pharmaceutically acceptable salt thereof and a pharmaceutically acceptable carrier for distribution comprising:
   a) determining the amount of at least one of Compound 1, Compound 2, Compound 3, Compound 4, Compound 5, and Compound 6; and b) validating the batch for distribution only if
   i) the batch is determined to have not more than 0.15 area-% Compound 1, relative to the concentration of pridopidine, or
   ii) the batch is determined to have not more than 0.15 area-% Compound 2, relative to the concentration of pridopidine, or
   iii) the batch is determined to have not more than 0.15 area-% Compound 3, relative to the concentration of pridopidine, or
   iv) the batch is determined to have not more than 0.15 area-% Compound 4, relative to the concentration of pridopidine, or
   v) the batch is determined to have not more than 0.15 area-% Compound 5, relative to the concentration of pridopidine, or
   vi) the batch is determined to have not more than 0.15 area-% Compound 6, relative to the concentration of pridopidine.

This invention also provides a process for preparing a validated pharmaceutical composition comprising pridopidine comprising:
a) obtaining a batch of pridopidine drug substance;
b) determining the amount of at least one of Compound 1, Compound 2, Compound 3, Compound 4, Compound 5, and Compound 6; and
c) preparing the pharmaceutical composition from the batch only if
   i) the batch is determined to have not more than 0.15% Compound 1, relative to the concentration of pridopidine, or
   ii) the batch is determined to have not more than 0.15%/Compound 2, relative to the concentration of pridopidine, or
   iii) the batch is determined to have not more than 0.15% Compound 3, relative to the concentration of pridopidine, or
   iv) the batch is determined to have not more than 0.15% Compound 4, relative to the concentration of pridopidine, or
   v) the batch is determined to have not more than 0.15% Compound 5, relative to the concentration of pridopidine, or
   vi) the batch is determined to have not more than 0.15% Compound 6, relative to the concentration of pridopidine.

This invention also provides a process for preparing a pharmaceutical composition comprising pridopidine, comprising
a) obtaining a batch of pridopidine drug product;
b) performing stability testing with a sample of the batch;
c) determining the total amount of at least one of Compound 1, Compound 2, Compound 3, Compound 4, Compound 5, and Compound 6 in the sample of the batch after stability testing by an HPLC method; and
d) preparing the pharmaceutical composition from the batch after stability testing if the sample of the batch after stability testing contains:
   i) not more than 0.15% Compound 1, relative to the concentration of pridopidine, or
   ii) not more than 0.15% Compound 2, relative to the concentration of pridopidine, or
   iii) not more than 0.15% Compound 3, relative to the concentration of pridopidine, or
   iv) not more than 0.15% Compound 4, relative to the concentration of pridopidine, or
   v) not more than 0.15% Compound 5, relative to the concentration of pridopidine, or
   vi) not more than 0.15% Compound 6, relative to the concentration of pridopidine.

This invention also provides an isolated compound having the structure:

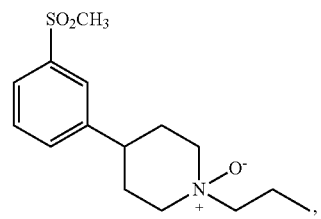

or a salt thereof.

BRIEF DESCRIPTION OF THE SEVERAL VIEWS OF THE DRAWINGS

FIG. 1: Typical Chromatogram of the control sample 1a.

DETAILED DESCRIPTION OF THE INVENTION

Figure 1:
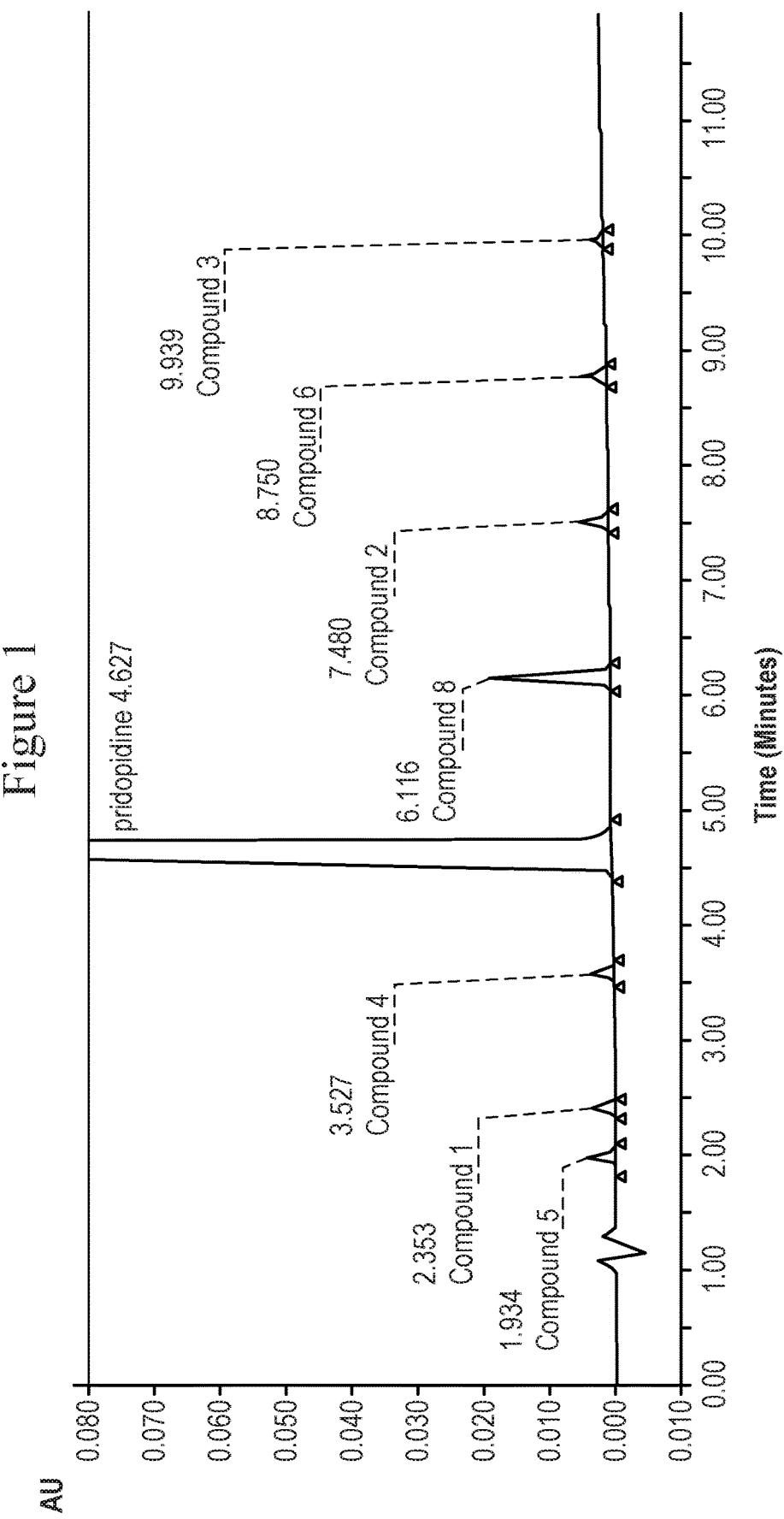

This invention provides an isolated compound having the structure:

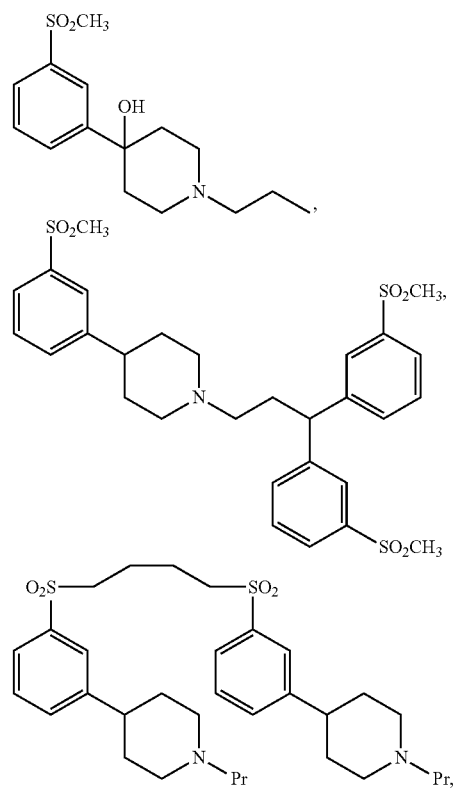

-continued

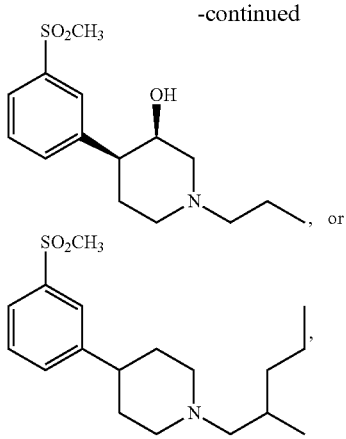

, or

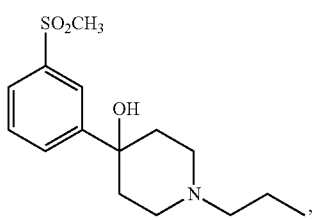 [SMILES: CCCN1CCC(O)(c2cccc(S(C)(=O)=O)c2)CC1]

, or, or a salt thereof.

In an embodiment of the present invention, the isolated compound has the structure:

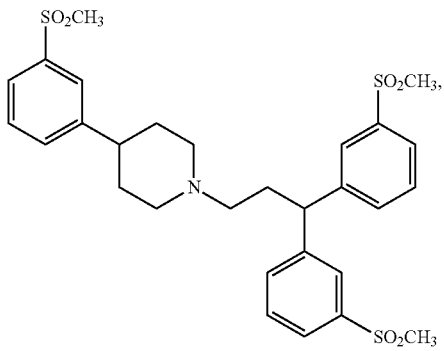 [SMILES: CS(=O)(=O)c1cccc(C2CCN(CCC(c3cccc(S(C)(=O)=O)c3)c3cccc(S(C)(=O)=O)c3)CC2)c1]

, or a salt thereof.

In an embodiment, the isolated compound has the structure:

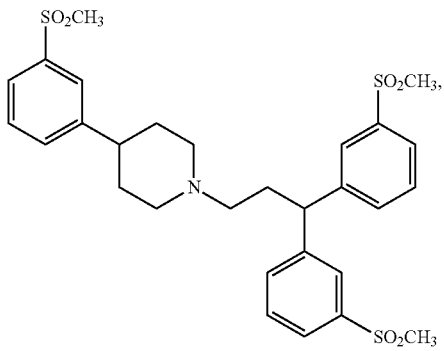 [SMILES: CS(=O)(=O)c1cccc(C2CCN(CCC(c3cccc(S(C)(=O)=O)c3)c3cccc(S(C)(=O)=O)c3)CC2)c1]

or a salt thereof.

In an embodiment, the isolated compound has the structure:

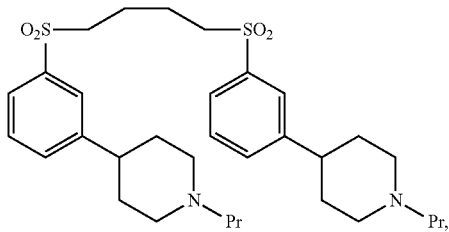

or a salt thereof.

In an embodiment, the isolated compound has the structure:

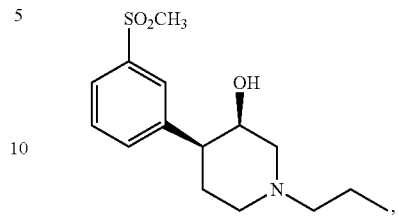

, or a salt thereof.

In an embodiment, the isolated compound has the structure:

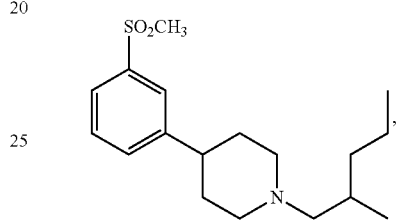

, or a salt thereof.

This invention also provides a composition comprising pridopidine and a compound which has the structure:

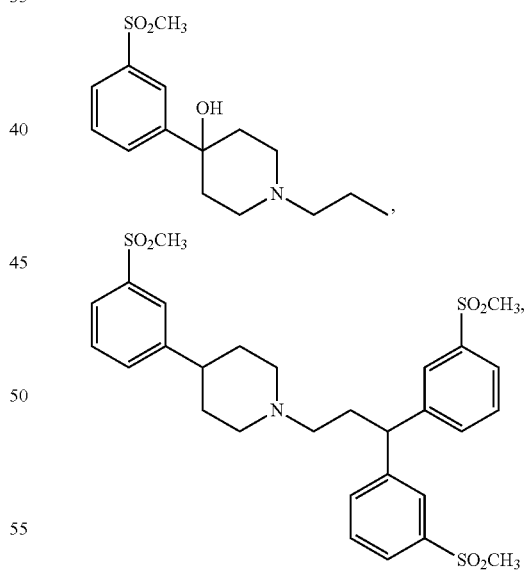

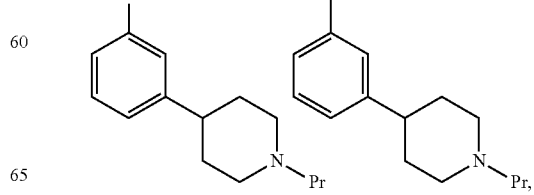

-continued

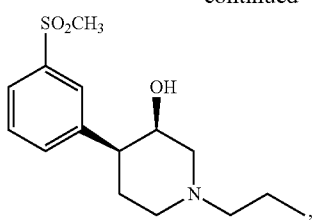

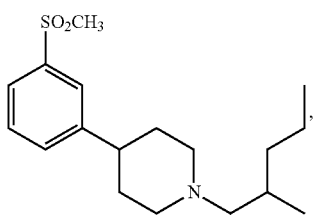

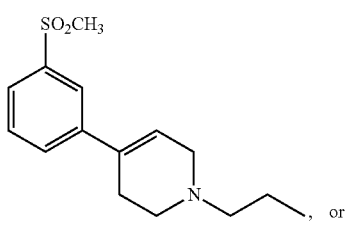, or

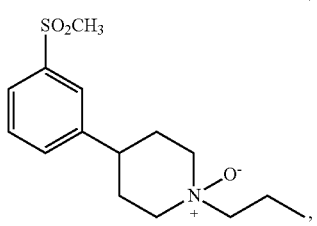

or a salt thereof, wherein the ratio of the weight of the compound relative to the weight of the pridopidine in the composition is from 99:1 to 1:99.

In an embodiment, the compound has the structure:

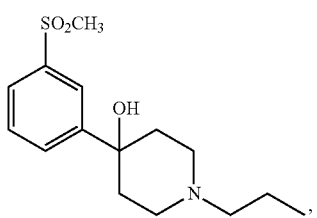

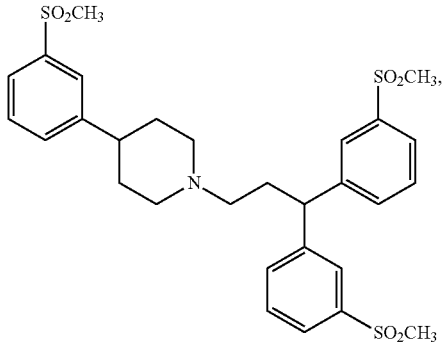

-continued

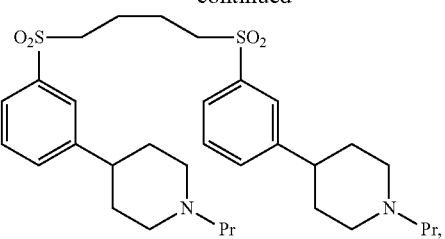

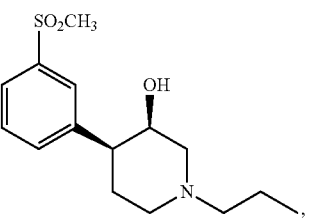 [SMILES: CCCN1CC[C@@H](c2cccc(S(C)(=O)=O)c2)[C@@H](O)C1]

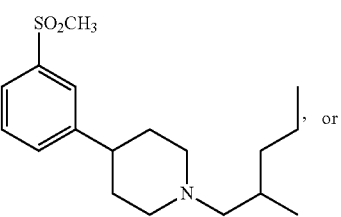, or

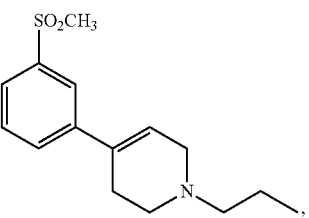

or a salt thereof.

In an embodiment, the ratio of the weight of the compound relative to the weight of the pridopidine in the composition is from 90:10 to 10:90 or 85:15 or 15:85.

This invention also provides a composition comprising a compound having the structure:

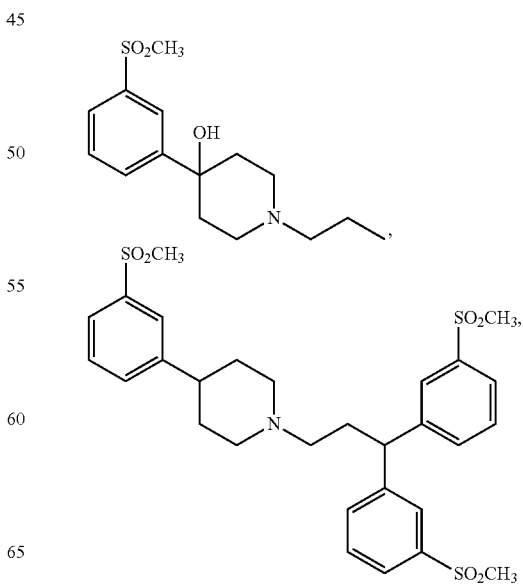

-continued

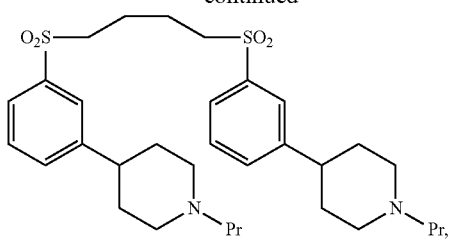

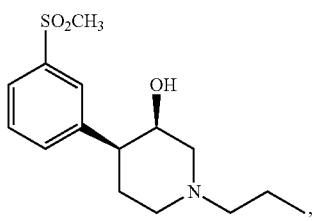

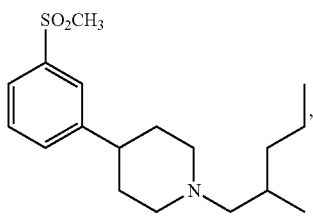 [SMILES: CCCC(C)CN1CCC(c2cccc(S(C)(=O)=O)c2)CC1]

or a salt thereof, wherein the composition is free of pridopidine or a salt thereof.

In an embodiment, the compound has the structure:

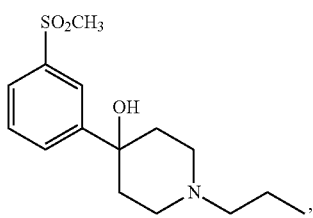 [SMILES: CCCN1CCC(O)(c2cccc(S(C)(=O)=O)c2)CC1]

or a salt thereof.

In an embodiment, the compound has the structure:

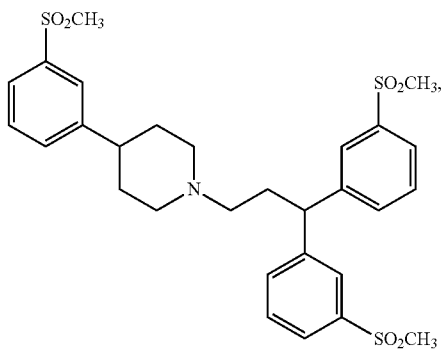 [SMILES: CS(=O)(=O)c1cccc(C2CCN(CCC(c3cccc(S(C)(=O)=O)c3)c3cccc(S(C)(=O)=O)c3)CC2)c1]

or a salt thereof.

In an embodiment, the compound has the structure:

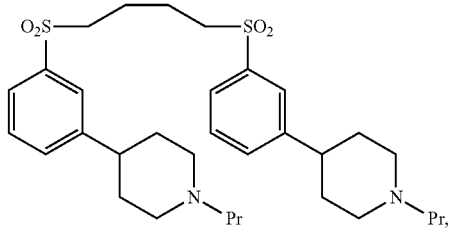

or a salt thereof.

In an embodiment, the compound has the structure:

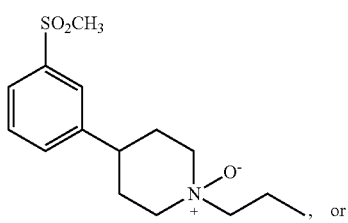

or a salt thereof.

In an embodiment, the compound has the structure:

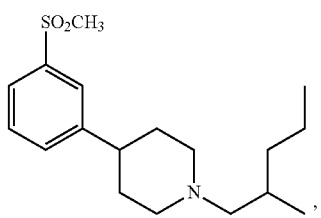 [SMILES: CCCC(C)CN1CCC(c2cccc(S(C)(=O)=O)c2)CC1]

or a salt thereof.

In an embodiment, the compound has the structure:

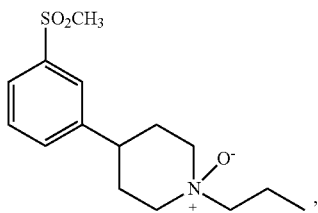

or a salt thereof.

In an embodiment, the compound has the structure:

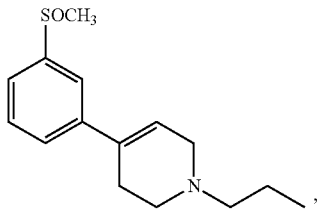

or a salt thereof.

The invention also provides a pharmaceutical composition comprising an amount of pridopidine and at least one of Compound 1, Compound 2, Compound 3, Compound 4, Compound 5, Compound 6, and Compound 7 wherein
a) Compound 1 is present in the pharmaceutical composition in an amount not more than 10 area-% relative to the concentration of pridopidine, based on a determination by an HPLC method, or
b) Compound 2 is present in the pharmaceutical composition in an amount not more than 10 area-% relative to the concentration of pridopidine, based on a determination by an HPLC method, or
c) Compound 3 is present in the pharmaceutical composition in an amount not more than 10 area-% relative to the concentration of pridopidine, based on a determination by an HPLC method, or
d) Compound 4 is present in the pharmaceutical composition in an amount not more than 10 area-% relative to the concentration of pridopidine, based on a determination by an HPLC method, or
e) Compound 5 is present in the pharmaceutical composition in an amount not more than 10 area-% relative to the concentration of pridopidine, based on a determination by an HPLC method, or
f) Compound 6 is present in the pharmaceutical composition in an amount not more than 10 area-% relative to the concentration of pridopidine, based on a determination by an HPLC method, or
g) Compound 7 is present in the pharmaceutical composition in an amount not more than 10 area-% relative to the concentration of pridopidine, based on a determination by an HPLC method.

In an embodiment,
a) Compound 1 is present in the pharmaceutical composition in an amount not more than 0.15 area-% relative to the concentration of pridopidine, based on a determination by an HPLC method, or
b) Compound 2 is present in the pharmaceutical composition in an amount not more than 0.15 area-% relative to the concentration of pridopidine, based on a determination by an HPLC method, or
c) Compound 3 is present in the pharmaceutical composition in an amount not more than 0.15 area-% relative to the concentration of pridopidine, based on a determination by an HPLC method, or
d) Compound 4 is present in the pharmaceutical composition in an amount not more than 0.15 area-% relative to the concentration of pridopidine, based on a determination by an HPLC method, or
e) Compound 5 is present in the pharmaceutical composition in an amount not more than 0.15 area-% relative to the concentration of pridopidine, based on a determination by an HPLC method, or
f) Compound 6 is present in the pharmaceutical composition in an amount not more than 0.15 area-% relative to the concentration of pridopidine, based on a determination by an HPLC method.

In another embodiment,
a) Compound 1 is present in the pharmaceutical composition in an amount greater than 0.01 area-%, and not more than 0.15 area-% relative to the concentration of pridopidine, based on a determination by an HPLC method, or
b) Compound 2 is present in the pharmaceutical composition in an amount greater than 0.01 area-%, and not more than 0.15 area-%, relative to the concentration of pridopidine, based on a determination by an HPLC method, or
c) Compound 3 is present in the pharmaceutical composition in an amount greater than 0.03 area-%, and not more than 0.15 area-%, relative to the concentration of pridopidine, based on a determination by an HPLC method, or
d) Compound 4 is present in the pharmaceutical composition in an amount greater than 0.01 area-%, and not more than 0.15 area-%, relative to the concentration of pridopidine, based on a determination by an HPLC method, or
e) Compound 5 is present in the pharmaceutical composition in an amount greater than 0.01 area-%, and not more than 0.15 area-%, relative to the concentration of pridopidine, based on a determination by an HPLC method, or
f) Compound 6 is present in the pharmaceutical composition in an amount greater than 0.01 area-% and not more than 0.15 area-%, relative to the concentration of pridopidine, based on a determination by an HPLC method.

In another embodiment,
a) Compound 1 is present in the pharmaceutical composition in an amount less than 0.04 area-% relative to the concentration of pridopidine, based on a determination by an HPLC method, or
b) Compound 2 is present in the pharmaceutical composition in an amount less than 0.05 area %, relative to the concentration of pridopidine, based on a determination by an HPLC method, or
c) Compound 3 is present in the pharmaceutical composition in an amount less than 0.05 area-% relative to the concentration of pridopidine, based on a determination by an HPLC method, or
d) Compound 4 is present in the pharmaceutical composition in an amount less than 0.04 area-% relative to the concentration of pridopidine, based on a determination by an HPLC method, or e) Compound 5 is present in the pharmaceutical composition in an amount less than 0.04 area-% relative to the concentration of pridopidine, based on a determination by an HPLC method, or
f) Compound 6 is present in the pharmaceutical composition in an amount less than 0.04 area-% relative to the concentration of pridopidine, based on a determination by an HPLC method.

In another embodiment,
a) Compound 1 is present in the pharmaceutical composition in an amount less than 0.01 area-% relative to the concentration of pridopidine, based on a determination by an HPLC method, or
b) Compound 2 is present in the pharmaceutical composition in an amount less than 0.01 area-% relative to the concentration of pridopidine, based on a determination by an HPLC method, or
c) Compound 3 is present in the pharmaceutical composition in an amount less than 0.03 area-% relative to the concentration of pridopidine, based on a determination by an HPLC method, or
d) Compound 4 is present in the pharmaceutical composition in an amount less than 0.01 area-% relative to the concentration of pridopidine, based on a determination by an HPLC method, or
e) Compound 5 is present in the pharmaceutical composition in an amount less than 0.01 area-% relative to the concentration of pridopidine, based on a determination by an HPLC method, or
f) Compound 6 is present in the pharmaceutical composition in an amount less than 0.01 area-% relative to the concentration of pridopidine, based on a determination by an HPLC method.

In one embodiment, at least two of Compound 1, Compound 2, Compound 3, Compound 4, Compound 5 and Compound 6 are present. In another embodiment, at least three of Compound 1, Compound 2, Compound 3, Compound 4, Compound 5 and Compound 6 are present. In another embodiment, at least four of Compound 1, Compound 2, Compound 3, Compound 4, Compound 5 and Compound 6 are present. In another embodiment, least five of Compound 1, Compound 2, Compound 3, Compound 4, Compound 5 and Compound 6 are present. In another embodiment, Compound 1, Compound 2, Compound 3, Compound 4, Compound 5 and Compound 6 are present. In another embodiment, at least Compound 1 is present. In another embodiment, at least Compound 3 is present. In another embodiment, at least Compound 4 is present.

In one embodiment, the pharmaceutical composition comprises pridopidine hydrochloride salt.

In an embodiment, the pharmaceutical composition is in the form of a capsule, a tablet, or a liquid suspension. In another embodiment, the pharmaceutical composition is in an oral dosage unit form.

In an embodiment, the pharmaceutical composition the oral dosage unit form comprises between 22.5-315 mg pridopidine. In another embodiment, the oral dosage unit form comprises between 45-250 mg pridopidine. In another embodiment, the oral dosage unit form comprises between 45-135 mg pridopidine. In another embodiment, the oral dosage unit form comprises between 90-315 mg pridopidine. In another embodiment, the oral dosage unit form comprises about 22.5 mg pridopidine. In another embodiment, the oral dosage unit form comprises about 45 mg pridopidine. In another embodiment, the oral dosage unit form comprises about 67.5 mg pridopidine. In another embodiment the oral dosage unit form comprises about 90 mg pridopidine. In another embodiment, the oral unit dosage form comprises about 100 mg pridopidine. In another embodiment, the oral dosage unit form comprises about 112.5 mg pridopidine. In another embodiment, the oral dosage unit form comprises about 125 mg pridopidine. In another embodiment, the oral dosage unit form comprises about 135 mg pridopidine. In another embodiment, the oral dosage unit form comprises about 150 mg pridopidine. In another embodiment, the oral dosage unit form comprises about 180 mg pridopidine. In another embodiment, the oral dosage unit form comprises about 200 mg pridopidine. In another embodiment, the oral dosage unit form comprises about 250 mg pridopidine. In another embodiment, the oral dosage unit form comprises about 315 mg pridopidine. In another embodiment, the oral dosage unit form is prepared for once daily administration. In another embodiment, the oral dosage unit form is prepared for more than once daily administration.

This invention also provides a process for preparing Compound 1 comprising the step of oxidizing 4-hydroxy-4-(3-(methylthio)phenyl)-1-propylpiperidin-1-ium chloride with an oxidizing agent to form Compound 1. In one embodiment, the oxidizing agent is a peroxide, preferably hydrogen peroxide. In another embodiment, the oxidizing agent is a peroxide. In another embodiment, the oxidizing agent is hydrogen peroxide.

This invention also provides a process for preparing Compound 2 comprising the steps of:
a) reacting 3-bromothioanisole with ethyl 3-(4-oxopiperidin-1-yl)propanoate to form 1-(3-hydroxy-3,3-bis(3-(methylthio)phenyl)propyl)-4-(3-(methylthio)phenyl)piperidin-4-ol,
b) dehydrating the 1-(3-hydroxy-3,3-bis(3-(methylthio)phenyl)propyl)-4-(3-(methylthio)phenyl)piperidin-4-ol formed in step a) with a dehydrating agent to obtain 1-(3,3-bis(3-(methylthio)phenyl)allyl)-4-(3-(methylthio)phenyl)-1,2,3,6-tetrahydropyridine,
c) oxidizing the 1-(3,3-bis(3-(methylsulfonyl)phenyl)allyl)-4-(3-(methylsulfonyl) phenyl)-1,2,3,6-tetrahydropyridine formed in step b) with an oxidizing agent to form 1-(3,3-bis(3-(methylsulfonyl)phenyl)allyl)-4-(3-(methylsulfonyl)phenyl)-1,2,3,6-tetrahydropyridine, and
d) hydrogenating the 1-(3,3-bis(3-(methylsulfonyl)phenyl)allyl)-4-(3-(methylsulfonyl) phenyl)-1,2,3,6-tetrahydropyridine formed in step c) with a hydrogenating agent to form Compound 2.

In one embodiment, the dehydrating agent is a strong acid, preferably sulfuric acid. In one embodiment, the dehydrating agent is a strong acid. In another embodiment, the dehydration agent is sulfuric acid. In another embodiment, the oxidizing agent is a peroxide. In another embodiment, the oxidizing agent is hydrogen peroxide. In another embodiment, the hydrogenating agent is hydrogen.

This invention also provides a process for preparing Compound 3 comprising the steps of:
a) reacting 3-bromo thiophenol and 1,4-dibromobutane to form 1,4-bis((3-bromophenyl)thio)butane,
b) oxidizing the 1,4-bis((3-bromophenyl)thio)butane formed in step a) with an oxidizing agent to form 1,4-bis((3-bromophenyl)sulfonyl)butane,
c) reacting 4-pyridinylboronic acid with the 1,4-bis((3-bromophenyl)sulfonyl)butane formed in step b) to obtain 1,4-bis((3-(pyridin-4-yl)phenyl)sulfonyl)butane, d) reacting 1-iodopropane with 1,4-bis((3-(pyridin-4-yl)phenyl)sulfonyl)butane formed in step c) to form 4,4'-((butane-1,4-diyldisulfonyl)bis(3,1-phenylene))bis(1-propylpyridin-1-ium)iodide, e) adding a reducing agent to 4,4'-((butane-1,4-diyldisulfonyl)bis(3,1-phenylene))bis(1-propylpyridin-1-ium) iodide formed in step d) to form 1,4-bis((3-(1-propyl-1,2,3,6-tetrahydropyridin-4-yl)phenyl)sulfonyl) butane, and f) hydrogenating the 1,4-bis((3-(1-propyl-1,2,3,6-tetrahydropyridin-4-yl)phenyl)sulfonyl) butane formed in step e) with a hydrogenating agent to obtain Compound 3.

In one embodiment, the oxidizing agent is a peroxide, preferably hydrogen peroxide. In another embodiment, the oxidizing agent is a peroxide. In another embodiment, the oxidizing agent is hydrogen peroxide. In another embodiment, the reducing agent is sodium borohydride. In another embodiment, the hydrogenating agent is hydrogen.

This invention also provides a process for preparing Compound 4 comprising the steps of:

a) epoxidizing 4-(3-(methylsulfonyl)phenyl)-1-propyl-1,2,3,6-tetrahydropyridine with an epoxidizing agent to form (1S,6S)-6-(3-(methylsulfonyl)phenyl)-3-propyl-7-oxa-3-azabicyclo [4.1.0]heptane, and b) nucleophilically opening the epoxide of the (1S,6S)-6-(3-(methylsulfonyl)phenyl)-3-propyl-7-oxa-3-azabicyclo [4.1.0]heptane of step a) with a nucleophile to obtain Compound 4.

In one embodiment, the epoxidizing agent is sodium bromate. In another embodiment, the nucleophile is hydrogen.

This invention also provides a process for preparing Compound 5 comprising the step of reacting pridopidine with a peroxide to obtain Compound 5. In one embodiment, the peroxide is hydrogen peroxide.

This invention also provides a process for preparing Compound 6 comprising the step of reacting 4-(3-(methylsulfonyl)phenyl)piperidine with 1-chloro-2-methylpentane to obtain Compound 6.

This invention also provides a process for preparing Compound 7 comprising the steps of:

a) dehydrating 4-hydroxy-4-(3-(methylsulfonyl)phenyl)-1-propylpiperidin-1-ium chloride with a dehydrating agent to form 4-(3-(methylthio)phenyl)-1-propyl-1,2,3,6-tetrahydropyridin-1-ium hydrogen sulfate, b) oxidizing 4-(3-(methylthio)phenyl)-1-propyl-1,2,3,6-tetrahydropyridin-1-ium hydrogen sulfate of step b) with an oxidizing agent to form Compound 7.

In one embodiment, the dehydrating agent is a strong acid, preferably sulphuric acid. In another embodiment, the dehydrating agent is a strong acid. In another embodiment, the dehydrating agent is sulphuric acid. In another embodiment, the oxidizing agent is a peroxide, preferably hydrogen peroxide. In another embodiment, the oxidizing agent is a peroxide. In another embodiment, the oxidizing agent is hydrogen peroxide.

This invention also provides a process for testing whether a sample of a composition comprising pridopidine contains an undesirable impurity which comprises the step of determining whether the sample contains a compound having the structure:

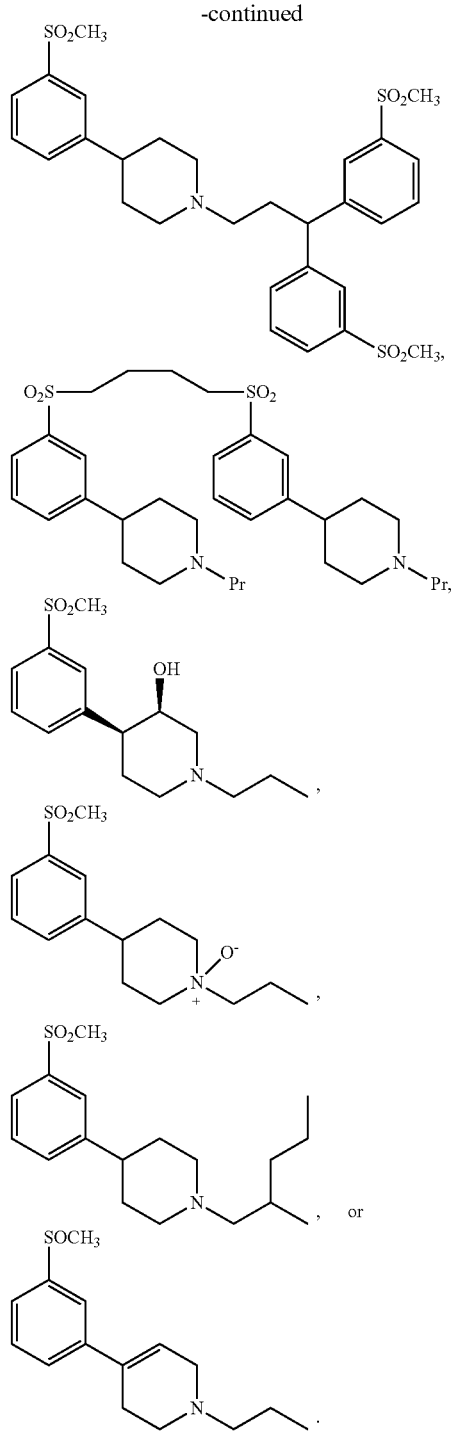

This invention also provides a process for producing a pridopidine drug product comprising obtaining a pridopidine drug substance and mixing the pridopidine drug substance with suitable excipients so as to produce the pridopidine drug product, wherein the pridopidine drug substance comprises:

i) an amount of Compound 1 in the pridopidine drug substance that is not more than 0.15 area-% Compound 1, relative to the concentration of pridopidine, or ii) an amount of Compound 2 in the pridopidine drug substance that is not more than 0.15 area-% Compound 2, relative to the concentration of pridopidine, or iii) an amount of Compound 3 in the pridopidine drug substance that is not more than 0.15 area-% Compound 3, relative to the concentration of pridopidine, or
iv) an amount of Compound 4 in the pridopidine drug substance that is not more than 0.15 area-% Compound 4, relative to the concentration of pridopidine, or
v) an amount of Compound 5 in the pridopidine drug substance that is not more than 0.15 area-% Compound 5, relative to the concentration of pridopidine, or
vi) an amount of Compound 6 in the pridopidine drug substance that is not more than 0.15 area-% Compound 6, relative to the concentration of pridopidine.

In one embodiment, the process further comprises determining the amount of the at least one of Compound 1, Compound 2, Compound 3, Compound 4, Compound 5, and Compound 6 in the pridopidine drug substance. In another embodiment, the process further comprises determining the amount of the at least two of Compound 1, Compound 2, Compound 3, Compound 4, Compound 5, and Compound 6 in the pridopidine drug substance. In another embodiment, the process further comprises determining the amount of the at least three of Compound 1, Compound 2, Compound 3, Compound 4, Compound 5, and Compound 6 in the pridopidine drug substance. In another embodiment, the process further comprises determining the amount of the at least four of Compound 1, Compound 2, Compound 3, Compound 4, Compound 5, and Compound 6 in the pridopidine drug substance. In another embodiment, the process further comprises determining the amount of the at least five of Compound 1, Compound 2, Compound 3, Compound 4, Compound 5, and Compound 6 in the pridopidine drug substance. In another embodiment, the process further comprises determining the amount of Compound 1, Compound 2, Compound 3, Compound 4, Compound 5, and Compound 6 in the pridopidine drug substance. In another embodiment, the process further comprises subjecting a sample of the pridopidine drug substance to stability testing before the step of determining the amount of the at least one of Compound 1, Compound 2, Compound 3, Compound 4, Compound 5, and Compound 6 in the pridopidine drug substance.

This invention also provides a process for producing a pridopidine drug product for commercial sale comprising obtaining a batch of pridopidine drug product that comprises:
i) an amount of Compound 1 in the batch of pridopidine drug product that is not more than 0.15 area-% Compound 1, relative to the concentration of pridopidine, or
ii) an amount of Compound 2 in the batch of pridopidine drug product that is not more than 0.15 area-% Compound 2, relative to the concentration of pridopidine, or
iii) an amount of Compound 3 in the batch of pridopidine drug product that is not more than 0.15 area-% Compound 3, relative to the concentration of pridopidine, or
iv) an amount of Compound 4 in the batch of pridopidine drug product that is not more than 0.15 area-% Compound 4, relative to the concentration of pridopidine, or
v) an amount of Compound 5 in the batch of pridopidine drug product that is not more than 0.15 area-% Compound 5, relative to the concentration of pridopidine, or
vi) an amount of Compound 6 in the batch of pridopidine drug product that is not more than 0.15 area-% Compound 6, relative to the concentration of pridopidine, and preparing the batch of pridopidine drug product for commercial sale.

In an embodiment, the process further comprises determining the amount of the at least one of Compound 1, Compound 2, Compound 3, Compound 4, Compound 5, and Compound 6 in the batch of pridopidine drug product. In another embodiment, the process further comprises determining the amount of the at least two of Compound 1, Compound 2, Compound 3, Compound 4, Compound 5, and Compound 6 in the batch of pridopidine drug product. In an embodiment, the process further comprises determining the amount of the at least three of Compound 1, Compound 2, Compound 3, Compound 4, Compound 5, and Compound 6 in the batch of pridopidine drug product. In an embodiment, the process further comprises determining the amount of the at least four of Compound 1, Compound 2, Compound 3, Compound 4, Compound 5, and Compound 6 in the batch of pridopidine drug product. In an embodiment, the process further comprises determining the amount of the at least five of Compound 1, Compound 2, Compound 3, Compound 4, Compound 5, and Compound 6 in the batch of pridopidine drug product. In an embodiment, the process further comprises determining the amount of Compound 1, Compound 2, Compound 3, Compound 4, Compound 5, and Compound 6 in the batch of pridopidine drug product. In another embodiment, the process further comprises subjecting a sample of the batch of pridopidine drug product to stability testing before determining the amount of the at least one of Compound 1, Compound 2, Compound 3, Compound 4, Compound 5, and Compound 6 in the sample of the batch of pridopidine drug product.

This invention also provides a process of distributing a pridopidine drug product comprising a pridopidine drug substance comprising,
a) obtaining the pridopidine drug product wherein the pridopidine drug substance comprises:
  i) an amount of Compound 1 in the pridopidine drug substance that is not more than 0.15 area-% Compound 1, relative to the concentration of pridopidine, or
  ii) an amount of Compound 2 in the pridopidine drug substance that is not more than 0.15 area-% Compound 2, relative to the concentration of pridopidine, or
  iii) an amount of Compound 3 in the pridopidine drug substance that is not more than 0.15 area-% Compound 3, relative to the concentration of pridopidine, or
  iv) an amount of Compound 4 in the pridopidine drug substance that is not more than 0.15 area-% Compound 4, relative to the concentration of pridopidine, or
  v) an amount of Compound 5 in the pridopidine drug substance that is not more than 0.15 area-% Compound 5, relative to the concentration of pridopidine, or
  vi) an amount of Compound 6 in the pridopidine drug substance that is not more than 0.15 area-% Compound 6, relative to the concentration of pridopidine; and
b) distributing the pridopidine drug product comprising the pridopidine drug substance.

This invention also provides a process of distributing a pridopidine drug product comprising,
a) obtaining the pridopidine drug product that comprises:
  i) an amount of Compound 1 in the pridopidine drug product that is not more than 0.15 area-% Compound 1, relative to the concentration of pridopidine, or
  ii) an amount of Compound 2 in the pridopidine drug product that is not more than 0.15 area-% Compound 2, relative to the concentration of pridopidine, or
  iii) an amount of Compound 3 in the pridopidine drug product that is not more than 0.15 area-% Compound 3, relative to the concentration of pridopidine, or
  iv) an amount of Compound 4 in the pridopidine drug product that is not more than 0.15 area-% Compound 4, relative to the concentration of pridopidine, or v) an amount of Compound 5 in the pridopidine drug product that is not more than 0.15 area-% Compound 5, relative to the concentration of pridopidine, or vi) an amount of Compound 6 in the pridopidine drug product that is not more than 0.15 area-% Compound 6, relative to the concentration of pridopidine; and b) distributing the pridopidine drug product.

This invention also provides an impurity or a salt thereof for use, as a reference standard to detect trace amounts of the impurity in a pharmaceutical composition comprising pridopidine or a pharmaceutically acceptable salt thereof, wherein the impurity is selected from the group consisting of Compound 1, Compound 2, Compound 3, Compound 4, Compound 5 and Compound 6.

This invention also provides a method of determining the concentration of an impurity in a pharmaceutical composition comprising pridopidine, the method comprising, a) preparing a sample solution from the pharmaceutical composition, b) preparing a diluent solution comprising methanol and water, c) preparing a standard solution comprising pridopidine and the diluent solution, d) preparing a resolution solution comprising pridopidine and the impurity, e) preparing a buffer solution by dissolving ammonium formate in water and adjusting to pH of 9.0±0.10 with aqueous ammonia hydroxide or formic acid, f) injecting into the HPLC the diluent solution, the resolution solution, the standard solution, and the sample solution, g) running the HPLC using ultraviolet absorption at 190-400 nm or 268 nm and a mixture of the buffer solution, methanol and water as the mobile phase, h) determining the retention time (RT) and the areas of the peaks of the impurity in the chromatograms of the sample solution, and i) performing quantitation of the impurity with respect to the corresponding peaks in the chromatograms of the sample solution, wherein the impurity is Compound 1, Compound 2, Compound 3, Compound 4, Compound 5 or Compound 6.

This invention also provides a method of determining the concentration of an impurity in a pharmaceutical composition comprising pridopidine, the method comprising a) preparing a sample solution from the pharmaceutical composition, b) preparing a diluent solution comprising methanol and water, c) preparing a standard solution comprising the impurity, d) preparing a resolution solution comprising pridopidine and the impurity, e) preparing a buffer solution by dissolving ammonium formate in water and adjusting to pH of 9.0±0.10 with aqueous ammonia hydroxide or formic acid, f) injecting into the HPLC the diluent solution, the resolution solution, the standard solution, and the sample solution, g) running the HPLC using ultraviolet absorption at 190-400 nm or 268 nm and a mixture of the buffer solution, methanol and water as the mobile phase, h) determining the retention time (RT) and the areas of the peaks of the impurity in the chromatograms of the sample solution, and i) performing quantitation of the impurity with respect to the corresponding peaks in the chromatograms of the standard solutions, wherein the impurity is Compound 1, Compound 2, Compound 3, Compound 4, Compound 5 or Compound 6.

This invention also provides a method of determining the concentration of an impurity in a pharmaceutical composition comprising pridopidine and a pharmaceutically acceptable carrier, the method comprising, a) preparing a sample solution from the pharmaceutical composition, b) preparing a diluent solution comprising methanol and water, c) preparing a standard solution comprising pridopidine and the diluent solution, d) preparing a resolution solution comprising pridopidine and the impurity, e) preparing a buffer solution by dissolving ammonium formate in water and adjusting to pH of 9.0±0.10 with aqueous ammonia hydroxide or formic acid, f) injecting into the HPLC the diluent solution, the resolution solution, the standard solution, and the sample solution, g) running the HPLC using ultraviolet absorption at 190-400 nm or 268 nm and a mixture of the buffer solution, methanol and water as the mobile phase, h) determining the retention time (RT) and the areas of the peaks of the impurity in the chromatograms of the sample solution, and i) performing quantitation of the impurity with respect to the corresponding peaks in the chromatograms of the sample solution, wherein the impurity is Compound 1, Compound 2, Compound 3, Compound 4, Compound 5 or Compound 6.

This invention also provides a method of determining the concentration of an impurity in a pharmaceutical composition comprising pridopidine and a pharmaceutically acceptable carrier, the method comprising, a) preparing a sample solution from the pharmaceutical composition, b) preparing a diluent solution comprising methanol and water, c) preparing a standard solution comprising the impurity, d) preparing a resolution solution comprising pridopidine and the impurity, e) preparing a buffer solution by dissolving ammonium formate in water and adjusting to pH of 9.0±0.10 with aqueous ammonia hydroxide or formic acid, f) injecting into the HPLC the diluent solution, the resolution solution, the standard solution, and the sample solution, g) running the HPLC using ultraviolet absorption at 190-400 nm or 268 nm and a mixture of the buffer solution, methanol and water as the mobile phase, h) determining the retention time (RT) and the areas of the peaks of the impurity in the chromatograms of the sample solution, and i) performing quantitation of the impurity with respect to the corresponding peaks in the chromatograms of the standard solutions, wherein the impurity is Compound 1, Compound 2, Compound 3, Compound 4, Compound 5 or Compound 6.

This invention also provides a method of treating a subject afflicted with a neurodegenerative disease or a neurodegenerative disorder comprising administering to the subject the pharmaceutical composition.

This invention also provides a method of treating a subject afflicted with Huntington's disease comprising administering to the subject the pharmaceutical composition.

This invention also provides a process for validating a batch of a pharmaceutical product containing pridopidine or a pharmaceutically acceptable salt thereof and a pharmaceutically acceptable carrier for distribution comprising:
a) determining the amount of at least one of Compound 1, Compound 2, Compound 3, Compound 4, Compound 5, and Compound 6; and
b) validating the batch for distribution only if
  i) the batch is determined to have not more than 0.15 area-% Compound 1, relative to the concentration of pridopidine, or
  ii) the batch is determined to have not more than 0.15 area-% Compound 2, relative to the concentration of pridopidine, or
  iii) the batch is determined to have not more than 0.15 area-% Compound 3, relative to the concentration of pridopidine, or
  iv) the batch is determined to have not more than 0.15 area-% Compound 4, relative to the concentration of pridopidine, or
  v) the batch is determined to have not more than 0.15 area-% Compound 5, relative to the concentration of pridopidine, or
  vi) the batch is determined to have not more than 0.15 area-% Compound 6, relative to the concentration of pridopidine.

This invention also provides a process for preparing a validated pharmaceutical composition comprising pridopidine comprising:
a) obtaining a batch of pridopidine drug substance;
b) determining the amount of at least one of Compound 1, Compound 2, Compound 3, Compound 4, Compound 5, and Compound 6; and
c) preparing the pharmaceutical composition from the batch only if
  i) the batch is determined to have not more than 0.15% Compound 1, relative to the concentration of pridopidine, or
  ii) the batch is determined to have not more than 0.15% Compound 2, relative to the concentration of pridopidine, or
  iii) the batch is determined to have not more than 0.15% Compound 3, relative to the concentration of pridopidine, or
  iv) the batch is determined to have not more than 0.15% Compound 4, relative to the concentration of pridopidine, or
  v) the batch is determined to have not more than 0.15% Compound 5, relative to the concentration of pridopidine, or
  vi) the batch is determined to have not more than 0.15% Compound 6, relative to the concentration of pridopidine.

This invention also provides a process for preparing a pharmaceutical composition comprising pridopidine, comprising
a) obtaining a batch of pridopidine drug product;
b) performing stability testing with a sample of the batch;
c) determining the total amount of at least one of Compound 1, Compound 2, Compound 3, Compound 4, Compound 5, and Compound 6 in the sample of the batch after stability testing by an HPLC method; and
d) preparing the pharmaceutical composition from the batch after stability testing if the sample of the batch after stability testing contains:
  i) not more than 0.15% Compound 1, relative to the concentration of pridopidine, or
  ii) not more than 0.15% Compound 2, relative to the concentration of pridopidine, or
  iii) not more than 0.15% Compound 3, relative to the concentration of pridopidine, or
  iv) not more than 0.150/% Compound 4, relative to the concentration of pridopidine, or
  v) not more than 0.15% Compound 5, relative to the concentration of pridopidine, or
  vi) not more than 0.15% Compound 6, relative to the concentration of pridopidine.

In an embodiment, the process further comprising step e) distributing the batch if in step d) the batch is validated for distribution.

This invention also provides an isolated compound having the structure:

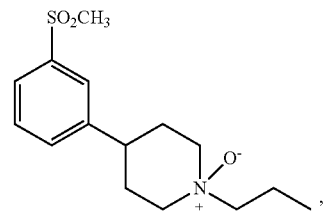

or a salt thereof.

Each embodiment disclosed herein is contemplated as being applicable to each of the other disclosed embodiments. Thus, all combinations of the various elements described herein are within the scope of the invention.

For example, the elements recited in the packaging and pharmaceutical composition embodiments can be used in the method and use embodiments described herein.

TERMS

As used herein, and unless stated otherwise, each of the following terms shall have the definition set forth below.

As used herein, "pridiopidine" means pridopidine base or a pharmaceutically acceptable salt thereof, including pridopidine hydrochloride. Preferably, in any embodiments of the invention as described herein, the pridopidine is in the form of its hydrochloride salt.

As used herein, "drug substance" refers to the active ingredient in a drug product or to the composition containing the active ingredient before it is formulated into in a drug product, which provides pharmacological activity or other direct effect in the diagnosis, cure, mitigation, treatment, or prevention of disease, or to affect the structure or any function of the body of man or animals.

As used herein, "drug product" refers to the formulated or finished dosage form containing the drug substance as well as at least one pharmaceutically acceptable carrier.

As used herein, an "isolated" compound is a compound isolated from the crude reaction mixture following an affirmative act of isolation. The act of isolation involves separating the compound from the other known components of the crude reaction mixture, with some impurities, unknown side products and residual amounts of the other known components of the crude reaction mixture permitted to remain. Purification is an example of an affirmative act of isolation.

As used herein, "stability testing" refers to tests conducted at specific time intervals and various environmental conditions (e.g., temperature and humidity) to see if and to what extent a drug product degrades over its designated shelf life time. The specific conditions and time of the tests are such that they accelerate the conditions the drug product is expected to encounter over its shelf life. For example, detailed requirements of stability testing for finished pharmaceuticals are codified in 21 C.F.R § 211.166, the entire content of which is hereby incorporated by reference.

As used herein, "about" in the context of a numerical value or range means±10% of the numerical value or range recited.

As used herein, "approximately" in the context of a numerical value or range means±5% of the numerical value or range recited or claimed.

As used herein, an "amount" of a compound as measured in milligrams refers to the milligrams of compound present in a preparation, regardless of the form of the preparation. An "amount of compound which is 40 mg" means the amount of the compound in a preparation is 40 mg, regardless of the form of the preparation. Thus, when in the form with a carrier, the weight of the carrier necessary to provide a dose of 40 mg compound would be greater than 40 mg due to the presence of the carrier.

As used herein, "treating" and "treatment" encompasses, e.g., inducing inhibition, regression, or stasis of a disease, disorder or condition, or ameliorating or alleviating a symptom of a disease, disorder or condition. "Ameliorating" or "alleviating" a condition or state as used herein shall mean to relieve or lessen the symptoms of that condition or state. "Inhibition" of disease progression or disease complication in a subject as used herein means preventing or reducing the disease progression and/or disease complication in the subject.

"Administering to the subject" means the giving of, dispensing of, or application of medicines, drugs, or remedies to a subject to relieve, cure, or reduce the symptoms associated with a condition, e.g., a pathological condition.

The drug substance of the present invention, e.g., pridopidine hydrochloride, may be administered in admixture with suitable pharmaceutical diluents, extenders, excipients, or carriers (collectively referred to herein as a pharmaceutically acceptable carrier) suitably selected with respect to the intended form of administration and as consistent with conventional pharmaceutical practices. Capsules or tablets may contain suitable binders, lubricants, disintegrating agents, diluents, coloring agents, flow-inducing agents, and melting agents.

A dosage unit of the compounds used in the method of the present invention may comprise a single compound or mixtures thereof with additional therapeutic agents.

A "dose" or "dosage unit" of pridopidine as measured in milligrams refers to the milligrams of pridopidine hydrochloride present in a preparation, regardless of the form of the preparation. A dosage unit may comprise a single compound or mixtures of compounds thereof. A dosage unit can be prepared for oral dosage forms, such as tablets, capsules, pills, powders, and granules. For example, the "dose" or "dosage unit" of priopidine may be 22.5, 45, or 67.5 mg.

As used herein, a "pharmaceutically acceptable" component is one that is suitable for use with humans and/or animals without undue adverse side effects (such as toxicity, irritation, and allergic response) commensurate with a reasonable benefit/risk ratio.

The subject invention is also intended to include all isotopes of atoms occurring on the compounds disclosed herein, including impurities. Isotopes include those atoms having the same atomic number but different mass numbers. By way of general example and without limitation, isotopes of hydrogen include tritium and deuterium. Isotopes of carbon include C-13 and C-14.

As used herein, "detection limit" for an analytical method used in screening or testing for the presence of a compound in a sample is a threshold under which the compound in a sample cannot be detected by the analytical method used. The detection limits of a given HPLC method for detecting an impurity in a sample containing pridopidine may vary based on the method and the impurity or impurities being detected. For example, the detection limit of the typical HPLC method for detecting Compounds 1, 2, 4, 5 and 6 is 0.01 area-% and the detecting limit for detecting Compound 3 is 0.03 area-%.

As used herein, "quantitation limit" for an analytical method used in screening or testing for the presence of a compound in a sample is a threshold under which the compound in a sample cannot be quantified by the analytical method used. The quantitation limits of a given HPLC method for detecting an impurity in a sample containing pridopidine may vary based on the impurity or impurities being detected. For example, the quantitation limit of the typical HPLC method for quantifying Compounds 1, 4, 5, and 6 is 0.04 area-% and the quantitation limit for Compound 3 is 0.05 area-%. The quantitation limit for Compound 2 is 0.05 area-%.

A characteristic of a compound refers to any quality that a compound exhibits, e.g., peaks or retention times, as determined by 1H nuclear magnetic spectroscopy, mass spectroscopy, infrared, ultraviolet or fluorescence spectrophotometry, gas chromatography, thin layer chromatography, high performance liquid chromatography, elemental analysis, Ames test, dissolution, stability and any other quality that can be determined by an analytical method. Once the characteristics of a compound are known, the information can be used to, for example, screen or test for the presence of the compound in a sample.

As used herein, "NMT" means no more than. As used herein, "LT" means less than.

The amount of impurities are measured by reverse phase HPLC unless otherwise specified.

As used herein, the term "effective amount" refers to the quantity of a component that is sufficient to yield a desired therapeutic response without undue adverse side effects (such as toxicity, irritation, or allergic response) commensurate with a reasonable benefit/risk ratio when used in the manner of this invention, i.e. a therapeutically effective amount. The specific effective amount will vary with such factors as the particular condition being treated, the physical condition of the patient, the type of mammal being treated, the duration of the treatment, the nature of concurrent therapy (if any), and the specific formulations employed and the structure of the compounds or its derivatives.

As used herein, "preparing drug product for commercial sale" means an activity undertaken in preparation for commercial sale. Examples include, but are not limited to, coloring, coding, stamping, packaging the drug product.

It is understood that where a parameter range is provided, all integers within that range, and tenths thereof, are also provided by the invention. For example, "20-40 mg" includes 20.0 mg, 20.1 mg, 20.2 mg, 20.3 mg, etc. up to 40.0 mg.

Pharmaceutically Acceptable Salts

The active compounds for use according to the invention may be provided in any form suitable for the intended administration. Suitable forms include pharmaceutically (i.e. physiologically) acceptable salts, and pre- or prodrug forms of the compound of the invention.

Examples of pharmaceutically acceptable addition salts include, without limitation, the non-toxic inorganic and organic acid addition salts such as the hydrochloride, the hydrobromide, the nitrate, the perchlorate, the phosphate, the sulphate, the formate, the acetate, the aconate, the ascorbate, the benzenesulphonate, the benzoate, the cinnamate, the citrate, the embonate, the enantate, the fumarate, the glutamate, the glycolate, the lactate, the maleate, the malonate, the mandelate, the methanesulphonate, the naphthalene-2-sulphonate, the phthalate, the salicylate, the sorbate, the stearate, the succinate, the tartrate, the toluene-p-sulphonate, and the like. Such salts may be formed by procedures well known and described in the art.

Pharmaceutical Compositions

While the compounds for use according to the invention may be administered in the form of the raw compound, it is preferred to introduce the active ingredients, optionally in the form of physiologically acceptable salts, in a pharmaceutical composition together with one or more adjuvants, excipients, carriers, buffers, diluents, and/or other customary pharmaceutical auxiliaries.

In an embodiment, the invention provides pharmaceutical compositions comprising the active compounds or pharmaceutically acceptable salts or derivatives thereof, together with one or more pharmaceutically acceptable carriers therefore, and, optionally, other therapeutic and/or prophylactic ingredients know and used in the art. The carrier(s) must be "acceptable" in the sense of being compatible with the other ingredients of the formulation and not harmful to the recipient thereof.

Table 1 shows the structures of Compounds 1-8.

TABLE 1

| Compound | | Structure | |
|---|---|---|---|
| Compound 1 | Potential Impurity in pridopidine. | 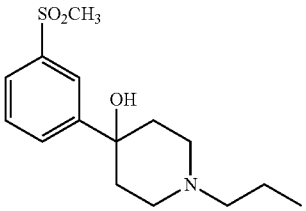 [SMILES: CCCN1CCC(O)(c2cccc(S(C)(=O)=O)c2)CC1] | 4-(3-(methylsulfonyl)phenyl)-1-propylpiperidin-4-ol |
| Compound 2 | Potential impurity of pridopidine. | 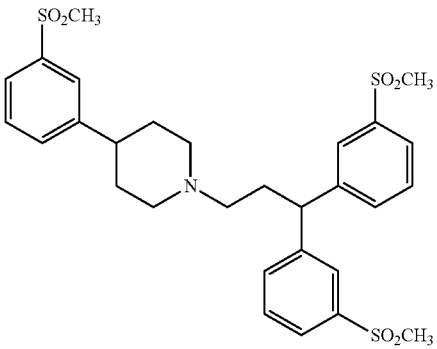 [SMILES: CS(=O)(=O)c1cccc(C2CCN(CCC(c3cccc(S(C)(=O)=O)c3)c3cccc(S(C)(=O)=O)c3)CC2)c1] | 1-(3,3-bis(3-(methylsulfonyl)phenyl)propyl)-4-(3-(methylsulfonyl)phenyl)piperidone |
| Compound 3 | Potential impurity in pridopidine. | 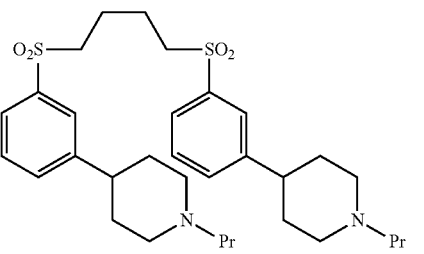 | 1,4-bis((3-(1-propylpiperidin-4-yl)phenyl)sulfonyl)butane |
| Compound 4 | Potential impurity in pridopidine. | 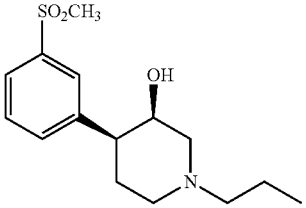 [SMILES: CCCN1CC[C@@H](c2cccc(S(C)(=O)=O)c2)[C@@H](O)C1] | (3R,4S)-4-(3-(methylsulfonyl)phenyl)-1-propylpiperidin-3-ol |

TABLE 1-continued

| Compound | | Structure | Name |
|---|---|---|---|
| Compound 5 | Potential impurity in pridopidine. | SO₂CH₃ phenyl-piperidine with N⁺-O⁻ and propyl | 4-(3-(methylsulfonyl)phenyl)-1-propylpiperidine 1-oxide |
| Compound 6 | | SO₂CH₃ phenyl-piperidine with 2-methylpentyl N-substituent | 1-(2-methylpentyl)-4-(3-(methylsulfonyl)phenyl)piperidine |
| Compound 7 | | SOCH₃ phenyl-tetrahydropyridine with N-propyl | 4-(3-(methylsulfinyl)phenyl)-1-propyl-1,2,3,6-tetrahydropyridine |
| Compound 8 | | SO₂CH₃ phenyl-tetrahydropyridine with N-propyl | 4-(3-(methylsulfonyl)phenyl)-1-propyl-1,2,3,6-tetrahydropyridine |

This invention will be better understood by reference to the Experimental Details which follow, but those skilled in the art will readily appreciate that the specific experiments detailed are only illustrative of the invention as described more fully in the claims which follow thereafter.

EXPERIMENTAL DETAILS

Examples

Example 1—Preparation of Compound 1 (4-(3-(methylsulfonyl)phenyl)-1-propylpiperidin-4-ol)

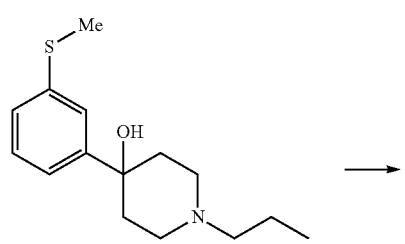

4(3-(methylthio)phenyl)-1-propylpiperidin-4-ol

→

-continued

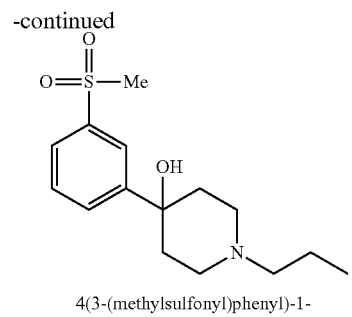

4(3-(methylsulfonyl)phenyl)-1-propylpiperidin-4-ol

To a suspension of 4-hydroxy-4-(3-(methylthio)phenyl)-1-propylpiperidin-1-ium chloride (140 g, 348 mmol) in 710 mL water were added 1.5 g sodium tungstate dihydrate, and the mixture was heated to 45° C. 102 mL of 33% $H_2O_2$ were added in 20 min at 45-55° C. The suspension dissolved after 20 mL addition. The solution was then stirred at 48-51° C. for 30 min after which HPLC showed no more starting material and two new peaks, one at RT 2.68 min (82.3%) and the other at RT 3.66 min (11.8%). After additional stirring for 2 hr and 45 min HPLC showed that the peak at RT 2.68 min decreases to 7.5% and the peak at RT 3.66 min increases to 88.5%. After another 45 min the mixture was cooled to 20° C. and into the reaction mixture were added 500 mL toluene and 150 mL-5M NaOH. After stirring for 5 min the mixture was poured into separator funnel. The solubility of the product in toluene is low. Majority of the product settled as very viscous liquid layer in the bottom. The water phase (and most of the product) was separated, toluene phase was washed successively with 5% $Na_2SO_3$ solution and with brine and dried on $MgSO_4$. The water phase was extracted with 500 mL DCM. The organic phase was washed successively with 5% $Na_2SO_3$ solution and water and was dried on $MgSO_4$. Both extracts were concentrated on a rotavapor. 500 mL of heptanes were added to both residues, and the suspensions were stirred at room temperature for 2 hrs. The precipitates were filtered, washed with heptane and dried. From the DCM extract were obtained 83.8 g of white powder, purity by HPLC 98.8%, 1H-NMR assay 97.9%. (From the toluene extract were obtained 13.7 g of white powder, purity by HPLC 98.0%).

NMR Identity Analysis of Compound 1

Compound 1

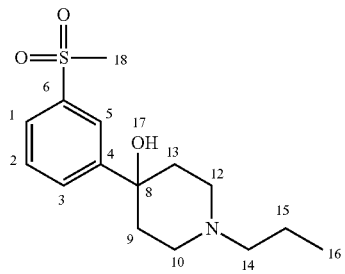

The following data in Tables 2 and 3 was determined using a sample of 78.95 mg Compound 1, a solvent of 0.55 ml DMSO-D6, 99.9 atom % D, and the instrument was a Bruker Avance III 400 MHz.

TABLE 2

Assignment of $^1H$ NMR[a,c]

| $^1H$ Shift (ppm) | Integral | Multiplicity | Assignment | COSY cross peaks | HMBC cross peaks |
|---|---|---|---|---|---|
| 8.07 | 1 | t, J = 1.7 Hz | H5 | H1[b], H3[b] | C1, C3, C4[b], C6[b], C8 |
| 7.82 | 1 | d, J = 7.9 Hz | H3 | H2, H5[b] | C1, C4[b], C5, C8 |
| 7.79 | 1 | d, J = 7.9 Hz | H1 | H2, H5[b] | C3, C4[b], C5 |
| 7.59 | 1 | t, J = 7.9 Hz | H2 | H1, H3 | C3, C4, C5, C6, C8[b] |
| 5.08 | 1 | s | H17 | — | C8, C9, C13 |
| 3.21 | 3 | s | H18 | — | C6[b] |
| 2.67 | 2 | d, J = 11.5 Hz | H10, H12 | H10, H12, H13, H9 | C8[b], C9[b], C10, C12, C13[b] |
| 2.37 | 2 | t, J = 11.6 Hz | H10, H12 | H10, H12, H13, H9 | C8[b], C9[b], C10, C12, C13[b], C14 |
| 2.28 | 2 | t, J = 7.3 Hz | H14 | H15 | C10, C12, C15, C16 |
| 1.97 | 2 | dt, J = 12.5 and 4.1 Hz | H9, H13 | H10, H12, H13, H19 | C9, C10, C12, C13 |
| 1.60 | 2 | d, J = 12.8 Hz | H9, H13 | H10, H12, H13, H9 | C8, C9, C13 |
| 1.46 | 2 | hex, J = 7.5 Hz | H15 | H14, H16 | C14, C15 |
| 0.87 | 3 | t, J = 7.5 Hz | H16 | H15 | C14, C15 |

[a]The assignment is based on the coupling pattern of the signals, coupling constants and chemical shifts.
[b]Weak signal.
[c]Spectra is calibrated by the solvent residual peak (2.5 ppm).

TABLE 3

Assignment of $^{13}C$ NMR[a,b]

| $^{13}C$ Shift (ppm) | Assignment | $^{13}C$ Shift (ppm) | Assignment |
|---|---|---|---|
| 151.9 | C4 | 60.2 | C14 |
| 140.6 | C6 | 49.0 | C10, C12 |
| 130.1 | C3 | 43.6 | C18 |
| 129.0 | C2 | 38.0 | C9, C13 |
| 124.9 | C1 | 19.8 | C15 |
| 123.3 | C5 | 12.0 | C16 |
| 70.0 | C8 | | |

[a]The assignment is based on the chemical lifts and 1H-13C couplings extracted from HSQC and HMBC experiments.
[b]Spectra is calibrated by a solvent peak (39.54 ppm)

Example 2—Preparation of Compound 2 (1-(3,3-bis(3-(methylsulfonyl)phenyl)propyl)-4-(3-(methylsulfonyl) phenyl)piperidine)

Preparation of Ethyl 3-(4-oxopiperidin-1-yl)-propanoate (Starting Material for Compound 2)

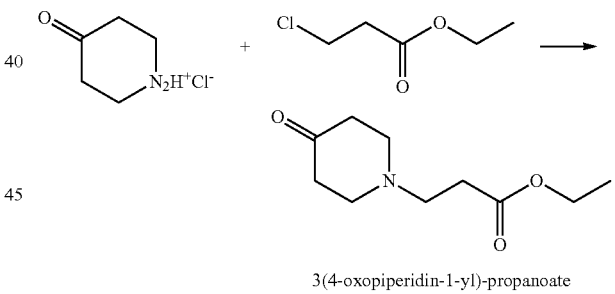

3(4-oxopiperidin-1-yl)-propanoate

Ethanol (1550 mL) was poured into a 4 L three-necked round-bottom flask equipped with over-head stirring followed by the addition of 125 g (814 mmol, 1 eq) 4-piperidone monohydrate hydrochloride and 225 g (1628 mmol, 2 eq) potassium carbonate. Ethyl 3-chloropropanoate (111 g, 1 eq) was added and the reaction mixture was stirred for 3 h after which HPLC showed that the product reached only 10% area. Another 0.5 eq of $K_2CO_3$ was added (56.2 g) and stirring continued at 24° C. After total of 45 h the product reached 860/% area (HPLC). Another 0.2 eq of $K_2CO_3$ was added and the reaction mixture was stirred for additional 4.5 h at 35° C. after which HPLC showed 96% area of the product. The mixture was filtered through a sintered glass filter, washed with 200 ml ethanol and concentrated on vacuum to 156 g yellow colored oil that was distilled under vacuum of 2 mmHg in 156° C. bath. The main fraction distilled at 120° C. to yield 97.8 g (60%) of 99.3% area (HPLC).

Preparation of 1-(3-hydroxy-3,3-bis(3-(methylthio) phenyl)propyl)-4-(3-(methylthio) phenyl)piperidin-4-ol (Compound 2, 1st Intermediate)

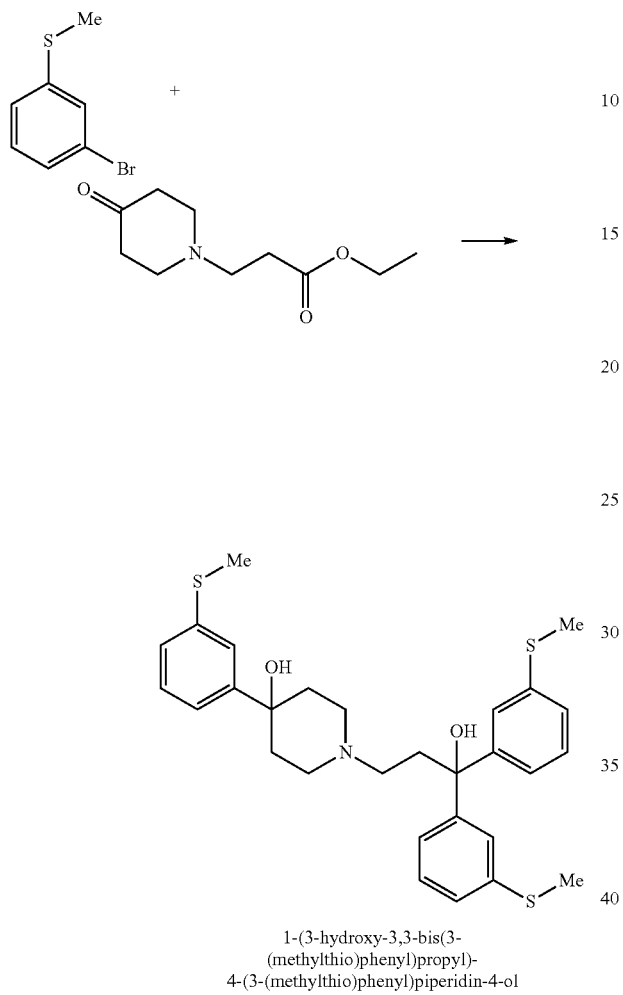

1-(3-hydroxy-3,3-bis(3-(methylthio)phenyl)propyl)-4-(3-(methylthio)phenyl)piperidin-4-ol 3-Bromothioanisole (170.3 g; 0.84 mol, 3.2 eq) and THF (700 mL) were charged to a 2 L flask, stirred under nitrogen and cooled on dry ice/acetone bath to −74° C. A solution of n-hexyllithium in hexane (2.3M; 237.4 g; 0.77 mol, 3.0 eq) was added and the reaction mixture became slightly yellowish. Stirring continued for additional 30 min at −74° C. A solution of ethyl 3-(4-oxopiperidin-1-yl)propanoate (50.2 g; 0.26 mol, 1 eq) in THF (100 mL) was added during 1 h 15 min to the reaction mixture and the stirring continued for additional 30 min at −74° C. to give a yellow clear solution. The cooling stopped and the reaction warmed to −40° C. A solution of HCl (33%; 90 g, 0.82 mol, 3.1 eq) in water (100 mL) was added dropwise for 20 min to give a light yellow emulsion in +8° C. The light yellow organic phase was separated, washed with water (3×200 mL) and extracted twice with aqueous HCl (33% HCl 40 g/300 mL water) to give lower yellow phase (234 g). The organic upper light yellow phase was evaporated up to 159 g solution and the precipitate formed during concentration was filtered to give 19.1 g yellow sticky precipitate. The precipitate was combined with the lower yellow phase, methanol (50 mL) and THF (200 mL) were added and distilled (67° C., 248 g distilled). Heptane (200 mL was added, the two liquid phase was stirred for 20 min at 40° C. and cooled to RT. The upper heptane phase was discarded and water (200 mL) was added to the viscous yellow residue water. After stirring stopped the colorless water was decanted to leave 182 g of very viscous light yellow residue (HPLC: 82% area).

Preparation of 1-(3,3-bis(3-(methylthio)phenyl)allyl)-4-(3-(methylthio)phenyl)-1,2,3,6-tetrahydropyridine (Compound 2, 2nd Intermediate)

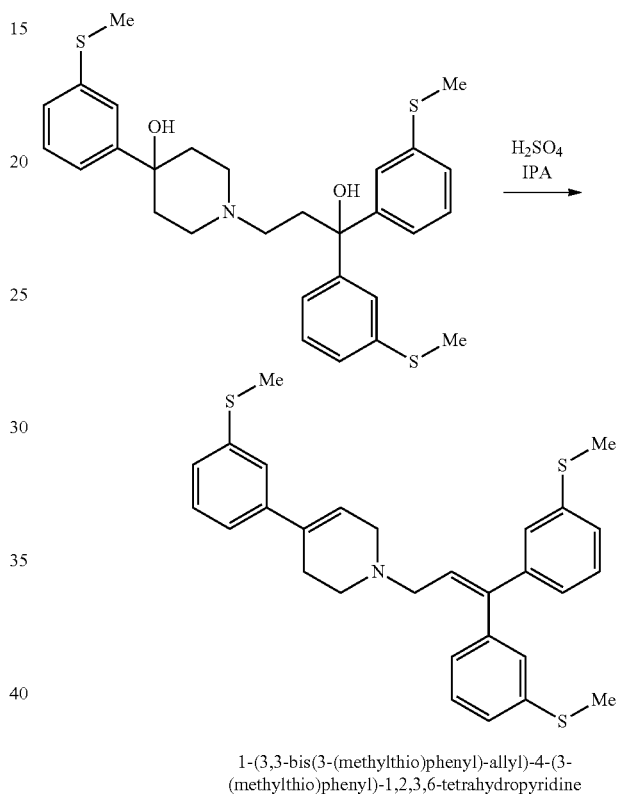

1-(3,3-bis(3-(methylthio)phenyl)-allyl)-4-(3-(methylthio)phenyl)-1,2,3,6-tetrahydropyridine Into the viscous light yellow residue was added 2-propanol (200 mL) and the reaction mixture was distilled at atmospheric pressure to give 200 mL of azeotropic distillate, leaving dark yellow oil into which methanol (50 mL), 2-propanol (350 mL) and conc. sulfuric acid (36.5 g, 0.35 mol. 1.35 eq) were added. The reaction mixture was heated for 26 hours (mixture temperature 81-84° C., vapor temperature 79° C.) and about 440 mL of distillate were collected. At the end the temperature reached 87° C. and the reaction mixture was foaming. After cooling was added toluene (100 mL) and water (200 mL) and the reaction mixture was heated to reflux (87° C.). The heating stopped and after cooling three phases were formed. The lower oily phase was washed with water (2×200 mL) and concentrated by vacuum distillation to give dark yellow viscous residue. Water (300 mL) was added and the mixture was refluxed then cooled to 40° C. and water phase was decanted to leave about 200 g orange turbid liquid (HPLC: 82% area) which was used in the next step.

41

Preparation of 1-(3,3-bis(3-(methylsulfonyl)phenyl) allyl)-4-(3-(methylsulfonyl) phenyl)-1,2,3,6-tetrahydropyridine (Compound 2, 3rd Intermediate)

42

Preparation of 1-(3,3-bis(3-(methylsulfonyl)phenyl) propyl)-4-(3-(methylsulfonyl) phenyl)piperidine (Compound 2)

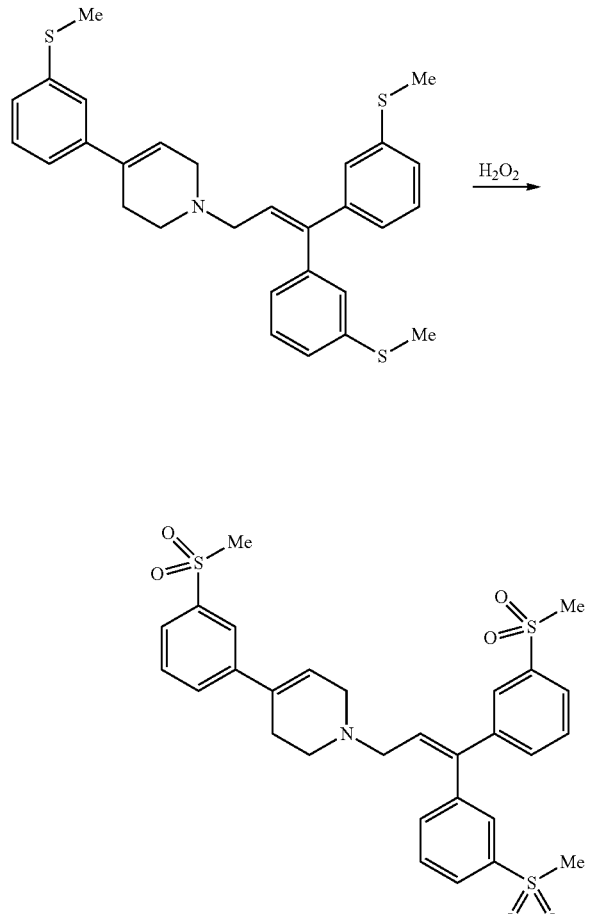

1-(3,3-bis(3-(methylsulfonyl)phenyl)-allyl)-4-(3-(methylsulfonyl)phenyl)-1,2,3,6-tetrahydropyridine

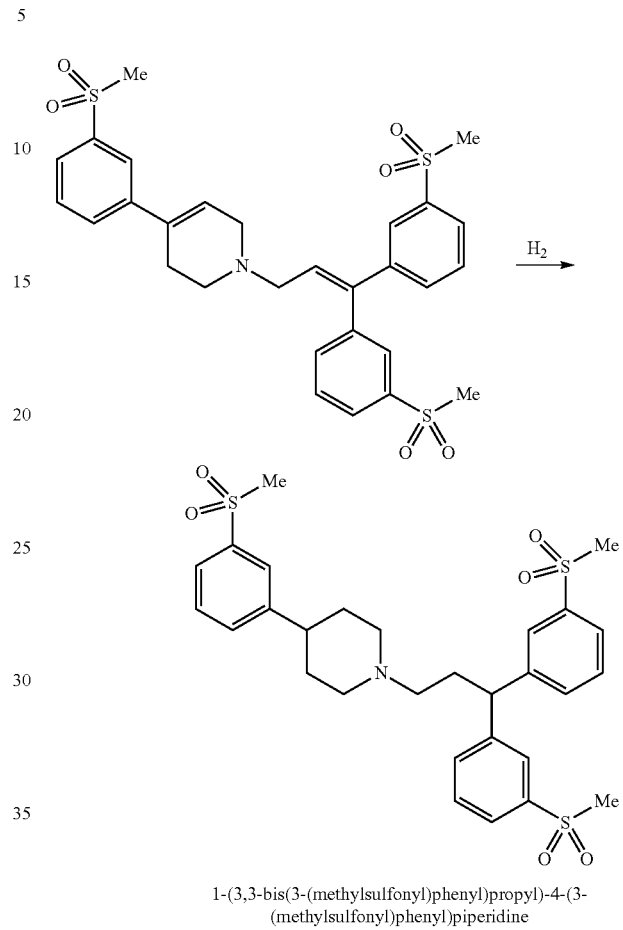

1-(3,3-bis(3-(methylsulfonyl)phenyl)propyl)-4-(3-(methylsulfonyl)phenyl)piperidine To the 200 g orange turbid liquid from the previous stage was added 500 mL water, sodium tungstate dihydrate (2 g, 6 mmol) and concentrated sulfuric acid (20 mL). The mixture was heated to 35° C. and 33% $H_2O_2$ was added drop-wise in 1 h during which the yellow viscous mass on the bottom of the flask dissolved slowly and the temperature rose up to 55° C. then decreased slowly to 42° C. The reaction mixture was heated to 50° C. for 2 hr and additional 32 g of 33% $H_2O_2$ were added. The reaction continued for another 4 h at 50° C. and additional 20 g of 33% $H_2O_2$ were added. After 2 h the reaction mixture was cooled down (25° C.) and alkalized to pH 12 by 50% NaOH solution. Water (300 mL) was added and after 20 min of mechanical stirring was discarded. Another 200 mL of water were added, stirred mechanically for 20 min and discarded to give 158.2 g highly viscous yellow mass (HPLC: 75.4% area). This mass was heated for 30 min 4 times with butanol (200 mL@95° C., 200 mL@100° C., 400 mL@100° C. and 700 mL@114° C.) and twice with acetic acid (8 mL and 250 mL@95° C.) to give light brown oil that was used in the next step (114.9 g, HPLC: 89% area).

The light brown oil from the previous stage (114.9 g, HPLC: 89% area) was added into a 2 L autoclave with 550 mL acetic acid and 10% Pd/C catalyst (25 g, 23.5 mmol). Hydrogen was introduced (120 psi) and the reaction was heated to 90° C. for 16 h. After cooling, the catalyst was filtered, washed with acetic acid (50 ml) and the clear yellowish filtrate was concentrated in vacuum to give 134 g brown viscous residue (HPLC: 82% area). Water (300 ml) was added, made alkaline (40% NaOH, pH>12) and extracted with 120 mL dichloromethane that after concentration gave 77.2 g brown sticky mass (HPLC: 83% area). The residue was treated with butanol (5×100 mL, 95° C.), cooled down and the butanol phase over an oily phase was filtered. A total of 74.9 g solid phase was resulted which was dissolved in 200 mL acetone and the clear yellow solution was evaporated to give 70.1 g dark yellow clear viscous residue. The residue was treated with heptane (2×100 mL, 95° C.) which was cooled and decanted. After evaporation in a rotavapor a pale yellow foamy solid was obtained (65.1 g, HPLC: 84% area). The solid was dissolved in 200 mL dichloromethane, 85 g silica was added and the mixture was evaporated and loaded on 1.32 Kg silica gel column which was eluted by dichloromethane with 0.5-3.0% methanol and 0.50% triethylamine. Compound 2 was isolated to give 25.8 g, HPLC: 93.2% area, 1H-NMR assay: 91.2%.

NMR Identity Analysis of Compound 2

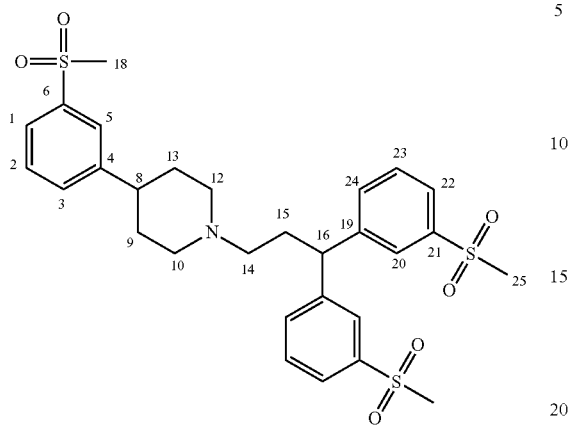

Compound 2

The following data in Tables 4 and 5 was determined using a sample of 62.03 mg Compound 2, a solvent of 0.6 ml $CDCl_3$, 99.8 atom % D, and the instrument was a Bruker Avance III 400 MHz.

TABLE 4

Assignment of $^1H$ NMR[a,c]

| $^1H$ Shift (ppm) | Integral | Multiplicity | Assignment | COSY cross peaks | HMBC cross peaks |
|---|---|---|---|---|---|
| 7.87 | 2 | s | H20 | H22[b], H24[b] | C16, C21[b], C22, C24 |
| 7.72-7.80 | 4 | m | H1, H5, H22 | H2, H23 | C1, C3, C5, C8, C20, C24 |
| 7.47-7.56 | 6 | m | H2, H3, H23, H24 | H1, H3, H20, H22 | C1, C4, C5, C6, C8, C16, C19, C21, C20, C22, C24[b] |
| 4.33 | 1 | t, J = 7.1 Hz | H16 | H15 | C14[b], C15, C19, C20, C24 |
| 3.05 | 9 | s | H18, H25 | — | — |
| 2.94 | 4 | d, J = 11.5 Hz | H10, H12 | H10, H12, H9, H13 | C8, C9[b] C10, C12, C13[b] |
| 2.53-2.62 | 1 | m | H8 | H9, H13 | C3[b], C4, C5[b], C9, C13, C10[b], C12[b] |
| 2.24-2.34 | 4 | m | H14, H15 | H16 | C10, C12, C14, C15, C16, C19 |
| 2.02 | 2 | t, J = 11.5 Hz | H10, H12 | H10, H12, H9, H13 | C8, C9[b], C10, C12, C13[b], C14 |
| 1.72-1.85 | 4 | m | H9, H13 | H8, H10, H12 | C4[b], C8, C9, C10[b], C12[b], C13 |

[a]The assignment is based on the coupling pattern of the signals, coupling constants and chemical shifts.
[b]Weak signal.
[c]Spectra is calibrated by the solvent residual peak (7.28 ppm).

TABLE 5

Assignment of $^{13}C$ NMR[a,b]

| $^{13}C$ Shift (ppm) | Assignment | $^{13}C$ Shift (ppm) | Assignment |
|---|---|---|---|
| 148.0 | C4 | 125.6 | C5 |
| 145.5 | C19 | 125.2 | C1 |
| 141.0 | C21 | 55.9 | C14 |
| 140.6 | C6 | 54.0 | C10, C12 |
| 133.2 | C24 | 48.2 | C16 |
| 132.3 | C3 | 44.51 | C18 |
| 129.9 | C23 | 44.48 | C25 |
| 129.5 | C2 | 42.4 | C8 |
| 126.7 | C20 | 32.3 | C9, C13 |
| 125.7 | C22 | 31.8 | C15 |

[a]The assignment is based on the chemical shifts and 1H-13C couplings extracted from HSQC and HMBC experiments.
[b]Spectra is calibrated by a solvent peak (77.16 ppm)

Example 3—Preparation of Compound 3 (1,4-bis ((3-(1-propylpiperidin-4-yl)phenyl)sulfonyl)butane)

Preparation of 1,4-bis((3-bromophenyl)thio)butane (Compound 3, 1st Int.)

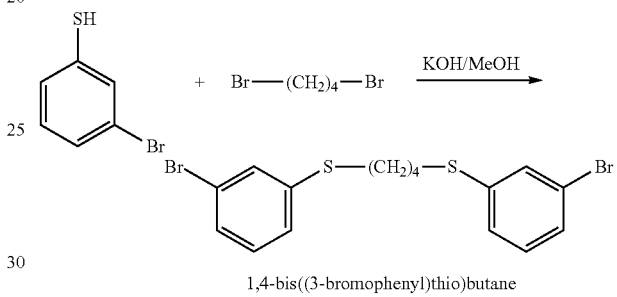

1,4-bis((3-bromophenyl)thio)butane

KOH (56.2 g) was added into methanol (1200 mL) in 15 min. The clear solution was cooled on water bath to 0° C. A solution of 3-bromo thiophenol (150.2 g, 0.79 mol) in methanol (200 mL) was added in 50 min keeping the temperature at 1-3° C. A solution of 1,4-dibromobutane (86.5 g; 0.40 mol) in methanol (150 ml) was added in 40 min to give a yellow turbid mixture. After additional 4 hours stirring the reaction mixture became white turbid and it was stirred for additional 20 h at 25° C. The suspension was filtered and washed with water (3×100 mL) and methanol (2×100 mL) to give 239 g wet white solid that was dried to 163.6 g (94.60/% yield, HPLC: 97.9%).

Preparation of 1,4-bis((3-bromophenyl)sulfonyl)butane (Compound 3, 2nd Intermediate)

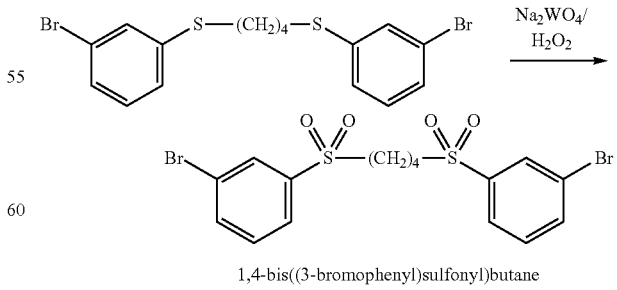

1,4-bis((3-bromophenyl)sulfonyl)butane

To a solution of 1,4-bis-(3-bromophenylthio)-butane (155.0 g, 0.358 mol) in acetic acid (1500 mL) was added sodium tungstate dihydrate (2.5 g, 0.0075 mol) and the suspension was heated on water-bath to 45° C. 50% H₂O₂ (300 mL, 5.28 mol) was added drop-wise into the reaction mixture during 3.5 h keeping the temperature at 45-55° C. The reaction mixture was kept under stirring for additional 3 h at 45° C. and 16 h at 23° C. The off white slurry was filtered, washed with water (3×200 mL) and dried on air to give 179.6 g (990/% crude yield, HPLC: 92.2% product, 7.1% by product). The crude product (175 g) was added to toluene (1400 mL) and heated to >85° C. for distillation. Distillation stopped when no more water was distilled (180 mL toluene and 10 mL water). The clear reaction mixture was allowed to cool down and was filtered after overnight stirring at ambient temperature. The bright colorless crystals were washed (150 mL toluene) and dried to give 156.1 g product (86.7% yield, HPLC: product 96.0%, main by-product 3.5%).

Preparation of 1,4-bis((3-(pyridin-4-yl)phenyl)sulfonyl)butane (Compound 3 3rd Intermediate)

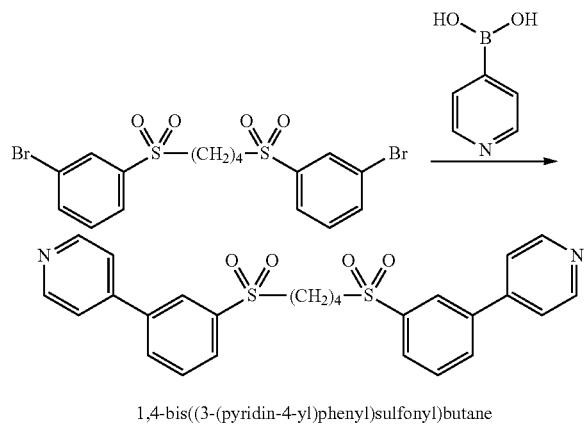

1,4-bis((3-(pyridin-4-yl)phenyl)sulfonyl)butane

To a solution of 1,4-Bis-((3-bromophenyl)-sulfonyl)-butane (92.0 g, 185 mmol) and butanol (1.0 L) was added 4-pyridinylboronic acid (75.0 g, 610 mmol), potassium carbonate (172 g, 1.24 mol) and the catalyst trans-dichlorobis-(triphenylphosphine) palladium (2.0 g; 2.8 mmol). The violet suspension was heated at stirring under nitrogen to 90-95° C. within 1 h. The reaction mixture became brown and heating continued for more 4 h. Additional 4-pyridinyl-boronic acid (3.5 g, 28 mmol) was added and the reaction mixture heated up to 100° C. for 1 h. Heating stopped, water (600 mL) was added and the temperature dropped to 60° C. The resulting dark gray suspension was stirred overnight at ambient temperature and filtered (slowly). The filter cake was washed with water (100 mL) to give 153 g wet solid which was suspended in hot acetone (2×1 L, 50° C.). The solid was then suspended with 0.5 L water at 65° C. followed by 2×1 L acetone suspension. The acetone solution were combined and concentrated on a rotavapor to give 90.3 g pale yellow solid (yield: 91%, HPLC: 91.8% area).

Preparation of 4,4'-((butane-1,4-diyldisulfonyl)bis(3,1-phenylene))bis(1-propylpyridin-1-ium)iodide (Compound 3 4th Intermediate)

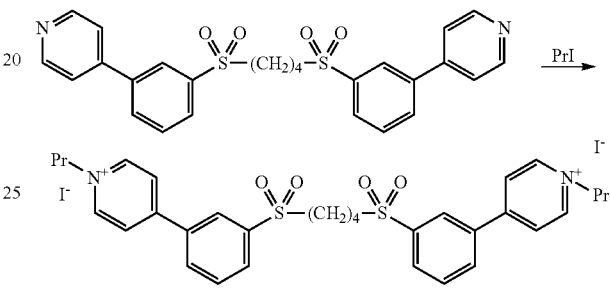

To a solution of 1,4-Bis-((3-(pyridin-4-yl)-phenyl)-sulfonyl)-butane (85.8 g, 160 mmol) and butanol (450 mL) was added 1-iodopropane (91.7 g, 540 mmol). The stirring mixture was heated up to 90-95° C. in nitrogen atmosphere and kept at this temperature for 6 hours. The dark yellow slurry was then cooled down to room temperature and kept at this temperature for 15 h. The yellow clear solution was then decanted and butanol (300 mL) was added. The mixture was heated to 70° C. where it dissolved. Heating continued to 95° C. and light brown slurry appeared. The heating was stopped and the mixture cooled down to 40° C. The yellow cloudy liquid was decanted and a dark yellow solid mass was filtered to give 173.5 g (HPLC: 84% area) which was used as is in the next step.

Preparation of 1,4-bis((3-(1-propyl-1,2,3,6-tetrahydropyridin-4-yl)phenyl)sulfonyl) butane (Compound 3, 5th Intermediate)

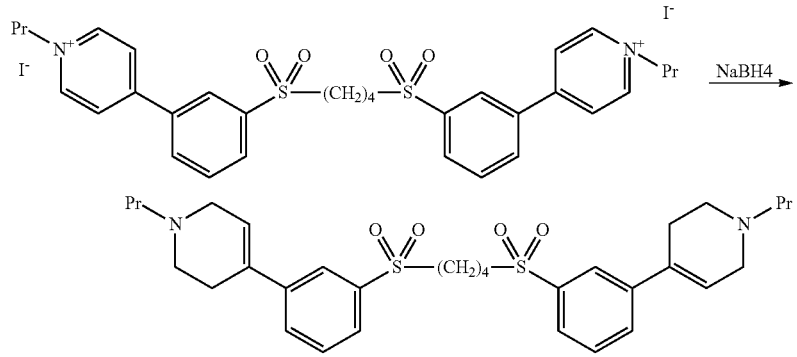

1,4-bis((3-(1-propyl-1,2,3,6-tetrahydropyridin-4-yl)phenyl)sulfonyl)butane

To the solid crude starting material (173.5 g from the previous stage) was added methanol (450 mL) and the mixture was heated to reflux to give dark yellowish red clear solution which after cooling gave two phases, the lower one weigh 150 g (HPLC: 88.4% area, yield corrected to area %: 131 g, 157 mmol). Methanol (400 mL) was added and the mixture was cooled (0° C.). Sodium borohydride (23.75 g, 624 mmol, 4 eq) was added and the reaction mixture was allowed to warm to RT and stirred for additional 9 h. The workup includes concentrating filtrates and precipitating from butanol and methanol, several slurries in butanol, extraction by hot butanol from water and finally active carbon treatment to the product dissolved in hot butanol to give 63.0 g (HPLC: 85% area) which was used as is in the next step.

Preparation of 1,4-bis((3-(1-propylpiperidine-4yl)phenyl)sulfonyl)butane (Compound 3)

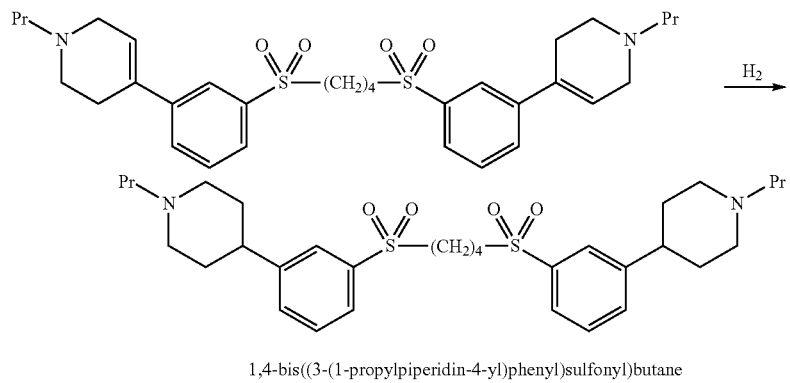

1,4-bis((3-(1-propylpiperidin-4-yl)phenyl)sulfonyl)butane

The product from the previous step (60.0 g, 51 g as HPLC is 85% area, 87 mmol) was added into an autoclave with 350 mL acetic acid. A suspension of 10% Pd/C catalyst (10 g, 9.4 mmol) in water (80 mL) was added. Air was exchange to nitrogen and then hydrogen was introduced (150 psi) and the reaction was heated to 85° C. for 6 h. After cooling the catalyst was filtered, washed with acetic acid (2×30 mL) and water (2×30 mL) and concentrated under vacuum to give 98 g of slightly brownish viscous residue. The residue was dissolved with water (200 mL), filtered (to remove traces of charcoal) and washed with 50 mL water. To the slightly brownish solution was added concentrated NaOH up to pH 13 and the mixture was stirred for 30 m. The massive precipitation was filtered to give 78.1 g slightly beige wet solid. The wet solid was mixed with water (100 mL) and toluene (300 mL), heated up to 87° C. for 30 min and the dark yellow water phase was separated. The organic phase was filtered and cooled down to 30° C. After 4 h the slurry was filtered, washed with 20 mL toluene and dried to give 40.8 g off-white solid (HPLC: 74.4% area). The solid was then suspended in toluene (260 mL) and water (40 mL) and heated up to 85° C. The colorless water phase was separated and the toluene phase was filtered, cooled down to 5° C. for 2 hr and filtered to give after drying 38.0 g off-white solid (HPLC: 81.5% area). The solid was then crystallized twice from toluene (300 mL, heating to 90° C., cooled to 3° C., filtered, washed with 30 mL toluene, dried) to give 31.2 g, HPLC: 96.9%0 area, 1H-NMR assay: 93.9%.

NMR Identity Analysis of Compound 3

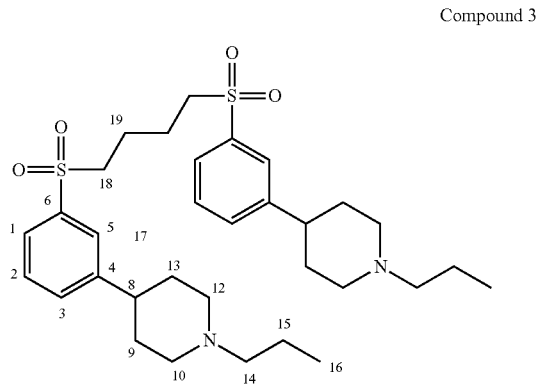 [SMILES: CCCN1CCC(c2cccc(S(=O)(=O)CCCCS(=O)(=O)c3cccc(C4CCN(CCC)CC4)c3)c2)CC1]

Compound 3

The following data in Tables 6 and 7 was determined using a sample of 47.82 mg Compound 3, a solvent of 1.0 ml DMSO-D6, 99.9 atom % D, and the instrument was a Bruker Avance III 400 MHz.

TABLE 6

Assignment of $^1$H NMR$^{a,c}$

| $^1$H Shift (ppm) | Integral | Multiplicity | Assignment | COSY cross peaks | HMBC cross peaks |
|---|---|---|---|---|---|
| 7.68-7.70 | 2 | m | H5 | H1$^b$, H3$^b$ | C1, C3, C8 |
| 7.66 | 2 | dt, J = 7.5 and 1.2 HZ | H1 | H5$^b$, H2 | C3, C5 |
| 7.63 | 2 | d, J = 7.7 Hz | H3 | H2, H5$^b$ | C1, C5, C8 |
| 7.55 | 2 | t, = 7.5 Hz | H2 | H1, H3 | C1$^b$, C3$^b$, C4, C6 |
| 3.30-3.37 | 4 | m | H18 | H19 | C19 |
| 2.95 | 4 | d, J = 11.5 Hz | H10, H12 | H10, H12, H9, H13 | C8$^b$ |
| 2.61 | 2 | t, J = 11.9 Hz | H8 | H9, H13 | — |
| 2.25 | 4 | t, J = 7.2 Hz | H14 | H15 | C10, C12, C15, C16 |
| 1.96 | 4 | t, 1 = 11.9 Hz | H10, H12 | H10, H12, H9, H13 | — |
| 1.76 | 4 | d, J = 12.6 Hz | H9, H13 | H8, H9, H10, H12, H13 | — |
| 1.62-1.71 | 4 | m | H9, H13 | H8, H9, H10, H12, H13 | C10$^b$, C12$^b$, C9$^b$, C13$^b$ |
| 1.59-1.65 | 4 | m | H19 | H18 | C19$^b$ |
| 1.43 | 4 | sextet, J = 7.3 Hz | H15 | H14, H16 | C14, C16 |
| 0.86 | 3 | t, J = 7.2 Hz | H16 | H15 | C14, C15 |

$^a$The assignment is based on the coupling pattern of the signals, coupling constants and chemical shifts. Due to the low concentration of dissolved material sonic expected HMBC signals were masked by background noise.
$^b$Weak signal.
$^c$Spectra is calibrated by the solvent residual peak (2.5 ppm).

TABLE 7

Assignment of $^{13}$C NMR$^{a,b}$

| $^{13}$C Shift (ppm) | Assignment | $^{13}$C Shift (ppm) | Assignment |
|---|---|---|---|
| 147.9 | C6 | 53.7 | C10, C12, C18 |
| 139.2 | C4 | 41.7 | C8 |
| 132.2 | C3 | 32.8 | C9, C13 |
| 129.4 | C2 | 20.7 | C19 |
| 125.7 | C5 | 19.7 | C15 |
| 125.2 | C1 | 11.9 | C16 |
| 60.2 | C14 | | |

$^a$The assignment is based on the chemical shifts and 1H-13C couplings extracted from HSQC and HMBC experiments.
$^b$Spectra is calibrated by a solvent peak (39.54 ppm).

Example 4—Preparation of Compound 4 ((3R,4S)-4-(3-(methylsulfonyl)phenyl)-1-propylpiperidin-3-ol)

Preparation of (1S,6S)-6-(3-(methylsulfonyl)phenyl)-3-propyl-7-oxa-3-azabicyclo [4.1.0]heptane

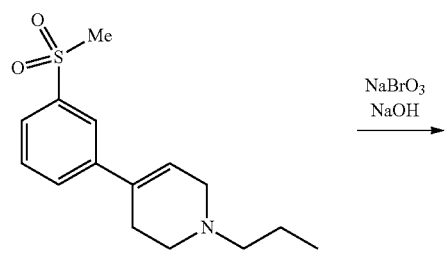

NaBrO$_3$
NaOH
→

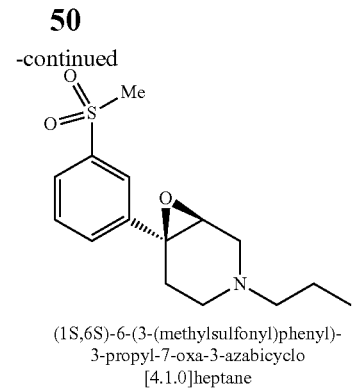

(1S,6S)-6-(3-(methylsulfonyl)phenyl)-3-propyl-7-oxa-3-azabicyclo[4.1.0]heptane

Into a 4 L reactor was added at room temperature Compound 8 (229 g, 820 mmol, 1 eq) and 2N sulfuric acid (1147 mL, 112 g sulfuric acid, 1.147 mol, 1.4 eq). The reaction light yellow mixture was stirred and sodium bromate (126 g, 836 mmol, 1.02 eq) was added. The mixture became yellow and the temperature dropped (endothermic dissolution). After 30 min the reaction temperature reached 35° C. and heated further to 40° C. for 6 h to give dark yellow solution with precipitate in the bottom of reactor. Toluene (2 L) and NaOH (24%, 546 g, 131 g NaOH, 3.28 mol, 4.0 eq) were added and the reaction mixture was vigorously stirred for 1 hour at 42° C. The reaction mixture was then poured into a 4 L separation funnel. The dark water phase was discarded and the dark red organic phase was washed with 1.1 L 50% sodium sulphite solution and 1 L 20%° brine. The organic phase was then concentrated on a rotavapor (50° C., 90-65 mbar, finally at 45 mbar) to give 111 g dark red oil with crystals in the flask. A GC analysis (5 mg red oil dissolved in 0.6 ml toluene) showed 53% area product, 29% and 5.2% area unknown peaks and 0.4% Compound 8. The product goes to the reduction in the next stage.

Preparation of (3S,4R)-4-(3-(methylsulfonyl)phenyl)-1-propylpiperidin-3-ol (Compound 4)

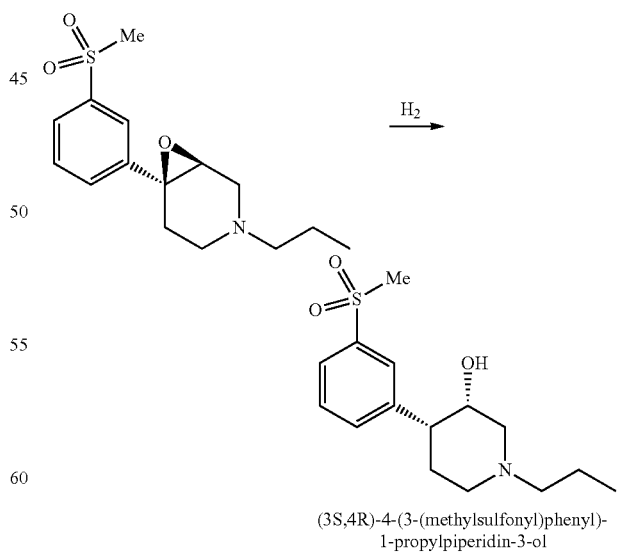

(3S,4R)-4-(3-(methylsulfonyl)phenyl)-1-propylpiperidin-3-ol

The epoxide from the previous stage (111 g of 53% GC purity, 62.0 g. 210 mmol, 1 eq) was dissolved in ethanol (1.2 L) for 1 h. The red colored mixture was poured into 2 L Parr reactor and a solution of 10% Pd/C (14.6 g, dry) in ethanol (50 mL) was added. The mixture was reacted with hydrogen (4 bar) at 30° C. for 10 hr. Pd/C was filtered through a Celite and the filtrate was concentrated in the rotavapor to give 108 g red oil (65% area product by GC). The product was added to 200 g silica gel, 0.5% triethylamine in dichloromethane were added and the mixture was concentrated and loaded on a column with 620 g silica gel. The purification was done with 0.5% triethylamine in dichloromethane to give 28 g hard residue (97.0% area by GC). The residue was heated to reflux in 34 mL dichloromethane until complete dissolution to give clear red solution which was cooled slowly with parallel removal of some solvent by nitrogen flow over the solvent. The precipitation was filtered and washed with dichloromethane (5 mL) to give 20 g white solid, HPLC: 99.0% area, 1H-NMR assay: 99.4%.

NMR Identity Analysis of Compound 4

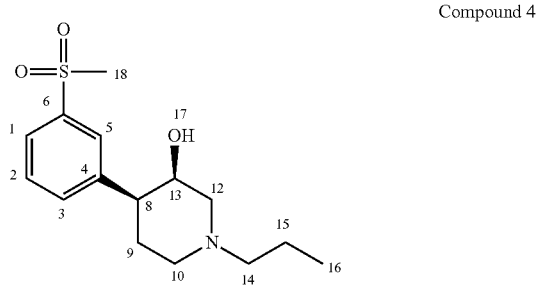 [SMILES: CCCN1CC[C@@H](c2cccc(S(C)(=O)=O)c2)[C@@H](O)C1]

Compound 4

The following data in Tables 8 and 9 was determined using a sample of 54.06 mg Compound 4, a solvent of 0.55 ml DMSO-D6, 99.9 atom % D, and the instrument was a Bruker Avance III 400 MHz.

TABLE 8

Assignment of $^1$H NMR$^{a,c}$

| $^1$H Shift (ppm) | Integral | Multiplicity | Assignment | COSY cross peaks | HMBC cross peaks |
|---|---|---|---|---|---|
| 7.85 | 1 | s | H5 | H1$^b$, H2$^b$, H3$^b$ | C1, C3, C8 |
| 7.75 | 1 | d, J = 7.9 Hz | H1 | H2, H3$^b$, H5$^b$ | C5, C3, C2$^b$ |
| 7.65 | 1 | d, J = 7.7 Hz | H3 | H2, H1$^b$, H5$^b$ | C1, C5, C8 |
| 7.55 | 1 | t, J = 7.6 Hz | H2 | H1, H3, H5$^b$ | C4, C6 |
| 4.15 | 1 | d, J = 7.5 Hz | H17 | H13 | C12$^b$, C13 |
| 3.78 | 1 | d, J = 6.6 Hz | H13 | H12$^b$, H17 | C9$^b$ |
| 3.18 | 3 | s | H18 | — | C6 |
| 2.92-2.97 | 2 | m | H10, H12 | H9, H10, H15 | C8, C10, C13$^b$ |
| 2.76 | 1 | dt, J = 13.0 and 3.3 Hz | H8 | H9 | C3$^b$, C4, C5$^b$ |
| 2.19-2.32 | 3 | m | H14, H9 | H9, H10, H15 | C10, C12, C15, C16 |
| 2.16 | 1 | d, J = 11.5 Hz | H12 | H12 | C10, C14 |
| 2.00 | 1 | t, J = 11.2 Hz | H10 | H9, H10 | C8$^b$, C12 |
| 1.54 | 1 | d, J = 12.3 Hz | H9 | H9, H10 | C13$^b$ |
| 1.46 | 2 | sextet, J = 7.3 Hz | H15 | H14, H16 | C14, C16 |
| 0.88 | 3 | t, J = 7.3 Hz | H16 | H15 | C14, C15 |

$^a$The assignment is based on the coupling pattern of the signals, coupling constants and chemical shifts.
$^b$Weak signal.
$^c$Spectra is calibrated by the solvent residual peak (2.5 ppm).

TABLE 9

Assignment of $^{13}$C NMR$^{a,b}$

| $^{13}$C Shift (ppm) | Assignment | $^{13}$C Shift (ppm) | Assignment |
|---|---|---|---|
| 145.6 | C4 | 59.8 | C14 |
| 140.4 | C6 | 53.3 | C10 |
| 133.3 | C3 | 45.6 | C8 |
| 128.8 | C2 | 43.6 | C18 |
| 126.3 | C5 | 25.2 | C9 |
| 124.4 | C1 | 19.3 | C15 |
| 67.8 | C13 | 11.9 | C16 |
| 60.1 | C12 | | |

$^a$The assignment is based on the chemical shifts and 1H-13C couplings extracted from HSQC and HMBC experiments.
$^c$Spectra is calibrated by a solvent peak (39.54 ppm)

Example 5—Preparation of Compound 5 (4-(3-(methylsulfonyl)phenyl)-1-propylpiperidine 1-oxide)

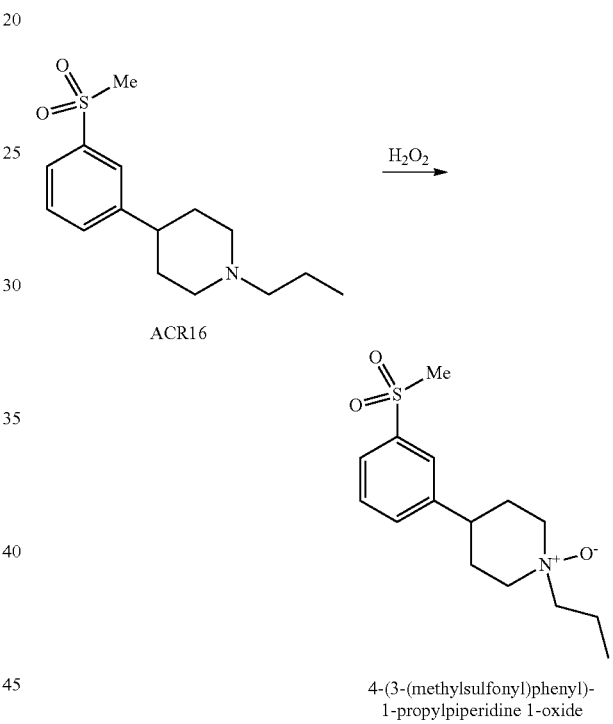

Pridopidine (50.0 g, 178 mmol, 1 eq) was dissolved in methanol (250 mL) and 33% hydrogen peroxide (20 mL, 213 mmol, 1.2 eq). The reaction mixture was heated and kept at 40° C. for 20 h. The reaction mixture was then concentrated in a rotavapor to give 71 g light-yellow oil. Water (400 mL) was added and the suspension was extracted with isopropyl acetate (150 mL) which after separation contains unreacted pridopidine while water phase contains 91% area of Compound 5 (HPLC). The product was then washed with dichloromethane (400 mL) after adjusting the water phase pH to 9 by sodium hydroxide. After phase separation the water phase was washed again with dichloromethane (200 mL) to give 100% area of Compound 5 in the water phase (HPLC). The product was then extracted from the water phase into butanol (1×400 mL, 3×200 ml) and the butanol phases were combined and concentrated in a rotavapor to give 80 g yellow oil (HPLC: 100% area of Compound 5). The oil was washed with water (150 mL) to remove salts and the water was extracted with butanol. The organic phases were combined and concentrated in a rotavapor to give 43 g of white solid which was suspended in MTBE for 1 hr, filtered and dried to give 33 g solid that was melted when standing on air. After high vacuum drying (2 mbar, 60° C., 2.5 h) 32.23 g pure Compound 5 were obtained (HPLC: 99.5% area, 1H-NMR assay: 97.4%).

NMR Identity Analysis of Compound 5

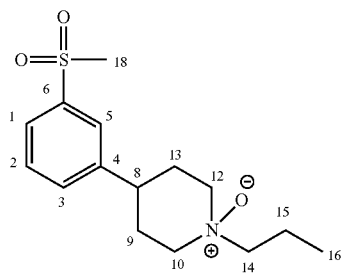

Compound 5

The following data in Tables 10 and 11 was determined using a sample of 63.06 mg Compound 5, a solvent of 1.2 ml DMSO-D6, 99.9 atom % D, and the instrument was a Bruker Avance III 400 MHz.

TABLE 10

Assignment of $^1$H NMR[a,c]

| $^1$H Shift (ppm) | Integral | Multiplicity | Assignment | COSY cross peaks | HMBC cross peaks |
|---|---|---|---|---|---|
| 7.81 | 1 | bs | H5 | — | C1, C3, C8 |
| 7.78-7.80 | 1 | m | H1 | H2 | C3, C5 |
| 7.63-7.66 | 1 | m | H3 | H2 | C1, C4[b], C5, C8 |
| 7.59-7.63 | 1 | m | H2 | H1, H3 | C1[b], C4, C6 |
| 3.27 | 2 | t, J = 11.2 Hz | H10, H12 | H9, H10, H12, H13 | C8, C9, C13 |
| 3.23 | 3 | s | H18 | — | C1[b], C6 |
| 3.07-3.11 | 2 | m | H14 | H15 | C10, C12, C15, C16 |
| 3.02 | 2 | d, d = 13.1 Hz | H10, H12 | H9, H10, H12, H13 | C8, C9[b], C13[b] |
| 2.81 | 1 | t, J = 12.7 Hz | H8 | H9, H13 | C3b, C4, C5b, C9, C13, C10, C12 |
| 2.39-2.50 | 2 | m | | H9, H13 | H8, H9, H10, H12, H13 | C4, C8, C10, C12, C9, C13 |
| 1.79-1.89 | 2 | m | H15 | H14, H16 | C14, C16 |
| 1.64 | 7 | d, J = 12.8 Hz | H9, H13 | H8[b], H9, H10[b], H12[b], H13 | C4b, C8b, C10b, C12b |
| 0.90 | 3 | t, J = 7.5Hz | H16 | H15 | C14, C15 |

[a]The assignment is based on the coupling pattern of the signals, coupling constants and chemical shifts.
[b]Weak signal.
[c]Spectra is calibrated by the solvent residual peak (2.5 ppm).

TABLE 11

Assignment of $^{13}$C NMR[a,b]

| $^{13}$C Shift (ppm) | Assignment | $^{13}$C Shift (ppm) | Assignment |
|---|---|---|---|
| 146.9 | C4 | 63.4 | C10, C12 |
| 141.0 | C6 | 43.5 | C18 |
| 132.1 | C3 | 39.4 | C8 |
| 129.6 | C2 | 27.3 | C9, C13 |
| 125.0 | C1 | 15.1 | C15 |
| 124.9 | C5 | 11.3 | C16 |
| 72.4 | C14 | | |

[a]The assignment is based on the chemical shifts and 1H-13C couplings extracted from HSQC and HMBC experiments.
[b]Spectra is calibrated by a solvent peak (39.54 ppm)

Example 6—Preparation of Compound 6 (1-(2-methylpentyl)-4-(3-(methylsulfonyl)phenyl)piperidine)

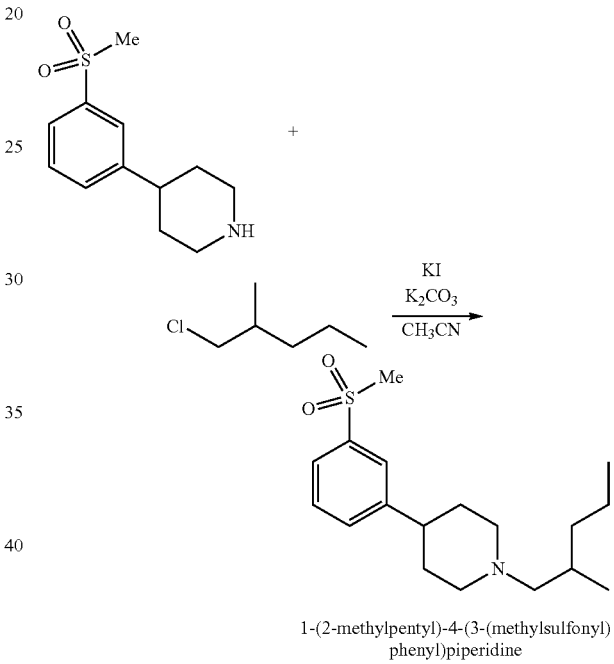

1-(2-methylpentyl)-4-(3-(methylsulfonyl)phenyl)piperidine

Into a 1 L autoclave was added KI (28.4 g, 171 mmol 1 eq) and potassium carbonate (47.4 g, 343 mmol, 2 eq). 4-(3-(methylsulfonyl)phenyl)piperidine (41 g, 171 mmol, 1 eq) was dissolved in acetonitrile (420 mL) and the mixture was added into the autoclave followed by 1-chloro-2-methylpentane (25.8 mL, 188 mmol, 1.1 eq). The autoclave was closed and the reaction mixture was heated under nitrogen atmosphere to 120° C. for 30 hr. The reaction mixture was cooled down and filtered. The cake was washed with acetonitrile and the filtrate was concentrated in vacuum to give 70 g crude product with the following HPLC areas: 60% of Compound 6, 1% of 4-(3-(methylsulfonyl)phenyl) piperidine and 10% of a by-product. The crude product was dissolved in toluene (350 ml) and about 20 g solid material was filtered. The toluene phase was washed with water (200 mL) and concentrated in a rotavapor to give 35.5 g (73% area of product by HPLC). The residue was then dissolved in ethyl acetate (180 mL) and cooled on ice bath. Into the reaction mixture was then added 33 mL of 18% HCl solution in ethyl acetate in 1 hr and the mixture was stirred for an additional 1 h. The precipitate that was formed was then filtered, washed with ethyl acetate and dried to give 36.3 g white solid (HPLC: 94% area. The product was recrystallized by dissolving in methanol (290 mL), heating to 70° C., adding ethyl acetate (400 mL) and cooling to room temperature. The precipitate was filtered, washed with ethyl acetate (60 mL) and dried in vacuum at 50° C. to give 28.3 g Compound 6 (HPLC: 99.5% area, 1H-NMR assay: 99.6%).

NMR Identity Analysis of Compound 6

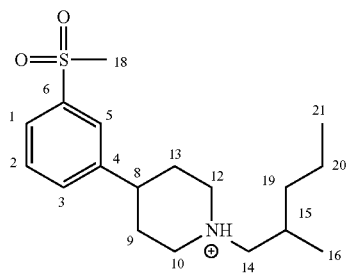

Compound 6

The following data in Tables 12 and 13 was determined using a sample of 33.93 mg Compound 6, a solvent of 8 ml DMSO-D6, 99.9 atom % D, and the instrument was a Bruker Avance III 400 MHz. Two conformers (ca 10:1) at room temperature are observed. Due to the overlap of proton signals of the major and minor conformers and relatively weak signal of the minor isomer in 2D spectra only some of the peaks of minor isomer on 1H spectra and corresponding 1H-1H COSY cross peaks are given. Due to the low solubility of the material in D6-DMSO some of the expected HMBC signals are masked by background noise.

TABLE 12

Assignment of $^1$H NMR$^{a,c}$

| $^1$H Shift (ppm) | Integral | Multiplicity | Assignment | COSY cross peaks | HMBC cross peaks |
|---|---|---|---|---|---|
| 9.88 | 1 | bs | NH | H10, H12, H14 | — |
| 7.79-7.84 | 2 | m | H1, H5 | H2, H3 | C1, C3, C5, C8 |
| 7.62-7.66 | 2 | m | H2, H3 | H1, H15 | C1, C4, C5, C6, C8$^b$ |
| 3.53-3.63 | 2 | m | H10, H12 | H10, H12 | — |
| 3.23 | 3 | s | H18 | — | C5$^b$, C6 |
| 2.87-3.11 | 5 | m | H8, H10, H12, H14 | H9, H10, H12, H13, H15 | C9, C12$^b$, C13, C15, C16, C19$^b$ |
| 2.17-2.34 | 2 | m | H9, H13 | H8, H9, H10, H12, H13 | — |
| 1.94-2.02 | 3 | m | H9, H13, H15 | H8, H9, H10, H12, | — |
| 1.22-1.45 | 3 | m | H19, H20 | H15, H19, H20, H21 | C20 |
| 1.10-1.21 | 1 | m | H19 | H15, H20 | C16, C20, C21 |
| 1.02 | 3 | d, J = 6.7 Hz | H16 | H15 | C14, C15, C19 |
| 0.90 | 3 | t, J = 6.8 Hz | H21 | H20 | C19, C20 |
| Minor isomer | | | | | |
| 10.14 | 1 | bs | NH | H10, H12 | — |
| 7.88 | 1 | s | H5 | — | — |
| 7.75 | 1 | d, J = 8.5 Hz | H1 | H2 | — |

TABLE 12-continued

Assignment of $^1$H NMR$^{a,c}$

| $^1$H Shift (ppm) | Integral | Multiplicity | Assignment | COSY cross peaks | HMBC cross peaks |
|---|---|---|---|---|---|
| 3.24-3.31 | 4 | m | H10, H12 | H9, H13 | — |
| 1.86-1.84 | 3 | m | H9, H13, H15 | H10, H12, H16 | — |

$^a$The assignment is based on the coupling pattern of the signals, coupling constants and chemical shifts.
$^b$Weak signal.
$^c$Spectra is calibrated by the solvent residual peak (2.5 ppm).

TABLE 13

Assignment of $^{13}$C NMR$^{a,b}$

| $^{13}$C Shift (ppm) | Assignment | $^{13}$C Shift (ppm) | Assignment |
|---|---|---|---|
| 145.9 | C4 | 43.5 | C18 |
| 141.1 | C6 | 38.5 | C8 |
| 131.9 | C3 | 36.4 | C19 |
| 129.8 | C2 | 29.20 and 29.24 | C9, C13 |
| 125.3 | C1 | 27.5 | C15 |
| 124.9 | C5 | 19.1 | C20 |
| 62.5 | C14 | 18.0 | C16 |
| 53.1 | C10 | 14.0 | C21 |
| 51.8 | C12 | | |

$^a$The assignment is based on the chemical shifts and 1H-13C couplings extracted from HSQC and HMBC experiments.
$^b$Spectra is calibrated by a solvent peak (39.54 ppm)

Example 7—Preparation of Compound 7 (4-(3-(methylsulfinyl)phenyl)-1-propyl-1,2,3,6-tetrahydropyridine)

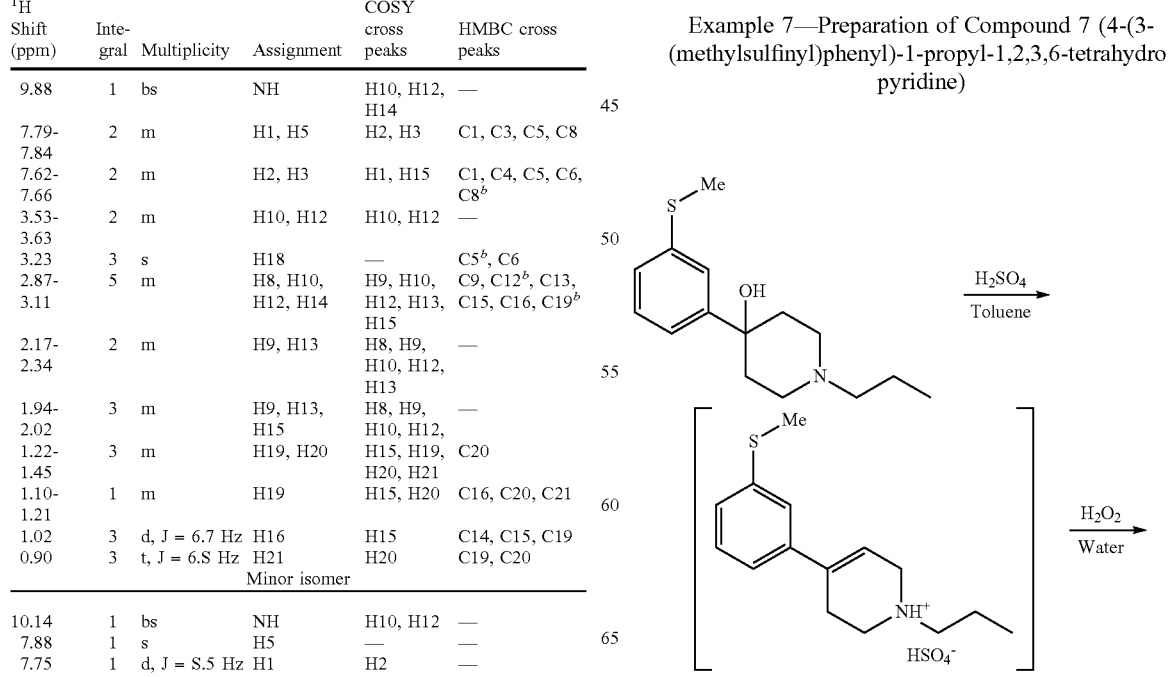

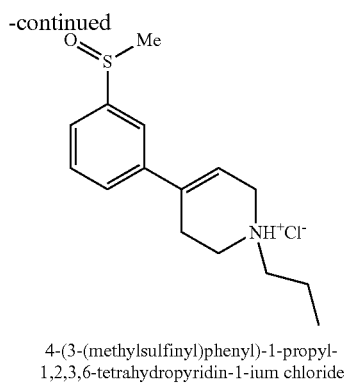

4-(3-(methylsulfinyl)phenyl)-1-propyl-1,2,3,6-tetrahydropyridin-1-ium chloride

Sulfuric acid (42.23 g, 0.431 mol, 1 eq) was added to a mixture of 4-hydroxy-4-(3-(methylsulfonyl)phenyl)-1-propylpiperidin-1-ium chloride (130 g, 0.431 mo, 1 eq) and toluene (650 mL) at room temperature. The resulting two-phase solution was refluxed for 1 hour and HPLC showed that the product reached 95% area. The reaction mixture was cooled down to 20° C. and the toluene phase was decanted to give viscous residue that was diluted with water (600 mL) and neutralized with 2N NaOH to pH-4.2. Hydrogen peroxide (50%, 32.21 g, 0.474 mol, 1.1 eq) was added dropwise to the water phase and the mixture was stirred at 60° C. for 1 h after which the product reached 96% area (HPLC).

Toluene (600 mL) was added to the reaction mixture and made basic first with 25% NaOH (60 g) and finally with 10% NaOH up to pH 12. The phases were separated and the water phase was re-extracted with toluene (2×100 mL). The combined toluene phases were washed with 5% sodium sulfite (150 mL), brine (150 mL) and water (150 mL). The toluene phase was then concentrated under vacuum on a rotavapor to give 111.3 g oil (HPLC area: 96.6%). Methanol (50 mL) was added to the residue and it was filtered and cooled down on ice batch. Dry HCl in ethyl acetate was added up to pH 1-2 (120 mL) and 100 mL of ethyl ether were added to give two phases mixture. The mixture was seeded with the product and precipitation started. The reaction mixture was stirred on ice bath (2-5° C.) for additional 1 h, filtered and washed with 1/3 ethyl acetate/ether mixture (100 mL) to give 140 g of very hygroscopic light yellow solid that was dried on a rotavapor for 2 h and stored under nitrogen in deep freeze. The dry 4-(3-(methylsulfinyl)phenyl)-1-propyl-1,2,3,6-tetrahydropyridine-HCl is slightly yellowish solid (94.1 g, 79% yield, HPLC (254 nm): 96.3% area, 1H-NMR assay: 97.5%).

NMR Identity Analysis of Compound 7

Compound 7

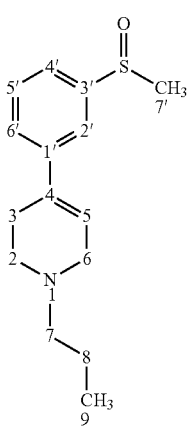

The following data in Tables 14 and 15 was determined using a sample of Compound 7, a solvent of $CDCl_3$, and the instruments were a Bruker AMX500 and Avance III 800 MHz instrument.

TABLE 14

Assignment of $^1$H NMR[a]

| $^1$H Shift (ppm) | $^1$H Shift (ppm)[b] | Integral | Multiplicity | Assignment | COSY cross peaks |
|---|---|---|---|---|---|
| 2.63 | 2.66 | 2 | t, 2 × 5.7 to H3 | H | H3 |
| 7.51 | 7.55 | 2 | m | H3 | H2, H5, H6 |
| 6.10 | 6.13 | 1 | tt, 2 × 3.6 to H6, 2 × 1.5 to H3 | H5 | H3, H6 |
| 3.09 | 3.13 | 2 | m | H6 | H3, H5 |
| 2.35 | 2.39 | 2 | m | H7 | H8 |
| 1.51 | 1.54 | 2 | m | H8 | H7, H9 |
| 0.86 | 0.89 | 3 | t, 2 × 7.4 to H8 | H9 | H8 |
| 7.60 | 7.49 | 1 | dt 0.4 to H5', 2 × 1.8 to H4' and H6' | H2' | H4', H5', H6' |
| 7.37 | 7.40 | 1 | ddd, 1.4 to H6', 1.8 to H5', 7.6 to H2' | H4' | H2', H5', H6' |
| 7.36 | 7.37 | 1 | dt, 0.4 to H2', 2 × 7.6 to H4' and H6' | H5' | H2', H4', H6' |
| 7.41 | 7.44 | 1 | ddd, 1.4 to H4', 1.8 to H5', 7.6 to H2' | H6' | H2', H4', H5' |
| 2.62 | 2.66 | 3 | s | H7' | — |

[a]Spectra is calibrated by the solvent residual peak (2.5 ppm).
[b]after addition of small amount of $C_6D_6$

TABLE 15

Assignment of $^{13}$C NMR[a,]

| $^{13}$C Shift (ppm) | Assignment | HMBC $^1$H cross peaks | $^{13}$C Shift (ppm) | Assignment | HMBC $^1$H cross peaks |
|---|---|---|---|---|---|
| 49.89 | C2 | C4, 6, 7 | 142.00 | C1' | — |
| 27.68 | C3 | C2, 4, 5 | 119.41 | C2' | C4, 6, 3', 4' |
| 133.67 | C4 | — | 145.52 | C3' | — |
| 123.57 | C5 | C3, 6, 1' | 121.51 | C4' | C2', 6' |
| 52.90 | C6 | C2, 4, 5, 7 | 128.97 | C5' | — |
| 60.04 | C7 | C2, 6, 8, 9 | 127.19 | C6' | C2', 4', 4 |
| 20.02 | C8 | C7, 9 | 43.70 | C7' | 3' |
| 11.72 | C9 | C7, 8 | | | |

[a]Spectra is calibrated by a solvent peak (77.0 ppm)

Example 8—Analysis of the Amounts of Compounds 1, 2, 3, 4, 5 and 6 in a Sample of Pridopidine Drug Substance Compounds 1-7 are useful to determine the purity of a pridopidine containing composition.

The procedure used for determination of assay and related substances in pridopidine HCl is a reverse phase HPLC method using X-bridge phenyl column (or equivalent) and gradient elution with UV detection at 268 nm. The mobile phase consists of a mixture of methanol and ammonium formate buffer.

Apparatus

HPLC with gradient pump, column thermostat and UV-detector. Column: Waters. X-bridge Phenyl, 75×4 6 mm, 2.5 µm; or an equivalent column.

Analytical Instruction

Reagents and Solutions

Solvents: Methanol, HPLC grade, Water. MilliQ-water or equivalent Reagents. Ammonium formate, purum; Ammonium hydroxide. 30% A.C.S; Formic acid, pa Ammonium formate buffer, 1.00 mM, pH 8.90-9.10: Weigh 6.3-6.4 g ammonium formate accurately into a 1000 mL volumetric flask and add 2.5 ml 30% ammonium hydroxide solution. Dissolve and dilute with milliQ-water to 900 mL. Measure the pH of the solution. The pH should be between 8.90 and 9.10, otherwise adjust with ammonium hydroxide or formic acid. Dilute to volume and filter through a 0.45 μm HVLP-filter.

Reference substances: Control Sample 1a: (pridopidine) (see FIG. 1; Control Sample 2b (Compound 5, Compound 1, Compound 4, pridopidine, Compound 8, Compound 2, Compound 6, Compound 3)

TABLE 16

| Phase | Solvent | Amount |
|---|---|---|
| Mobile phase A | Ammonium formate buffer, 100 mM, pH 9.0 | 100 mL |
|  | MilliQ-water | 900 mL |
| Mobile phase B | Ammonium formate buffer, 100 mM, pH 9.0 | 100 mL |
|  | MilliQ-water | 50 mL |
|  | Methanol | 850 mL |
| Dilution phase | Methanol | 150 mL |
|  | MilliQ-water | 850 mL |

TABLE 17

| Analytical conditions | | |
|---|---|---|
| Flow | 0.8 mL/min | |
| Gradient | Time (min) | Mobile phase B (%) |
|  | 0 | 50 |
|  | 10 | 100 |
|  | 12 | 100 |
|  | Equilibration time 3 min. | |
| Wavelength | 268 nm bandwidth 4 nm; reference off) | |
|  | 190-400 nm (for information in stability studies only). | |
| Injected volume | 20 μL | |
| Needle wash | Set wash cycles to two. Use dilution phase in washing vial. | |
| Temperature | 40° C. | |

TABLE 18

| Approximate retention times | |
|---|---|
| Substance | Time (min) |
| Compound 5 | 1.9 |
| Compound 1 | 2.4 |
| Compound 4 | 3.5 |
| Pridopidine | 4.6 |
| Compound 8 | 6.1 |
| Compound 2 | 7.5 |
| Compound 6 | 8.8 |
| Compound 3 | 9.9 |

Blank preparation: Use dilution phase. Duplicate vials of blank (A and B).

Reference Preparation a (Only for Related Substances)
Use Control Sample 2b. Inject as it is.
The Control Sample 2b solution is a pridopidine solution (0.44 mg/ml free base) spiked with approximately 1% of each of the impurities: Compound 5, Compound 1, Compound 4, Compound 8, Compound 2, Compound 6 and Compound 3.

Reference Preparation B (Only for Assay)
Duplicate Preparation (B1 and B2).
Weigh 43-45 mg of pridopidine reference into a 50 mL volumetric flask. Add 25 mL dilution phase and shake or sonicate at ambient temperature until the reference is dissolved. Make to volume with dilution phase. Concentration: 0.9 mg/mL pridopidine. The standard solution is stable for 48 hours when stored in daylight and in room temperature.

Reference Preparation C (Only for Related Substances)
Single Preparation (C).
Dilute 1 mL of reference B1 to 100 mL with dilution phase. Dilute further 1 mL of this solution to 20 mL with dilution phase (sensitivity standard, concentration corresponding to 0.05% of sample concentration).

Sample Preparation
Duplicate Preparation (Sample A and B).
Weigh 43-45 mg of the sample of pridopidine into a 50 mL volumetric flask. Add 25 mL dilution phase and shake or sonicate at ambient temperature until the sample is dissolved. Make to volume with dilution phase. Concentration: 0.9 mg/mL pridopidine. The sample solution should be freshly prepared before use.

Order of Determinations
When the system is equilibrated, inject the solutions in the following order:

TABLE 19

| | Number of determinations/injections | |
|---|---|---|
| Solution | Assay | Related substances |
| Blank A | 3 (at least) | 1 (at least) |
| Blank B | 1 | 1 |
| Reference A | N/A | 1 |
| Reference C | N/A | 1 |
| Reference B1 | 5 | N/A |
| Reference B2 | 1 | N/A |
| Sample A | 1 | 1 |
| Sample B | 1 | 1 |
| . . . | . . . | . . . |
| Reference B2 | 1 | N/A |

Calculation
System Suitability
For Related Substances:
R1) The Blank B should be free from interfering peaks at the retention times of Compound 5, Compound 1, Compound 4, pridopidine, Compound 8, Compound 2, Compound 6 and Compound 3.

R2) The retention time of the pridopidine peak should be 4.6±0.5 min.

Figure 2:
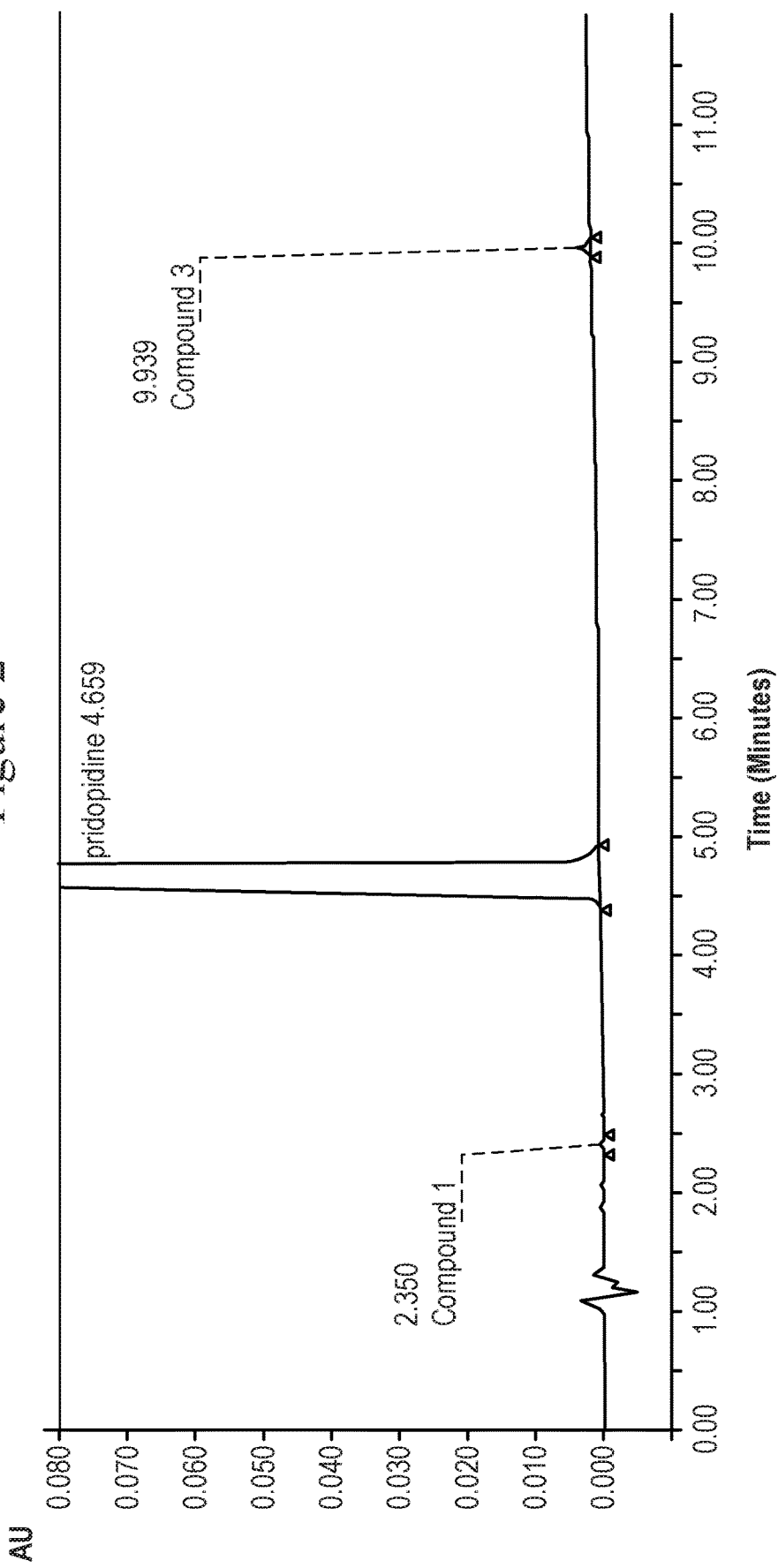
FIG. 2: Typical Chromatogram of the control sample 2b.

R3) Compound 5, Compound 1, Compound 4, pridopidine, Compound 8, Compound 2, Compound 6 and Compound 3 in the Control Sample 2b should be possible to identify according to FIG. 2.

R4) The pridopidine peak in reference C should have a signal-to-noise ratio greater than or equal to 3.

R5) Calculate the number of theoretical plates (N) and the tailing factor (T) for the pridopidine peak in reference A. Number of theoretical plates 2: 8000 and tailing factor 0.7-1.0.

R6) Calculate the resolution between Compound 5 and Compound 1 in the Control Sample 2b, should be greater than or equal to 1.5.

R7) If the problem with split peaks Compound 1 and Compound 4 shall appear, they should be calculated as sum of each split peak.

For Assay:

A1) The Blank B should be free from interfering peak at the retention time for pridopidine.

A2) The retention time of the pridopidine peak should be 4.6±0.5 min.

A3) Calculate the RSD % of the five areas of reference B1. The RSD should be ~2.0%.

A4) Calculate the assay of each injections of reference B2. The assay should be in the interval 99-101 w/w-% of the assay of the reference B1.

A5) Calculate the number of theoretical plates (N) and the tailing factor (T) for the pridopidine peak in the first injection of reference B1. Number of theoretical plates 2: 8000 and tailing factor 0.7-1.0.

A6) Calculate the deviation between the two assay determinations (Sample A and B) according to eq. 1. The deviation should be less than or equal to 2%.

$$\frac{|Assay_A - Assay_B| \times 100}{(Assay_A + Assay_B) \times 0.5} \leq 2\% \qquad (eq.\ 1)$$

The analytical method description described herein will be updated to include acceptance criteria for number of theoretical plates (N) and the tailing factor (T) for pridopidine peak.

Result

For Related Substances:

The content of related substances should be calculated as area-% and corrected with relative response factors and reported as % according to eq. 2.

$$\%_x = area\text{-}\%_x \times RRF_x \qquad (eq.\ 2)$$

$\%_x$ percent content of an impurity 'x' area-$\%_x$ area-% of an impurity 'x' calculated from the chromatogram $RRF_x$ Relative Response Factor of an impurity 'x'

Use following response factors:

TABLE 20

| Name | Relative response factor |
|---|---|
| Compound 8 | 0.2 |
| Compound 2 | 0.7 |

Remaining related substances will be correct for RRF 1.

For Assay:

Calculate the assay of pridopidine in w/w-% using the external standard methodology (see below). Use the mean response factor obtained from the five injections of reference B1 for the calculation.

$$f_x = \frac{c_{xR}}{A_{xR}} \qquad (eq.\ 3)$$

$$\frac{A_{xS} \times f_x \times 100}{c_{xS}} = pridopidine\ (w/w - \%) \qquad (eq.\ 4)$$

$f_x$ mean response factor of pridopidine from reference solution B1

$c_{xR}$ concentration of pridopidine in reference solution (mg/ml)

$c_{xS}$ concentration of sample solution (mg/mL)

$A_{xR}$ area of pridopidine in each injection of reference solution B1

$A_{xS}$ area of pridopidine in sample chromatogram

TABLE 21

Analytical Methods for Determination of Impurities in the Drug Substance

| Parameter | Example Number | Method Type | Quantitation Limit (wegith-%) | Quantitation Limit (area-%) | Detection Limit (area-%) |
|---|---|---|---|---|---|
| Compound 1 | Example 8 | RP-HPLC | 0.04 | 0.04 | 0.01 |
| Compound 2 | Example 8 | RP-HPLC | 0.03 | 0.05 | 0.01 |
| Compound 3 | Example 8 | RP-HPLC | 0.05 | 0.05 | 0.03 |
| Compound 4 | Example 8 | RP-HPLC | 0.04 | 0.04 | 0.01 |
| Compound 5 | Example 8 | RP-HPLC | 0.04 | 0.04 | 0.01 |
| Compound 6 | Example 8 | RP-HPLC | 0.04 | 0.04 | 0.01 |

During course of the validation the response factors for Compound 5, Compound 1, Compound 4, Compound 8, Compound 2, Compound 6 and Compound 3 has been evaluated and compared to the response factor of pridopidine. The relative response factor of the impurities are presented in Table 22:

TABLE 22

Relative Response Factors

| Name | Relative Response Factor (α pridopidine/α |
|---|---|
| Compound 5 | 0.91 |
| Compound 1 | 1.01 |
| Compound 4 | 1.02 |
| Compound 8 | 0.16 |
| Compound 2 | 0.65 |
| Compound 6 | 1.05 |
| Compound 3 | 0.99 |

Example 9—Specification of Pridopidine Hydrochloride Drug Substance

TABLE 23

| Name | Ret. time (min) | Resolution tangent method) |
|---|---|---|
| Compound 5 | 1.99 | N/A |
| Compound 1 | 2.42 | 3.3 |
| Compound 4 | 3.58 | 6.6 |
| pridopidine | 4.68 | 4.9 |
| Compound 8 | 6.09 | 7.5 |
| Compound 2 | 7.36 | 11.2 |
| Compound 6 | 8.69 | 11.8 |
| Compound 3 | 9.92 | 10.1 |

Pridopidine HCl is a white to almost white powder. The specifications of pridopidine HCl are as follows:

TABLE 24

Specification of Pridopidine Hydrochloride Drug Substance

| Test | Acceptance Criteria | Method |
|---|---|---|
| Description | White to almost white powder | Visual inspection |
| Absence of lumps | Pass | Visual and touching |
| Identification | | |
| IR | Conforms to reference IR spectrum | IR |
| X-ray diffractogram | Conforms to reference X-ray diffractogram | XRPD |
| Chloride | Positive | Ph. Eur. |
| Assay, HPLC, % w/w | 98.0-102.0 | HPLC |
| Related substances, HPLC, area % | | |
| Compound 5 | ≤0.15 | HPLC |
| Compound 1 | ≤0.15 | HPLC |
| Compound 4 | ≤0.15 | HPLC |
| Compound 8 | ≤0.15 | HPLC |
| Compound 3 | ≤0.15 | HPLC |
| Compound 2 | ≤0.15 | HPLC |
| Compound 6 | ≤0.15 | HPLC |
| Unknown impurities, each | ≤0.10 | HPLC |
| Impurities in total | ≤0.50 | HPLC |

Example 10—Accelerated and Long Term Stability in Pridopidine HCl Drug Product Batches 1, 2 and 3 were manufactured according to cGMP and in scale as the expected commercial scale. Batches 4 and 5 were manufactured according to the current route of synthesis.

The stability program for each batch is detailed below in Table 25.

TABLE 25

Pridopidine HCl Stability Testing Program

| Batch | 1 | 2 | 3 | 4 | 5 |
|---|---|---|---|---|---|
| Batch size (kg) | 99.7 | 97.2 | 96.6 | 14.9 | 105.4 |
| Stability study | | | | | |
| Storage conditions and testing intervals | 25° C./60% RH: 0, 3, 6, 9, 12, 18, 24, 36, 48 and 60 months 30° C./65% RH: 0, 3, 6, 9 and 12 months 40° C./75% RH: 0, 3 and 6 months | | | 25° C./60% RH: 0, 3, 6, 9, 12, 18, 24, 36, 48 and 60 months 30° C./65% RH: 0, 3, 6, 9 and 12 months 40° C./75% RH: 0, 3 and 6 months | |
| Test parameters | Appearance, Identification, Crystal form, Assay, Impurities, Water content, Microbial limit | | | Appearance, Identification, Crystal form, Assay, Impurities, Water content, Microbial limit | |

Stability data for batches 1, 2, 3, 4 and 5 can be found in Tables 26-37:

TABLE 26

Stability Data of Pridopidine HCl Batch 1 Stored at 25° C./60% RH

| Parameters | Acceptance Criteria | Storage Period (Months) | | | | | | | | |
|---|---|---|---|---|---|---|---|---|---|---|
| | | 0 | 3 | 6 | 9 | 12 | 18 | 24 | 36 | 48 |
| Appearance | Color and Form | White powder Conforms | White powder Conforms | White powder Conforms | White powder Conforms | White powder Conforms | White powder Conforms | White powder Conforms | White powder Conforms | White powder Conforms |
| Identification (by IR) | Complies with ref spectrum | | | | | | | | | |
| Crystal Form (by X-Ray) | Complies with ref diffractogram | Conforms | Conforms | Conforms | Conforms | Conforms | Conforms | Not scheduled | Not scheduled | Not scheduled |
| Assay (by HPLC) [% w/w] | 98.0-102.0 | 99.9 | 99.7 | 100.2 | 100.2 | 99.6 | 100.0 | 100.4 | 99.8 | 99.7 |
| Impurities (by HPLC) [area %] | | | | | | | | | | |
| Compound 1 | ≤0.15 | 0.05 | 0.05 | 0.05 | 0.05 | 0.05 | <0.05 | <0.05 | <0.05 | <0.05 |
| Compound 4 | ≤0.15 | 0.09 | 0.09 | 0.09 | 0.09 | 0.09 | 0.08 | 0.08 | 0.09 | 0.08 |
| Each (Compound 8, Compound 3, Compound 2, Compound 6 and Compound 5) | ≤0.15 | <0.05 | <0.05 | <0.05 | <0.05 | <0.05 | <0.05 | <0.05 | <0.05 | <0.05 |
| Unknown Impurities Each | ≤0.10 | <0.05 | <0.05 | <0.05 | <0.05 | <0.05 | <0.05 | <0.05 | <0.05 | <0.05 |
| Total | ≤0.50 | 0.14 | 0.15 | 0.14 | 0.14 | 0.14 | 0.08 | 0.08 | 0.09 | 0.08 |
| Water Content (by KF) [% w/w] | Run and record | 0.03 | 0.03 | 0.02 | 0.01 | 0.02 | <0.05 | <0.05 | 0.06 | <0.05 |
| Microbiological | | | | | | | | | | |

TABLE 26-continued

Stability Data of Pridopidine HCl Batch 1 Stored at 25° C./60% RH

| Parameters | Acceptance Criteria | Storage Period (Months) | | | | | | | | |
|---|---|---|---|---|---|---|---|---|---|---|
| | | 0 | 3 | 6 | 9 | 12 | 18 | 24 | 36 | 48 |
| Purity [cfu/g] | | | | | | | | | | |
| TAMC | ≤1000 | <10 | Not scheduled | Not scheduled | Not scheduled | <10 | Not scheduled | Not scheduled | Not scheduled | Not scheduled |
| TYMC | ≤10 | <10 | Not scheduled | Not scheduled | Not scheduled | <10 | Not scheduled | Not scheduled | Not scheduled | Not scheduled |
| E. Coli | Absent | — | — | — | — | — | — | — | — | — |

TABLE 27

Stability Data of Pridopidine HCl Batch 1 Stored at 40° C./75% RH

| Parameters | Acceptance Criteria | Storage Period (Months) | | |
|---|---|---|---|---|
| | | 0 | 3 | 6 |
| Appearance | Color and Form | White powder | White powder | White powder |
| Identification (by IR) | Complies with ref spectrum | Conforms | Conforms | Conforms |
| Crystal Form (by X-Ray) | Complies with ref diffractogram | Conforms | Conforms | Conforms |
| Assay (by HPLC) [% w/w] | 98.0-102.0 | 99.9 | 99.7 | 100.1 |
| Impurities (by HPLC) [area %] | | | | |
| Compound 1 | ≤0.15 | 0.05 | 0.05 | 0.05 |
| Compound 4 | ≤0.15 | 0.09 | 0.09 | 0.09 |
| Each (Compound 8, Compound 3, Compound 2, Compound 6 and Compound 5 Unknown Impurities Each | ≤0.15 | <0.05 | <0.05 | <0.05 |
| | ≤0.10 | <0.05 | <0.05 | <0.05 |
| Total | ≤0.50 | 0.14 | 0.14 | 0.14 |
| Water Content (by KF) [% w/w] | Run and record | <0.1 | <0.1 | <0.1 |
| Microbiological Purity [cfu/g] | | | | |
| TAMC | ≤1000 | <10 | Not scheduled | Not scheduled |
| TYMC | ≤10 | <10 | Not scheduled | Not scheduled |
| E. Coli | Absent | — | — | — |

TABLE 28

Stability Data of Pridopidine HCl Batch 2 Stored at 25° C./60% RH

| Parameters | Acceptance Criteria | Storage Period (Months) | | | | | | | | |
|---|---|---|---|---|---|---|---|---|---|---|
| | | 0 | 3 | 6 | 9 | 12 | 18 | 24 | 36 | 48 |
| Appearance | Color and Form | White powder | White powder | White powder | White powder | White powder | White powder | White powder | White powder | White powder |
| Identification (by IR) | Complies with ref spectrum | Conforms | Conforms | Conforms | Conforms | Conforms | Conforms | Conforms | Conforms | Conforms |
| Crystal Form (by X-Ray) | Complies with ref diffractogram | Conforms | Conforms | Conforms | Conforms | Conforms | Conforms | Not scheduled | Not scheduled | Not scheduled |
| Assay (by HPLC) [% w/w] | 98.0-102.0 | 100.1 | 99.9 | 100.4 | 100.3 | 100.2 | 100.1 | 100.4 | 99.7 | 100.5 |
| Impurities (by HPLC) [area %] | | | | | | | | | | |
| Compound 4 | ≤0.15 | 0.05 | 0.05 | 0.05 | 0.05 | 0.05 | <0.05 | 0.05 | <0.05 | <0.05 |
| Each (Compound 1, Compound 8, Compound 3, Compound 2, Compound 6 and Compound 5) | ≤0.15 | <0.05 | <0.05 | <0.05 | <0.05 | <0.05 | <0.05 | <0.05 | <0.05 | <0.05 |

TABLE 28-continued

Stability Data of Pridopidine HCl Batch 2 Stored at 25° C./60% RH

| Parameters | Acceptance Criteria | Storage Period (Months) | | | | | | | | |
|---|---|---|---|---|---|---|---|---|---|---|
| | | 0 | 3 | 6 | 9 | 12 | 18 | 24 | 36 | 48 |
| Unknown Impurities Each | ≤0.10 | <0.05 | <0.05 | <0.05 | <0.05 | <0.05 | <0.05 | <0.05 | <0.05 | <0.05 |
| Total | ≤0.50 | 0.05 | 0.05 | 0.05 | 0.05 | 0.05 | <0.05 | 0.05 | <0.05 | <0.05 |
| Water Content (by KF) [% w/w] | Run and record | 0.03 | 0.02 | 0.01 | 0.01 | 0.02 | <0.05 | <0.05 | <0.05 | <0.05 |
| Microbiological Purity [cfu/g] | | | | | | | | | | |
| TAMC | ≤1000 | <10 | Not scheduled | Not scheduled | Not scheduled | <10 | Not scheduled | Not scheduled | Not scheduled | Not scheduled |
| TYMC | ≤10 | <10 | Not scheduled | Not scheduled | Not scheduled | <10 | Not scheduled | Not scheduled | Not scheduled | Not scheduled |
| E. Coli | Absent | — | — | — | — | — | — | — | — | — |

TABLE 29

Stability Data of Pridopidine HCl Batch 2 Stored at 40° C./75% RH

| Parameters | Acceptance Criteria | Storage Period (Months) | | |
|---|---|---|---|---|
| | | 0 | 3 | 6 |
| Appearance | Color and Form | White powder | White powder | White powder |
| Identification (by IR) | Complies with ref spectrum | Conforms | Conforms | Conforms |
| Crystal Form (by X-Ray) | Complies with ref diffractogram | Conforms | Conforms | Conforms |
| Assay (by HPLC) [% w/w] | 98.0-102.0 | 100.1 | 99.6 | 100.6 |
| Impurities (by HPLC) [area %] | | | | |
| Compound 4 | ≤0.15 | 0.05 | 0.05 | 0.05 |
| Each (Compound 1, Compound 8, Compound 3, Compound 2, Compound 6 and Compound 5) | ≤0.15 | <0.05 | <0.05 | <0.05 |
| Unknown Impurities Each | ≤0.10 | | | |
| Total | ≤0.50 | 0.05 | 0.05 | 0.05 |
| Water Content (by KF) [% w/w] | Run and record | <0.1 | <0.1 | <0.1 |
| Microbiological Purity [cfu/g] | | | | |
| TAMC | ≤1000 | <10 | Not scheduled | Not scheduled |
| TYMC | ≤10 | <10 | Not scheduled | Not scheduled |
| E. Coli | Absent | — | — | — |

TABLE 30

Stability Data of Pridopidine HCl Batch 3 Stored at 25° C./60% RH

| Parameters | Acceptance Criteria | Storage Period (Months) | | | | | | | | |
|---|---|---|---|---|---|---|---|---|---|---|
| | | 0 | 3 | 6 | 9 | 12 | 18 | 24 | 36 | 48 |
| Appearance | Color and Form | White powder | White powder | White powder | White powder | White powder | White powder | White powder | White powder | White powder |
| Identification (by IR) | Complies with ref spectrum | Conforms | Conforms | Conforms | Conforms | Conforms | Conforms | Conforms | Conforms | Conforms |
| Crystal Form (by X-Ray) | Complies with ref diffractogram | Conforms | Conforms | Conforms | Conforms | Conforms | Conforms | Not scheduled | Not scheduled | Not scheduled |
| Assay (by HPLC) [% w/w] | 98.0-102.0 | 100.5 | 99.8 | 100.4 | 100.6 | 100.0 | 100.1 | 100.5 | 100.2 | 100.5 |
| Impurities (by HPLC) [area %] | | | | | | | | | | |
| Compound 4 | ≤0.15 | 0.06 | 0.06 | 0.06 | 0.06 | 0.06 | 0.06 | 0.05 | 0.05 | 0.05 |
| Each (Compound 1, Compound 8, Compound 3, | ≤0.15 | <0.05 | <0.05 | <0.05 | <0.05 | <0.05 | <0.05 | <0.05 | <0.05 | <0.05 |

TABLE 30-continued

Stability Data of Pridopidine HCl Batch 3 Stored at 25° C./60% RH

| Parameters | Acceptance Criteria | Storage Period (Months) | | | | | | | | |
|---|---|---|---|---|---|---|---|---|---|---|
| | | 0 | 3 | 6 | 9 | 12 | 18 | 24 | 36 | 48 |
| Compound 2, Compound 6 and Compound 5) Unknown Impurities Each | ≤0.10 | <0.05 | <0.05 | <0.05 | <0.05 | <0.05 | <0.05 | <0.05 | <0.05 | <0.05 |
| Total | ≤0.50 | 0.06 | 0.06 | 0.06 | 0.06 | 0.06 | 0.06 | 0.05 | 0.05 | 0.05 |
| Water Content (by KF) [% w/w] | Run and record | 0.03 | 0.03 | 0.01 | 0.01 | 0.01 | <0.05 | <0.05 | <0.05 | <0.05 |
| Microbiological Purity [cfu/g] | | | | | | | | | | |
| TAMC | ≤1000 | <10 | Not scheduled | Not scheduled | Not scheduled | <10 | Not scheduled | Not scheduled | Not scheduled | Not scheduled |
| TYMC | ≤10 | <10 | Not scheduled | Not scheduled | Not scheduled | <10 | Not scheduled | Not scheduled | Not scheduled | Not scheduled |
| E. Coli | Absent | — | — | — | — | — | — | — | — | — |

TABLE 31

Stability Data of Pridopidine HCl Batch 3 Stored at 40° C./75% RH

| Parameters | Acceptance Criteria | Storage Period (Months) | | |
|---|---|---|---|---|
| | | 0 | 3 | 6 |
| Appearance | Color and Form | White powder | White powder | White powder |
| Identification (by IR) | Complies with ref spectrum | Conforms | Conforms | Conforms |
| Crystal Form (by X-Ray) | Complies with ref diffractogram | Conforms | Conforms | Conforms |
| Assay (by HPLC) [% w/w] | 98.0-102.0 | 100.5 | 99.7 | 100.5 |
| Impurities (by HPLC) [area %] | | | | |
| Compound 4 | ≤0.15 | 0.06 | 0.06 | 0.06 |
| Each (Compound 1, Compound 8, Compound 3, Compound 2, Compound 6 and Compound 5) Unknown Impurities Each | ≤0.15 | <0.05 | <0.05 | <0.05 |
| | ≤0.10 | <0.05 | <0.05 | <0.05 |
| Total | ≤0.50 | 0.06 | 0.06 | 0.06 |
| Water Content (by KF) [% w/w] | Run and record | <0.1 | <0.1 | <0.1 |
| Microbiological Purity [cfu/g] | | | | |
| TAMC | ≤1000 | <10 | Not scheduled | Not scheduled |
| TYMC | ≤10 | <10 | Not scheduled | Not scheduled |
| E. Coli | Absent | — | — | — |

TABLE 32

Stability Data of Pridopidine HCl Batch 4 Stored at 25° C./60% RH

| Parameters | Acceptance Criteria | Storage Period (Months) | | | | | | | |
|---|---|---|---|---|---|---|---|---|---|
| | | 0 | 3 | 6 | 9 | 12 | 18 | 24 | 36 |
| Appearance | Color and Form | White powder | White powder | White powder | White powder | White powder | White powder | White powder | White powder |
| Identification (by IR) | Complies with ref spectrum | Conforms | Conforms | Conforms | Conforms | Conforms | Conforms | Conforms | Conforms |
| Crystal Form (by X-Ray) | Complies with ref diffractogram | Conforms | Not scheduled | Not scheduled | Not scheduled | Not scheduled | Not scheduled | Not scheduled | Not scheduled |
| Assay (by HPLC) [% w/w] | 98.0-102.0 | 100.4 | 98.6 | 99.8 | 99.7 | 99.5 | 99.9 | 99.8 | 100.1 |
| Impurities (by HPLC) [area %] | | | | | | | | | |
| Compound 4 | ≤0.15 | 0.06 | 0.06 | 0.07 | 0.06 | 0.07 | 0.06 | 0.06 | 0.06 |
| Compound 3 | ≤0.15 | 0.06 | <0.05 | 0.06 | 0.08 | 0.06 | 0.07 | 0.06 | 0.05 |
| Compound 8 | ≤0.15 | <0.01 | <0.01 | <0.01 | <0.01 | <0.01 | <0.01 | <0.01 | <0.01 |
| Each (Compound 1, Compound 2, Compound 6, | ≤0.10 | <0.05 | <0.05 | <0.05 | <0.05 | <0.05 | <0.05 | <0.05 | <0.05 |

TABLE 32-continued

Stability Data of Pridopidine HCl Batch 4 Stored at 25° C./60% RH

| Parameters | Acceptance Criteria | Storage Period (Months) | | | | | | | |
|---|---|---|---|---|---|---|---|---|---|
| | | 0 | 3 | 6 | 9 | 12 | 18 | 24 | 36 |
| Compound 5 and Unknown Impurities Each) | | | | | | | | | |
| Total | ≤0.50 | 0.12 | 0.06 | 0.13 | 0.14 | 0.13 | 0.14 | 0.13 | 0.11 |
| Water Content (by KF) [% w/w] | Run and record | 0.06 | <0.05 | <0.05 | <0.05 | <0.05 | <0.05 | <0.05 | <0.05 |
| Microbiological Purity [cfu/g] | | | | | | | | | |
| TAMC | ≤1000 | <10 | Not scheduled | Not scheduled | Not scheduled | Not scheduled | Not scheduled | Not scheduled | Not scheduled |
| TYMC | ≤10 | <10 | Not scheduled | Not scheduled | Not scheduled | Not scheduled | Not scheduled | Not scheduled | Not scheduled |
| *E. Coli* | Absent | Not detectable | Not scheduled | Not scheduled | Not scheduled | Not scheduled | Not scheduled | Not scheduled | Not scheduled |

TABLE 33

Stability Data of Pridopidine HCl Batch 4 Stored at 30° C./65% RH

| Parameters | Acceptance Criteria | Storage Period (Months) | | | | |
|---|---|---|---|---|---|---|
| | | 0 | 3 | 6 | 9 | 12 |
| Appearance | Color and Form | White powder | White powder | White powder | White powder | White powder |
| Identification (by IR) | Complies with ref spectrum | Conforms | Conforms | Conforms | Conforms | Conforms |
| Crystal Form (by X-Ray) | Complies with ref diffractogram | Conforms | Not scheduled | Not scheduled | Not scheduled | Conforms |
| Assay (by HPLC) [% w/w] | 98.0-102.0 | 100.4 | 99.0 | 99.5 | 100.0 | 99.6 |
| Impurities (by HPLC) [area %] | | | | | | |
| Compound 4 | ≤0.15 | 0.06 | 0.07 | 0.07 | 0.06 | 0.06 |
| Compound 3 | ≤0.15 | 0.06 | <0.05 | 0.07 | 0.07 | 0.06 |
| Compound 8 | ≤0.15 | <0.01 | <0.01 | <0.01 | <0.01 | <0.01 |
| Each (Compound 1, Compound 2, Compound 6, Compound 5 and Unknown Impurities Each) | ≤0.15 | <0.05 | <0.05 | <0.05 | <0.05 | <0.05 |
| Total | ≤0.50 | 0.12 | 0.07 | 0.13 | 0.13 | 0.12 |
| Water Content by KF) [% w/w] | Run and record | <0.1 | <0.1 | <0.1 | <0.1 | <0.1 |
| Microbiological Purity [cfu/g] | | | | | | |
| TAMC | ≤1000 | <10 | Not scheduled | Not scheduled | Not scheduled | <10 |
| TYMC | ≤10 | <10 | Not scheduled | Not scheduled | Not scheduled | <10 |
| *E. Coli* | Absent | Not detectable | Not scheduled | Not scheduled | Not scheduled | Not detectable |

TABLE 34

Stability Data of Pridopidine Hcl Batch 4 Stored at 40° C./75% RH

| Parameters | Acceptance Criteria | Storage Period (Months) | | |
|---|---|---|---|---|
| | | 0 | 3 | 6 |
| Appearance | Color and Form | White powder | White powder | White powder |
| Identification (by IR) | Complies with ref spectrum | Conforms | Conforms | Conforms |
| Crystal Form (by X-Ray) | Complies with ref diffractogram | Conforms | Not scheduled | Conforms |
| Assay (by HPLC) [% w/w] | 98.0-102.0 | 100.4 | 99.5 | 99.7 |
| Impurities (by HPLC) [area %] | | | | |
| Compound 4 | ≤0.15 | 0.06 | 0.07 | 0.07 |
| Compound 3 | ≤0.15 | 0.06 | <0.05 | 0.07 |
| Compound 8 | ≤0.15 | <0.01 | <0.01 | <0.01 |
| Each (Compound 1, Compound 2, Compound 6, Compound 5 and Unknown Impurities Each) | ≤0.15 | <0.05 | <0.05 | <0.05 |
| Total | ≤0.50 | 0.12 | 0.07 | 0.13 |
| Water Content by KF) [% w/w] | Run and record | 0.06 | <0.05 | <0.05 |
| Microbiological Purity [cfu/g] | | | | |
| TAMC | ≤1000 | <10 | Not scheduled | <10 |
| TYMC | ≤10 | <10 | Not scheduled | <10 |
| E. Coli | Absent | Not detectable | Not scheduled | Not detectable |

TABLE 35

Stability Data of Pridopidine HCl Batch 5 Stored at 25° C./60% RH

| Parameters | Acceptance Criteria | Storage Period (Months) | | | | | | |
|---|---|---|---|---|---|---|---|---|
| | | 0 | 3 | 6 | 9 | 12 | 18 | 24 |
| Appearance | Color and Form | White powder | White powder | White powder | White powder | White powder | White powder | White powder |
| Identification (by IR) | Complies with ref spectrum | Conforms | Conforms | Conforms | Conforms | Conforms | Conforms | Conforms |
| Crystal Form (by X-Ray) | Complies with ref diffractogram | Conforms | Not scheduled | Not scheduled | Not scheduled | Not scheduled | Not scheduled | Not scheduled |
| Assay (by HPLC) [% w/w] | 98.0-102.0 | 99.8 | 100.0 | 99.9 | 99.9 | 99.7 | 100.1 | 100.1 |
| Impurities (by HPLC) [area %] | | | | | | | | |
| Compound 3 | ≤0.15 | 0.10 | 0.09 | 0.07 | 0.09 | 0.11 | 0.11 | 0.07 |
| Compound 8 | ≤0.15 | <0.01 | <0.01 | <0.01 | <0.01 | <0.01 | <0.01 | <0.01 |
| Each (Compound 1, Compound 5, Compound 4, Compound 2, Compound 6 and Unknown Impurities Each) | ≤0.15 | <0.05 | <0.05 | <0.05 | <0.05 | <0.05 | <0.05 | <0.05 |
| Total | ≤0.50 | 0.10 | 0.09 | 0.07 | 0.09 | 0.11 | 0.11 | 0.07 |
| Water Content (by KF) [% w/w] | Run and record | <0.05 | <0.05 | <0.05 | <0.05 | <0.05 | <0.05 | <0.05 |
| Microbiological Purity [cfu/g] | | | | | | | | |
| TAMC | ≤1000 | Not scheduled | Not scheduled | Not scheduled | Not scheduled | Not scheduled | Not scheduled | Not scheduled |
| TYMC | ≤10 | Not scheduled | Not scheduled | Not scheduled | Not scheduled | Not scheduled | Not scheduled | Not scheduled |
| E. Coli | Absent | Not scheduled | Not scheduled | Not scheduled | Not scheduled | Not scheduled | Not scheduled | Not scheduled |

TABLE 36

Stability Data of Pridopidine HCl Batch 5 Stored at 30° C./65% RH

| Parameters | Acceptance Criteria | Storage Period (Months) | | | | |
|---|---|---|---|---|---|---|
| | | 0 | 3 | 6 | 9 | 12 |
| Appearance | Color and Form | White powder | White powder | White powder | White powder | White powder |
| Identification (by IR) | Complies with ref spectrum | Conforms | Conforms | Conforms | Conforms | Conforms |
| Crystal Form (by X-Ray) | Complies with ref diffractogram | Conforms | Not scheduled | Not scheduled | Not scheduled | Conforms |
| Assay (by HPLC) [% w/w] | 98.0-102.0 | 99.8 | 99.8 | 99.8 | 99.8 | 99.7 |
| Impurities (by HPLC) [area %] | | | | | | |
| Compound 8 | ≤0.15 | <0.01 | <0.01 | <0.01 | <0.01 | <0.01 |
| Compound 3 | ≤0.15 | 0.10 | 0.10 | 0.07 | 0.10 | 0.10 |
| Each (Compound 5, Compound 4, Compound 1, Compound 2, Compound 6 and Unknown Impurities Each) | ≤0.15 | <0.05 | <0.05 | <0.05 | <0.05 | <0.05 |
| Total | ≤0.50 | 0.10 | 0.10 | 0.07 | 0.10 | 0.10 |
| Water Content (by KF) [% w/w] | Run and record | <0.05 | <0.05 | <0.05 | <0.05 | <0.05 |
| Microbiological Purity [cfu/g] | | | | | | |
| TAMC | ≤1000 | Not scheduled | Not scheduled | Not scheduled | Not scheduled | <10 |
| TYMC | ≤10 | Not scheduled | Not scheduled | Not scheduled | Not scheduled | <10 |
| E. Coli | Absent | Not scheduled | Not scheduled | Not scheduled | Not scheduled | Not detectable |

TABLE 37

Stability Data of Pridopidine HCl Batch 5 Stored at 40° C./75% RH

| Parameters | Acceptance Criteria | Storage Period (Months) | | |
|---|---|---|---|---|
| | | 0 | 3 | 6 |
| Appearance | Color and Form | White powder | White powder | White powder |
| Identification (by IR) | Complies with ref spectrum | Conforms | Conforms | Conforms |
| Crystal Form (by X-Ray) | Complies with ref diffractogram | Conforms | Not scheduled | Conforms |
| Assay (by HPLC) [% w/w] | 98.0-102.0 | 99.8 | 99.9 | 99.5 |
| Impurities (by HPLC) [area %] | | | | |
| Compound 8 | ≤0.15 | <0.01 | <0.01 | <0.01 |
| Compound 3 | ≤0.15 | 0.10 | 0.10 | 0.06 |
| Each (Compound 5, Compound 4, Compound 1, Compound 2, Compound 6 and Unknown Impurities Each) | ≤0.15 | <0.05 | <0.05 | <0.05 |
| Total | <0.50 | 0.10 | 0.10 | 0.06 |
| Water Content (by KF) [% w/w] | Run and record | <0.05 | <0.05 | <0.05 |
| Microbiological Purity [cfu/g] | | | | |
| TAMC | ≤1000 | Not scheduled | Not scheduled | <10 |
| TYMC | ≤10 | Not scheduled | Not scheduled | <10 |
| E Coli | Absent | Not scheduled | Not scheduled | Not detectable |

Summary of the Results in Tables 26-37 and Conclusions:

Appearance:

No significant change is observed in color or form when stored at 40° C./75% RH for up to 6 months, at 30° C./65% RH for up to 12 months or at 25° C./60% RH for up to 48 months.

Crystal Form:

No change in polymorphic form is observed when pridopidine HCl is stored at 40° C./75% RH for up to 6 months and at 30° C./65% RH for up to 12 months. X-Ray diffractograms recorded after 18 months at 25° C./60% RH showed no change. X-Ray analyses will be performed again at the end of the long term stability program (60 months).

Assay:

When pridopidine HCl is stored at 40° C./75% RH for up to 6 months, no significant change in assay is observed. Similar no significant change is observed when stored at 30° C./65% RH for up to 12 months or at 25° C./60% RH for up to 48 months.

Impurities:

No degradation of pridopidine HCl is observed when the drug substance is stored at 40° C./75% RH for up to 6 months, at 30° C./65% RH for up to 12 months or at 25° C./60% RH for up to 48 months.

Water Content

No significant change regarding water content is observed when pridopidine HCl is stored at 40° C./75% RH for up to 6 months, at 30° C./65% RH for up to 12 months or at 25° C./60% RH for up to 48 months.

Conclusion:

No evidence of relevant changes was observed for the parameters tested at any of the storage conditions. Pridopidine HCl is considered physically and chemically stable when stored at 40° C. and 75% RH for up to 6 months, at 30° C./65% RH for up to 12 months or at 25° C. and 60% RH for up to 48 months.

Example 11—Forced Degradation Study

A forced degradation study has been performed on pridopidine HCl drug product and drug substance. The studied material was subjected to acid and base hydrolysis, thermal stress both as solid and in solution, oxidation, humidity induced stress and photolysis.

The study showed that pridopidine HCl is very stable under most of the studied conditions except for when subjected to oxidative conditions, where considerable degradation was observed. The major degradation product was Compound 5. There was also some degradation in the basic hydrolysis study but only a minor total degradation was observed with the largest degradation product being unidentified.

Mass balance was also investigated and found to be good for all studied conditions.

Summary and Conclusions of Examples 10-11

The amounts of the organic impurities remained below the accepted criteria in all the conditions tested over all time periods as shown in Example 10. Compound 5, which is the only known potential degradation product (Example 11), remained low in all the tested conditions as shown in Example 10.

Example 12—Specification of Pridopidine HCl Drug Product

As detailed in example 10, no degradation products have been detected in the pridopidine HCl in any storage conditions. In addition, no additional impurities are created during the formation of the drug product. Therefore, the same amounts of the organic impurities Compound 1, Compound 2, Compound 3, Compound 4, Compound 5, and Compound 6 which are controlled in the drug substance remain in the drug product, and the accepted criteria relating to the organic impurities Compound 1, Compound 2, Compound 3, Compound 4, Compound 5, and Compound 6 as detailed in Table 22 are relevant to the drug product.

Example 13—Batch Analysis of Pridopidine HCl Drug Substance

A number of batches of Pridopidine HCl drug substance were manufactured at various manufacturing facilities and subsequently analyzed. All batches contained the known identified impurities Compound 5, Compound 1, Compound 4, Compound 8 Compound 6 and Compound 3 in levels below the qualification limit of 0.15%.

TABLE 38

Analysis of the content of each of the impurities Compound 5, Compound 1, Compound 4, Compound 8 Compound 6 and Compound 3 available in the API batches used for tox studies

| Impurity/Batch No. | Z | Y | X |
|---|---|---|---|
| Compound 5 | NP | NP | <0.05 |
| Compound 1 | NP | NP | 0.06 |
| Compound 4 | NP | <0.05 | 0.06 |
| Compound 8 | 0.02 | NP | <0.05 |
| Compound 6 | NP | <0.05 | <0.05 |
| Compound 2 | NP | NP | <0.05 |
| Compound 3 | NP | <0.05 | <0.05 |
| Largest impurity | 0.15 | <0.05 | <0.05 |

NP-Not performed

Example 14—Batch Analysis of Pridopidine HCl Drug Product

A number of batches of Pridopidine HCl drug product were manufactured at various manufacturing facilities and subsequently analyzed.

TABLE 39

Analysis of Pridopidine HCl Batches used for Non-Clinical and Clinical Studies

| | Related Substances by HPLC [area %] | | | | | | | | | |
|---|---|---|---|---|---|---|---|---|---|---|
| Batch Number | Compound 5 | Compound 1 | Compound 4 (Peak 1) | Compound 8 | Compound 3 (Peak 2) | Compound 2 | Compound 6 (Peak 3) | Compound 9 | Unknown Impurities | Impurities in Total |
| Acceptance Criteria | ≤0.15 | ≤0.15 | ≤0.15 | ≤0.15 | ≤0.15 | ≤0.15 | ≤0.15 | Report value | ≤0.10 each | ≤0.50 |
| A | — | — | — | — | — | — | — | — | — | 0.51 |
| B | — | — | — | — | — | — | — | — | — | 0.26 |
| C | — | — | <0.05 | — | 0.06 | — | <0.05 | — | <0.05 | 0.06 |
| D | — | — | <0.05 | — | <0.05 | — | <0.05 | — | <0.05 | <0.05 |
| E | — | — | <0.05 | — | <0.05 | — | <0.05 | — | 0.09[1] | 0.09 |
| F | — | — | <0.05 | — | <0.05 | — | <0.05 | — | 0.07[1] | 0.07 |
| 1 | — | — | 0.09 | — | ND | — | ND | — | 0.05 | 0.14 |
| 2 | — | — | 0.05 | — | ND | — | ND | — | ND | 0.05 |
| 3 | — | — | 0.05 | — | ND | — | ND | — | ND | 0.06 |
| 4 | <0.05 | <0.05 | 0.08 | <0.05 | 0.07 | <0.05 | <0.05 | <1 | <0.05 | 0.15 |

TABLE 39-continued

Analysis of Pridopidine HCl Batches used for Non-Clinical and Clinical Studies

| Batch Number | Compound 5 | Compound 1 | Compound 4 (Peak 1) | Compound 8 | Compound 3 (Peak 2) | Compound 2 | Compound 6 (Peak 3) | Compound 9 | Unknown Impurities | Impurities in Total |
|---|---|---|---|---|---|---|---|---|---|---|
| 5 | <0.05[2] | <0.05 | <0.05 | <0.05 | 0.10 | <0.05 | <0.05 | <1 | <0.05 | 0.10 |
| G | <0.05 | 0.06 | <0.05 | <0.01 | 0.10 | <0.05 | <0.05 | <1 | <0.05 | 0.15 |
| H | <0.05 | 0.07 | <0.05 | <0.01 | 0.08 | <0.05 | <0.05 | <1 | <0.05 | 0.14 |
| I | <0.05 | <0.05 | 0.06 | <0.01 | 0.11 | <0.05 | <0.05 | <1 | <0.05 | 0.17 |
| J | <0.05 | <0.05 | <0.05 | <0.01 | <0.05 | <0.05 | <0.05 | 1 | <0.05 | <0.05 |
| K | <0.05 | 0.07 | <0.05 | <0.01 | 0.08 | <0.05 | <0.05 | <1 | <0.05 | 0.15 |

Compound 9 is 4-hydroxy-4-(3-(methylsulfonyl)phenyl)-1-propylpiperidin-1-ium chloride.

What is claimed is:

1. A pharmaceutical composition comprising pridopidine or salt thereof and compound (1) or salt thereof

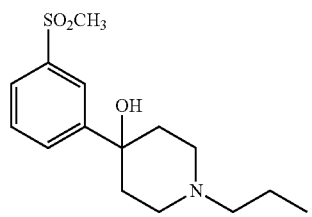

(1)

and one or more excipients.

2. A pharmaceutical composition comprising pridopidine salt and compound (1) or salt thereof

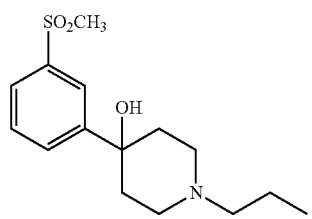

(1)

and one or more excipients.

3. A pharmaceutical composition comprising pridopidine or salt thereof and combination of compound (1) or salt thereof and compound (4) or salt thereof

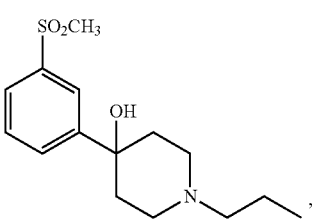

(1)

-continued

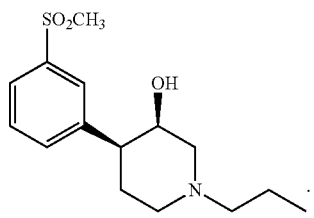

(4)

4. A pharmaceutical composition comprising pridopidine or salt thereof and at least one of compounds 1-8 or salts thereof;

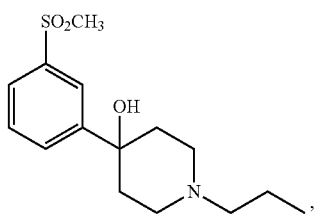

(1)

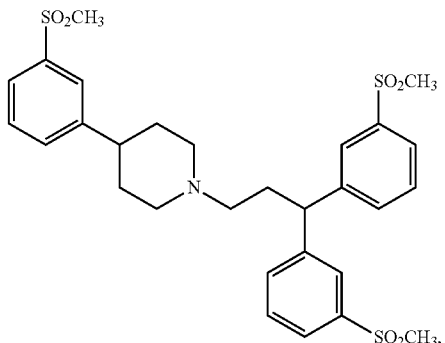

(2)

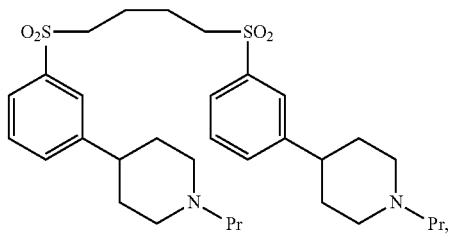

(3)

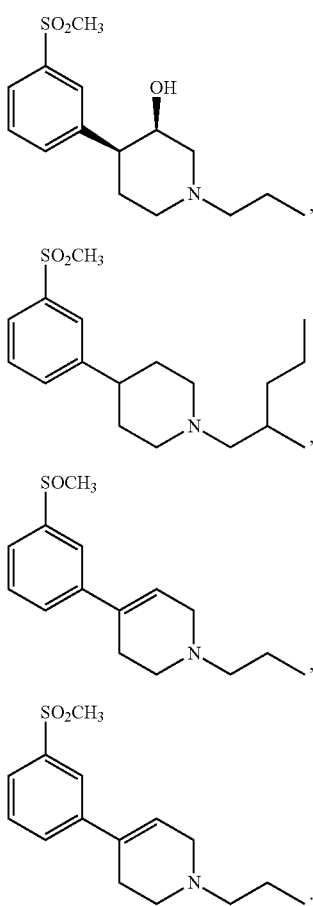

5. The composition of claim 1, wherein the composition comprises pridopidine salt, wherein the salt is hydrochloride, hydrobromide, nitrate, perchlorate, phosphate, sulphate, formate, acetate; aconate, ascorbate, benzenesulphonate, benzoate cinnamate, citrate, embonate, enantate, fumarate, glutamate, glycolate, lactate, maleate, malonate, mandelate, methane-sulphonate, naphthalene-2-sulphonate, phthalate, salicylate, sorbate, stearate, succinate, tartrate or toluene-p-sulphonate salt.

6. The composition of claim 1, wherein the composition comprises pridopidine salt, wherein the salt is hydrochloride salt.

7. The composition of claim 3, wherein the composition comprises pridopidine salt, wherein the salt is hydrochloride, hydrobromide, nitrate, perchlorate, phosphate, sulphate, formate, acetate, aconate, ascorbate, benzenesulphonate, benzoate, cinnamate, citrate, embonate, enantate, fumarate, glutamate, glycolate, lactate, maleate, malonate, mandelate, methane-sulphonate, naphthalene-2-sulphonate, phthalate, salicylate, sorbate, stearate, succinate, tartrate or toluene-p-sulphonate salt.

8. The composition of claim 3, wherein the composition comprises pridopidine salt, wherein the salt is hydrochloride salt.

9. The composition of claim 1, in the form of a capsule, a tablet, a pill, a powder, a granule, a liquid solution or a liquid suspension.

10. The composition of claim 3, in the form of a capsule, a tablet, a pill, a powder, a granule, a liquid solution or a liquid suspension.

11. The composition of claim 1, in an oral dosage unit form.

12. The composition of claim 3, in an oral dosage unit form.

13. The composition of claim 11, wherein the oral dosage unit form comprises between 22.5-315 mg pridopidine.

14. The composition of claim 12, wherein the oral dosage unit form comprises between 22.5-315 mg pridopidine.

15. The composition of claim 13, wherein the oral dosage unit form comprises between 45-250 mg pridopidine.

16. The composition of claim 14, wherein the oral dosage unit form comprises between 45-250 mg pridopidine.

17. The composition of claim 15, wherein the oral dosage unit form comprises between 45-135 mg pridopidine.

18. The composition of claim 16, wherein the oral dosage unit form comprises between 45-135 mg pridopidine.

19. The composition of claim 13, wherein the oral dosage unit form comprises between 90-315 mg pridopidine.

20. The composition of claim 14, wherein the oral dosage unit form comprises between 90-315 mg pridopidine.

21. The composition of claim 13, wherein the oral dosage unit form comprises about 22.5 mg pridopidine, about 45 mg pridopidine, about 67.5 mg pridopidine, about 90 mg pridopidine, about 100 mg pridopidine, about 112.5 mg pridopidine, about 125 mg pridopidine, about 135 mg pridopidine, about 150 mg pridopidine, about 180 mg pridopidine, about 200 mg pridopidine, about 250 mg pridopidine, or about 315 mg pridopidine.

22. The composition of claim 14, wherein the oral dosage unit form comprises about 22.5 mg pridopidine, about 45 mg pridopidine, about 67.5 mg pridopidine, about 90 mg pridopidine, about 100 mg pridopidine, about 112.5 mg pridopidine, about 125 mg pridopidine, about 135 mg pridopidine, about 150 mg pridopidine, about 180 mg pridopidine, about 200 mg pridopidine, about 250 mg pridopidine, or about 315 mg pridopidine.

23. A method of treating Huntington disease in a subject, comprising administering a pharmaceutical composition of claim 1.

24. A method of treating Huntington disease in a subject, comprising administering a pharmaceutical composition of claim 3.

25. The method of claim 23, wherein the composition is administered once daily or more than once daily.

26. The method of claim 24, wherein the composition is administered once daily or more than once daily.

* * * * *